US011191575B2

(12) United States Patent
Kidman et al.

(10) Patent No.: US 11,191,575 B2
(45) Date of Patent: Dec. 7, 2021

(54) SYSTEMS AND METHODS FOR OFF-AXIS AUGMENTATION OF A VERTEBRAL BODY

(71) Applicant: Stryker Corporation, Kalamazoo, MI (US)

(72) Inventors: Beau Kidman, Kalamazoo, MI (US); Callie Carpenter, Portage, MI (US); Gabriel James Harshman, Portage, MI (US); Kevin Kuiper, Portage, MI (US); Jean-Francois Oglaza, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/887,032

(22) Filed: May 29, 2020

(65) Prior Publication Data
US 2020/0383707 A1 Dec. 10, 2020

Related U.S. Application Data

(60) Provisional application No. 62/858,698, filed on Jun. 7, 2019.

(51) Int. Cl.
*A61B 17/70* (2006.01)
*A61B 17/34* (2006.01)
*A61B 17/00* (2006.01)

(52) U.S. Cl.
CPC ...... *A61B 17/7097* (2013.01); *A61B 17/3423* (2013.01); *A61B 17/3472* (2013.01); *A61B 2017/00991* (2013.01)

(58) Field of Classification Search
CPC ............ A61B 17/1631; A61B 17/1642; A61B 17/164; A61B 17/1644; A61B 2017/564;
(Continued)

(56) References Cited

U.S. PATENT DOCUMENTS

| 4,748,969 | A | * | 6/1988 | Wardle | ................. A61B 1/0051 138/120 |
| 4,947,827 | A | * | 8/1990 | Opie | .................. A61B 1/00073 600/108 |

(Continued)

FOREIGN PATENT DOCUMENTS

WO 2019200091 A1 10/2019

*Primary Examiner* — Anu Ramana
(74) *Attorney, Agent, or Firm* — Howard & Howard Attorneys PLLC

(57) ABSTRACT

Systems and methods for augmenting a vertebral body may include an optional access cannula, introducer device, and a stylet having a stylet shaft. The access cannula includes a hub portion and a cannula shaft extending from the cannula hub. The cannula shaft includes a distal end positionable within the vertebral body that defines a lumen along a longitudinal axis. The introducer device may be a telescoping or pivoting introducer device that is removably coupled to the hub portion of the access cannula. The introducer device controls the movement of the flexible distal portion of the stylet shaft and the flexible sheath from within the introducer device through the access cannula to within a target site in the vertebral body, wherein the flexible distal portion is moved from the constrained to the unconstrained state to displace cancellous bone within the target site.

20 Claims, 39 Drawing Sheets

(58) Field of Classification Search
CPC ............ A61B 17/8816; A61B 17/8819; A61B 17/885; A61B 17/8855; A61B 17/7097; A61B 1/005; A61B 1/0051; A61B 1/0052; A61B 1/0056; A61B 1/008; A61B 1/012; A61B 2017/003; A61B 2017/00305; A61B 2017/00309; A61B 2017/00314; A61B 2017/00318; A61B 17/3421; A61B 17/3423; A61B 17/3443; A61B 17/3472; A61B 2017/3443
See application file for complete search history.

(56) References Cited

U.S. PATENT DOCUMENTS

| | | | |
|---|---|---|---|
| 5,788,713 A | 8/1998 | Dubach et al. | |
| 5,873,817 A * | 2/1999 | Kokish | A61B 1/0058 |
| | | | 600/143 |
| 5,899,914 A * | 5/1999 | Zirps | A61B 17/1608 |
| | | | 606/170 |
| 6,176,852 B1 | 1/2001 | Ischinger | |
| 6,425,887 B1 * | 7/2002 | McGuckin | A61B 17/3468 |
| | | | 604/272 |
| 6,547,432 B2 | 4/2003 | Coffeen et al. | |
| 6,592,559 B1 * | 7/2003 | Pakter | A61B 17/3417 |
| | | | 604/272 |
| 6,875,219 B2 | 4/2005 | Arramon et al. | |
| 7,658,537 B2 | 2/2010 | Coffeen et al. | |
| 8,114,057 B2 | 2/2012 | Gerdts et al. | |
| 8,894,658 B2 | 11/2014 | Linderman et al. | |
| 8,961,553 B2 | 2/2015 | Hollowell et al. | |
| 9,161,839 B2 | 10/2015 | Flom et al. | |
| 9,375,252 B2 | 6/2016 | Coe et al. | |
| 9,579,130 B2 | 2/2017 | Oglaza et al. | |
| 9,775,627 B2 | 10/2017 | Patel et al. | |
| 9,802,024 B2 | 10/2017 | McGuckin, Jr. | |
| 10,441,295 B2 | 10/2019 | Brockman et al. | |
| 10,660,656 B2 | 5/2020 | Purdy et al. | |
| 2004/0049157 A1 * | 3/2004 | Plishka | A61B 17/3415 |
| | | | 604/164.09 |
| 2010/0298832 A1 | 11/2010 | Lau et al. | |
| 2013/0006232 A1 | 1/2013 | Pellegrino et al. | |
| 2014/0005474 A1 | 1/2014 | Farin et al. | |
| 2014/0018732 A1 * | 1/2014 | Bagaoisan | A61M 25/0136 |
| | | | 604/95.04 |
| 2016/0324541 A1 | 11/2016 | Pellegrino et al. | |
| 2018/0126121 A1 | 5/2018 | Mauch | |

* cited by examiner

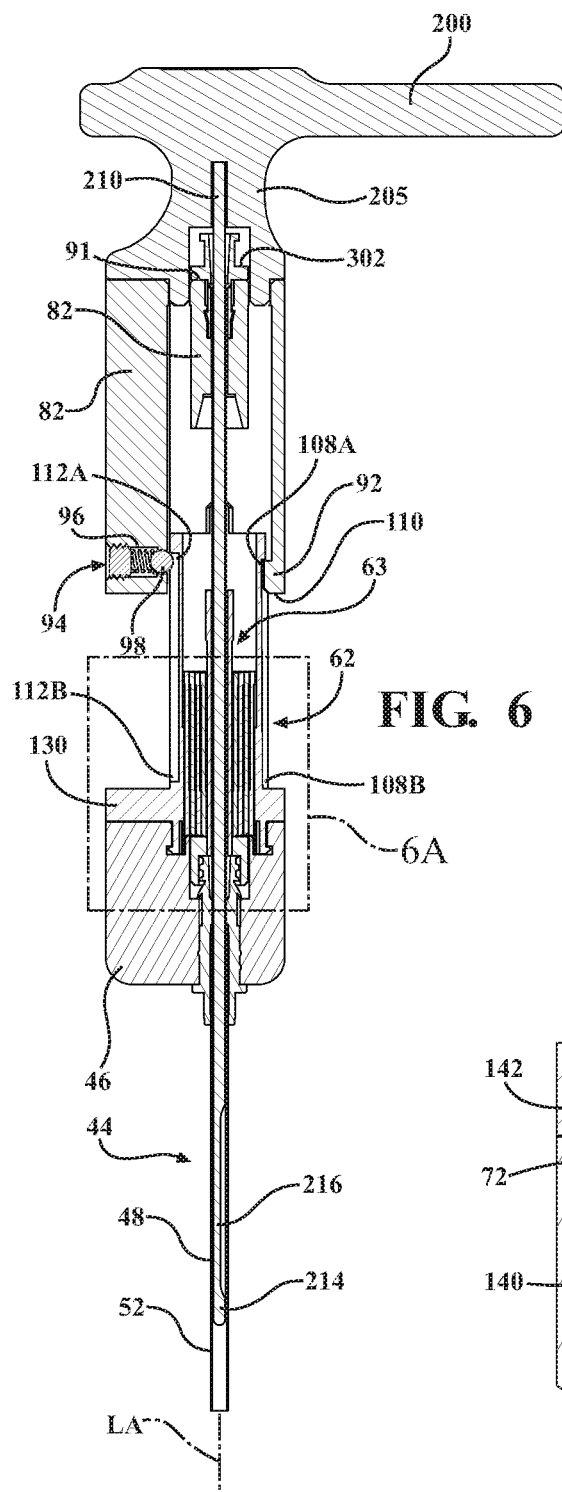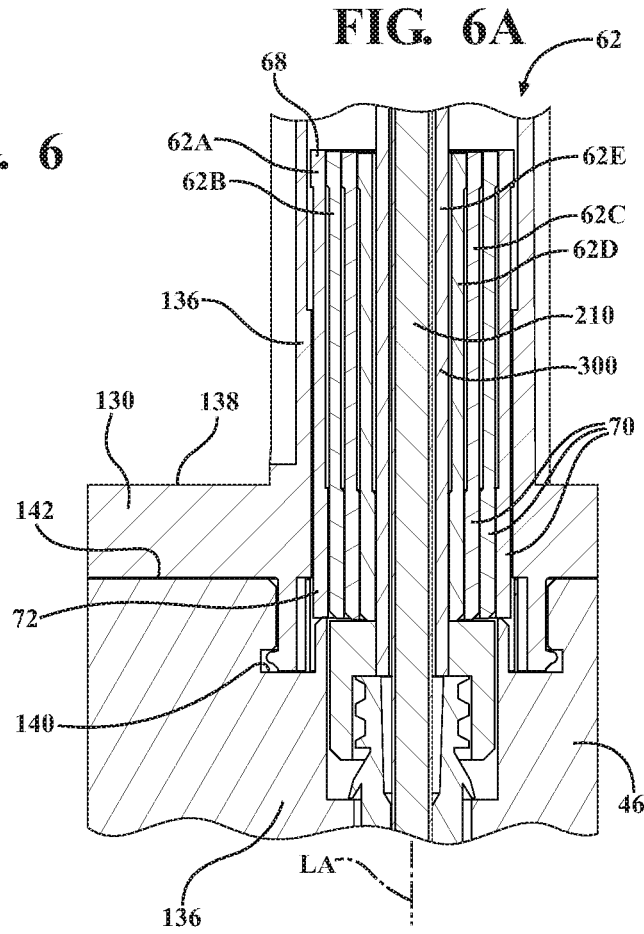

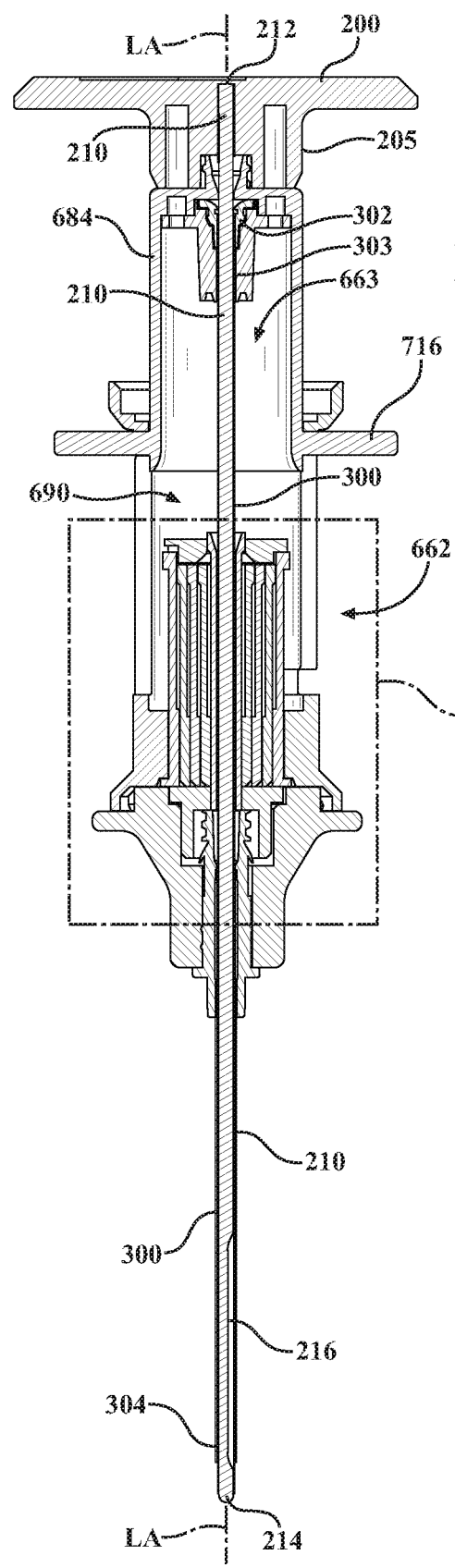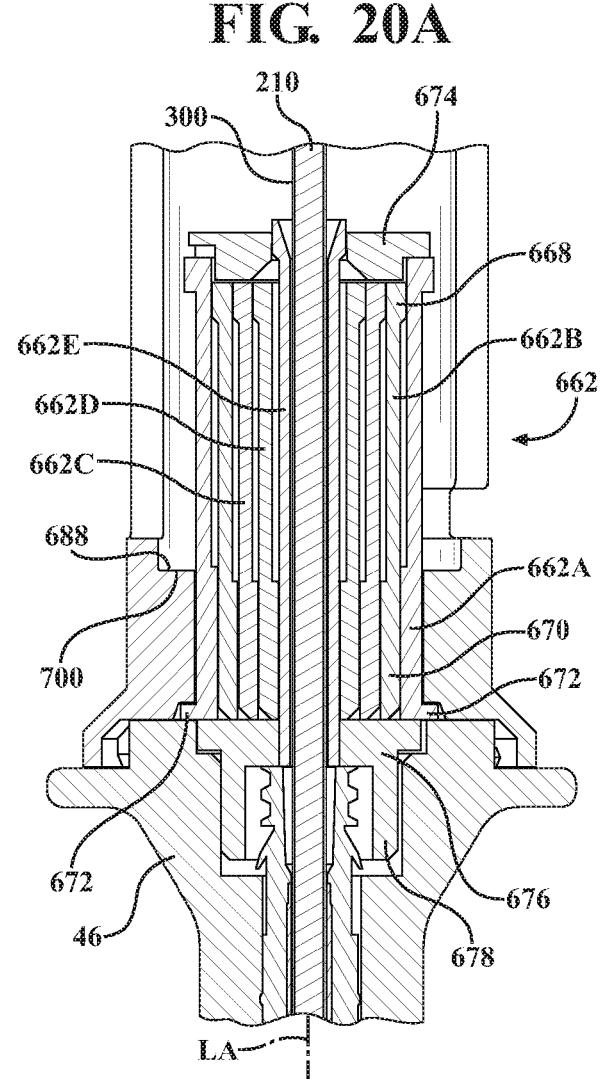
FIG. 20
FIG. 20A

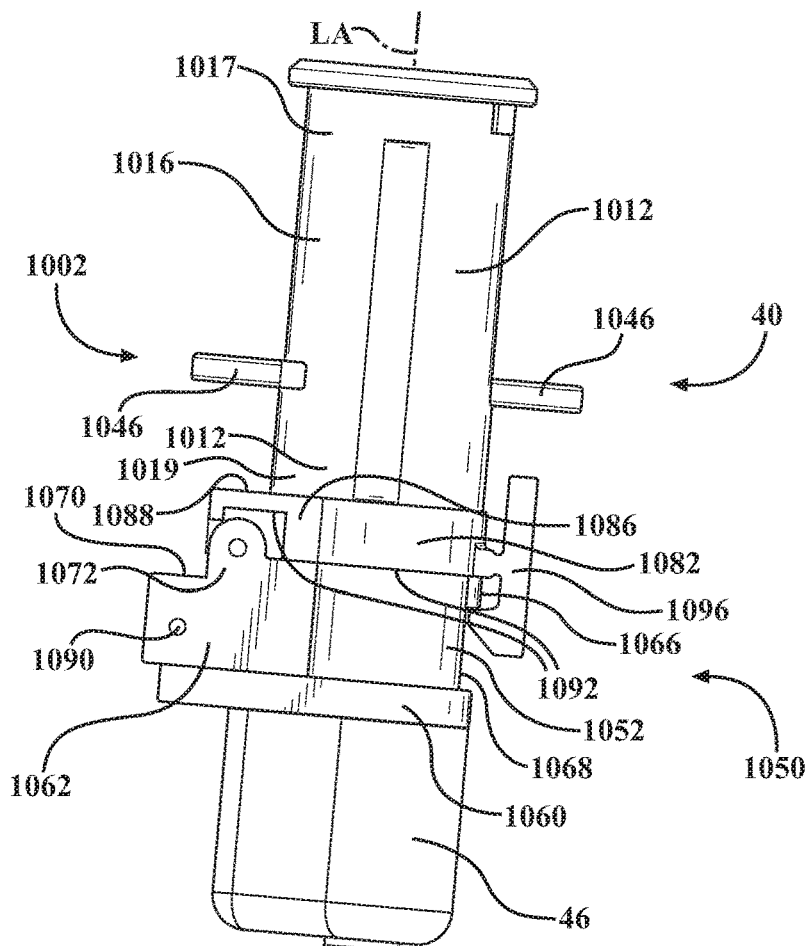
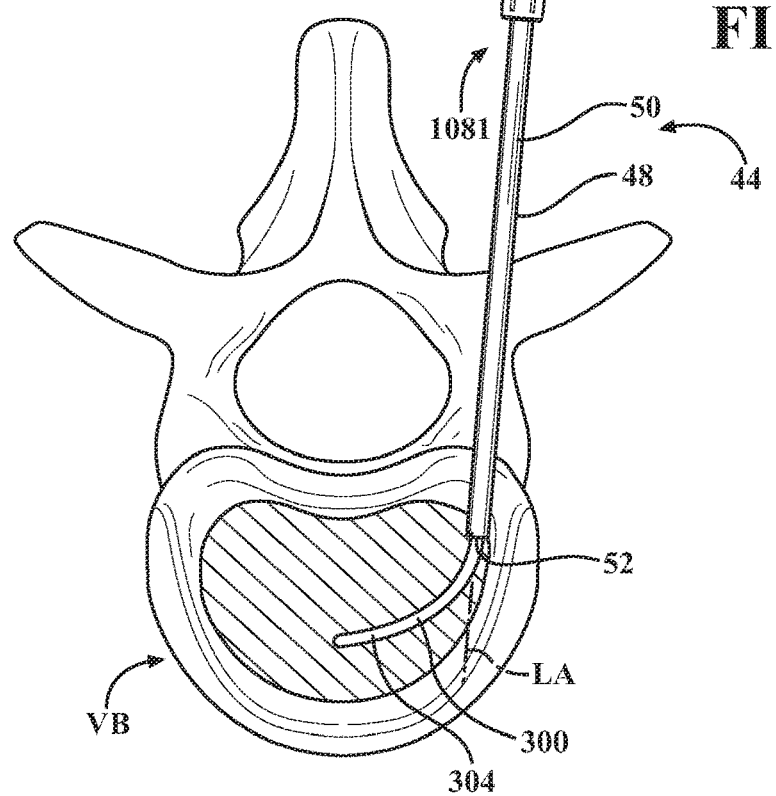
FIG. 34

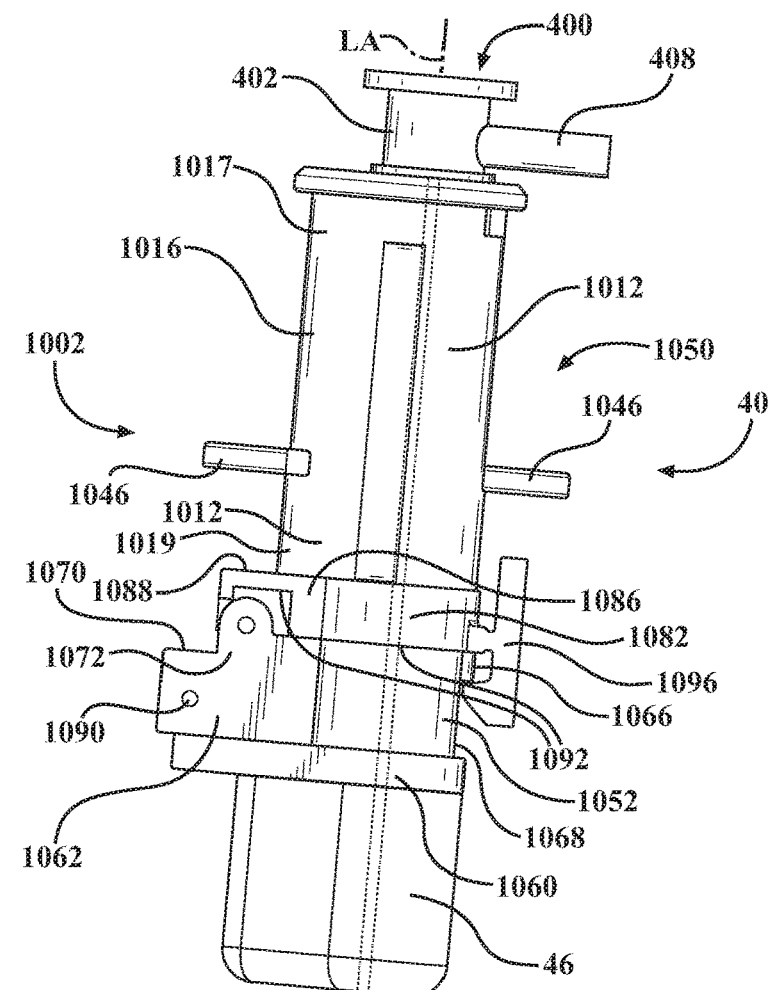
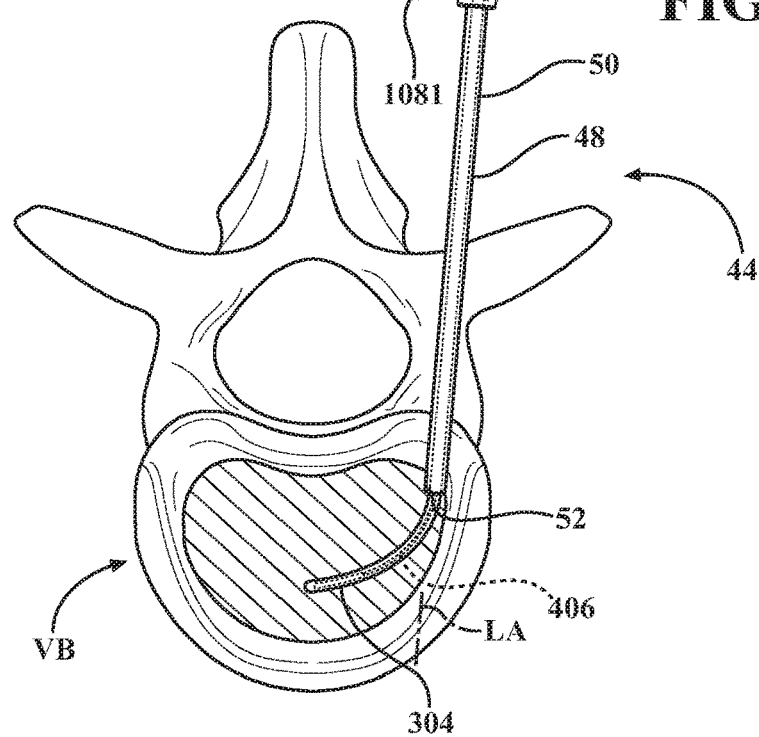
FIG. 35

SYSTEMS AND METHODS FOR OFF-AXIS AUGMENTATION OF A VERTEBRAL BODY

PRIORITY CLAIM

This application claims priority to and all the benefits of U.S. Provisional Patent Application No. 62/858,698, filed Jun. 7, 2019, the entire contents of which are hereby incorporated by reference.

BACKGROUND

A common source of back pain is a vertebral compression fracture in which a weakened or injured vertebral body loses height or collapses. The weakening of the vertebral body may be due to acute injury or, more often, degenerative changes such as osteoporosis. The compression fractures often appear on lateral radiographs as wedge deformities with greater loss of height anteriorly.

One treatment modality includes vertebral augmentation in which the height of the vertebral body is elevated or restored, and stabilized at the elevated or restored height. A vertebroplasty includes delivering curable material, for example a bone cement, within an interior of the vertebral body. The material interdigitates with cancellous bone and cures to stabilize the vertebral body. A kyphoplasty includes creating a cavity within the interior of the vertebral body by compressing the cancellous bone with an expandable member such as a balloon, and delivering the curable material into the cavity. The expandable member may facilitate elevating or restoring the height of the vertebral body.

Accessing the interior of the vertebral body often includes percutaneously placing an access cannula through a pedicle of the vertebra. Owing to the structure of the vertebra, accessing a location on the contralateral side of the vertebral body is not especially feasible with straight instrumentation. As such, one existing kyphoplasty technique employs a bipedicular approach in which two access cannulas are placed, followed by two balloons each positioned ipsilaterally within the interior of the vertebral body. The bipedicular approach undesirably requires twice the trauma to tissue, and often requires twice the instrumentation.

Of particular interest is a unipedicular approach in which the instrumentation is designed to access locations of the interior of the vertebral body offset from a longitudinal axis of the access cannula, including locations on the contralateral side of the vertebral body. One exemplary system utilizing the unipedicular approach is disclosed in commonly owned U.S. Pat. No. 8,894,658, issued Nov. 25, 2014, hereby incorporated by reference in its entirety, and sold under the tradename Avaflex by Stryker Corporation (Kalamazoo, Mich.). While the disclosure realizes the benefits of the unipedicular approach, it can be difficult to insert the stylet including the shape memory shaft within the small hole contained in the cannula hub, and down the hollow shaft of the access cannula to within the vertebral body, using the unipedicular approach of this disclosure.

Accordingly, there is still a need there is further need in the art for systems and methods having a simpler approach for off-axis vertebral augmentation using a unipedicular approach.

SUMMARY

A first aspect of the present disclosure is directed to a system for augmenting a vertebral body. The system may include an optional access cannula, introducer device, and a stylet. The access cannula includes a hub portion and a cannula shaft extending from the cannula hub. The cannula shaft includes a distal end positionable within the vertebral body, and the cannula shaft also defines a lumen along a longitudinal axis. The introducer device may include a telescoping introducer shaft coupled to a hub assembly that is removably coupled to the hub portion of the access cannula. The telescoping introducer shaft has a plurality of shaft sections moveable between an extended position and a non-extended position. The shaft sections may have a longer longitudinal length in the extended position and a shorter longitudinal length in the non-extended position. The telescoping introducer shaft may define an internal bore extending along the longitudinal axis with the internal bore aligned with and in open communication with the lumen along the longitudinal axis when the telescoping introducer shaft is coupled to the hub portion of the access cannula. The stylet may be introduced within the internal bore of the telescoping introducer shaft and includes a stylet shaft extending a length between a proximal end and a distal end and having a flexible distal portion near the distal end. The flexible distal portion has a pre-set curve in an unconstrained state and is movable between the unconstrained state and a constrained state in which the flexible distal portion is substantially straight. The length of the stylet shaft between the proximal and distal ends is contained within the internal bore of the telescoping introducer shaft when the telescoping introducer shaft is in the extended position such that the flexible distal portion is in the constrained state when the flexible distal portion is contained within the internal bore. In addition, the collapsing of the telescoping introducer shaft from the extended position to the non-extended position moves the flexible distal portion of the distal end of the stylet shaft from within the internal bore to within the lumen of the access cannula in the constrained state.

In some implementations, the hub assembly further includes an outer hub, and an inner hub coupled to the stylet and moveable along the longitudinal axis relative to the outer hub between an initial position and a supplemental position in which the inner hub is moved distally relative to the outer hub. The length of the stylet shaft is sufficient for the flexible distal portion of the shaft to extend through and be operable beyond the distal end of the access cannula when the telescoping introducer shaft is in the non-extended position and when the inner hub is in the supplemental position such that the pre-set curve is no longer constrained by the access cannula and moves from the constrained state to the unconstrained state to a target area within the vertebral body that is offset from the longitudinal axis.

In some implementations, a flexible sheath at least partially overlies the stylet shaft when the stylet is inserted within the internal bore. The flexible sheath may include a proximal end coupled to the inner hub and an opposing distal end positionable near the distal end of the stylet shaft. The distal end of the shaft may be in registration with the distal end of the access cannula when the telescoping introducer shaft is in the non-extended position and when the inner hub is in the initial position. An outermost shaft section of the plurality of shaft sections may be retained within the inner hub in each of the non-extended and extended positions. The inner hub may include an initial locking feature and wherein the outer hub include a first complementary locking feature. The initial locking feature configured for locking with the complementary initial locking feature when the inner hub is in the initial position. The inner hub may include a supplemental locking feature and wherein the outer hub include a complementary supplemental locking feature. The supplemental locking feature may be configured for locking with the complementary supplemental locking feature when the inner hub is in the supplemental position.

In some implementations, the distal end of the flexible sheath is configured to remain curved near the target area within the vertebral body when the stylet is removed from the vertebral body while the supplemental locking feature of the inner hub remains locked with the complementary supplemental locking feature of the outer hub in the supplemental position and while the telescoping introducer shaft remains in the non-extended position. The distal end of the flexible sheath may be further configured to be retracted from the vertebral body to a position within the lumen when the stylet is removed from the introducer device and when the inner hub moves from the supplemental position to the initial position while the telescoping introducer shaft remains in the non-extended position. A balloon hub assembly may be configured to be coupled to the introducer device after removal of the stylet from the introducer device. The balloon assembly may include a balloon hub assembly for coupling to the introducer device. The balloon hub assembly may include an inflation port. The balloon assembly may have a proximal end portion coupled to the inflation port. The balloon may extend through the flexible sheath such that a distal end portion opposite the proximal end portion is contained within the target area of the vertebral body. An inflation device may be coupled to the inflation port. The inflation device configured for inflating and deflating the distal end portion of the balloon assembly within the target area of the vertebral body. The balloon hub assembly may have an inner region. The inner hub is may be within the inner region when the inner hub is in the initial position.

In some implementations, the distal end of the flexible sheath is positioned around a portion of the distal end portion of the balloon assembly within the vertebral body when the inner hub is locked in the supplemental position while the telescoping introducer shaft remains in the non-extended position. The distal end of the flexible sheath may be configured to retract from the vertebral body towards the lumen when the inner hub is moving in a direction from the supplemental position towards the initial position while the telescoping introducer shaft remains in the non-extended position. The inflation the distal end portion of the balloon within the vertebral body by the inflation device may displace cancellous bone within the target area of the vertebral body to form a cavity region.

In some implementations, a delivery device is provided for coupling to the introducer device after formation of the cavity region, and after removal of the balloon assembly from the introducer device. The delivery device may be configured for delivering a curable material through the flexible sheath to the cavity region within the target area of the vertebral body.

The outer hub may include a longitudinally extending outer surface and an opposing longitudinally extending inner surface defining an interior region configured for receiving the inner hub. The outer hub may include a slot extending through and between the longitudinally extending outer surface and the opposing longitudinally extending inner surface. The slot may include an initial slot locking region corresponding to the initial position and a supplemental slot locking region corresponding the supplemental position and a longitudinally extending middle slot region connecting the initial and supplemental slot locking regions. The initial and supplemental slot locking regions may extend in a direction transverse to the longitudinally extending middle slot region. The inner hub may include an alignment member extending outwardly from a longitudinally extending outer surface that is disposed through the slot.

In some implementations, the inner hub has a longitudinally extending outer surface including a first channel extending between a distal end and a proximal end. The channel may include a longitudinally extending first channel portion and a transversely extending second channel portion extending from the proximal end. The transversely extending second channel portion extending a first distance between a first transverse end and a second transverse end. The outer hub may include a longitudinally extending outer surface and an opposing longitudinally extending inner surface defining an inner region. The longitudinally extending inner surface may include a tab portion received within the channel. Positioning of the tab portion within the transversely extending second channel portion at the first transverse end or the second transverse end may correspond to the initial position. The longitudinally extending outer surface of the inner hub further may include a second channel distinct from the first channel extending between the distal end and the proximal end. A semi-circular detent channel may be positioned transverse to and spaced from the distal end of the second channel. The outer hub may include a circular detent opening extending through and between the longitudinally extending outer surface and the opposing longitudinally extending inner surface. A biasing device may be coupled within the circular detent opening. A ball may be coupled to the biasing device and contained within the circular detent opening such that the biasing device is between the ball and the longitudinally extending outer surface. The ball may be disposed within the semi-circular detent channel when the tab portion is positioned at the second transverse end of the transversely extending second channel portion. The ball is disposed within the second channel when the tab portion is positioned at the first transverse end of the transversely extending second channel portion, or the tab portion may be positioned along the first channel between the distal end and the proximal end.

A second aspect of the disclosure involves a method of augmenting a vertebral body according to the first aspect of the disclosure, and optionally, any of its corresponding implementations.

A third aspect of the present disclosure is directed to a system for augmenting a vertebral body. The system may include an optional access cannula, introducer device, and a stylet. The access cannula includes a hub portion and a cannula shaft extending from the cannula hub. The cannula shaft includes a distal end positionable within the vertebral body that defines a lumen along a longitudinal axis. The introducer device includes a hub assembly, moveable along the longitudinal axis between an initial position and a supplemental position, and a pivoting member including a base portion coupled to a pivoting portion configured for coupling to the hub portion of the access cannula, wherein the base portion defines a first bore coaxial with the longitudinal axis when the base portion is coupled to the hub portion. The pivoting portion is coupled to the hub assembly and defines a second bore, with the pivoting portion pivotable relative to the base portion between an upright position, in which the first and second bores are coaxially aligned, and a prone position, in which the first and second bores are not coaxially aligned. The stylet for insertion within the introducer device includes a stylet shaft extending a length between a proximal end and a distal end and has a flexible distal portion near the distal end. The flexible distal portion includes a pre-set curve in an unconstrained state and movable between the unconstrained state and a constrained state in which the flexible distal portion is substantially straight. The stylet is moveable between a non-deployed position and a deployed position when the pivoting portion is coupled to the base portion in the upright position. They system includes wherein a portion of the distal end of the stylet shaft is configured to extend through and be operable beyond the distal end of the access cannula when the pivoting member is in the upright position and the hub assembly is in the supplemental position and wherein the stylet is movable to the deployed position such that the pre-set curve moves from the constrained state to the unconstrained state to a target area within the vertebral body that is offset from the longitudinal axis.

In some implementations, the pivoting portion is integral with the hub assembly. A flexible sheath may at least partially overlie the shaft when the stylet is inserted within the first and second bores, with the flexible sheath including a proximal end coupled to the hub assembly and an opposing distal end positionable near the distal end of the stylet shaft. The distal end of the shaft may be in registration with the distal end of the access cannula when the hub assembly is in the initial position and the stylet is in the deployed position and the pivoting member is in the upright position. The distal end of the flexible sheath may be configured to be retracted from the vertebral body to the lumen when the stylet is removed from the introducer device.

In some implementations, the pivoting portion includes a snap that is configured to be releasably coupled to the base portion when the pivoting portion is in the upright position. The base portion may include a hollow interior portion that is positioned around the hub portion of the access cannula when the base portion is coupled to the hub portion of the access cannula. The base portion may further include a ball-nose spring positioned within the hollow interior portion. The ball-nose spring may be biasingly engaged to the hub portion of the access cannula when the base portion is coupled to the hub portion of the access cannula. The pivoting portion may include a snap that is configured to be releasably coupled within a recessed region of an outer surface of the base portion when the pivoting portion is in the upright position. A bottom surface of the pivoting portion and a top surface of the base portion may define an angle α therebetween when the pivoting portion is in the prone position, the angle α being between 0 and 75 degrees. A bottom surface of the pivoting portion and a top surface of the base portion may define an angle α therebetween when the pivoting portion is in the prone position, the angle α being between 0 and 75 degrees.

A fourth aspect of the disclosure involves a method of augmenting a vertebral body according to the third aspect of the disclosure, and optionally, any of its corresponding implementations, and optionally, any of the implementations corresponding to the first aspect of the disclosure.

A fifth aspect of the present disclosure is directed to a system for augmenting a vertebral body. The system may include an access cannula and an introducer device. The introducer device includes a stylet having a length defined between a proximal end and a distal end and a flexible distal portion near the distal end having a pre-set curve in an unconstrained state. The introducer device also includes a pivoting member including a base portion removably coupled to the cannula hub and defining a first bore coaxial with a longitudinal axis when the base portion is removably coupled to the cannula hub. The introducer device also includes a pivoting portion pivotably coupled to the base portion and defining a second bore, wherein the pivoting portion is configured to move between a prone position in which the first and second bores are not coaxially aligned, and an upright position in which the first and second bores are coaxially aligned. The system further includes wherein the flexible distal portion extends between the pivoting portion and the base portion in the unconstrained state with the pivoting member in the prone position, and wherein the flexible distal portion is movable from the unconstrained state to a constrained state in which the flexible distal portion is substantially straight when the pivoting member is moved to the upright position.

In some implementations, a hub assembly is coupled at or near the proximal end of the stylet with the pivoting member spaced apart from the hub assembly by a portion of the length of the stylet. The hub assembly is configured to be distally advanced towards the pivoting member with the pivoting member in the upright position such that the stylet is advanced into the cannula shaft in the constrained state.

BRIEF DESCRIPTION OF THE DRAWINGS

Advantages of the present invention will be readily appreciated as the same becomes better understood by reference to the following detailed description when considered in connection with the accompanying drawings.

FIG. 6 is a section view of the stylet coupled to and contained within the introducer device of FIG. 4 with the introducer device in the non-extended position and the hub assembly in the initial position.

FIG. 6A is a close-up of a portion of the section view of FIG. 6 contained within Rectangle 6A.

FIG. 20 is a section view of the stylet coupled to and contained within the introducer device of FIG. 18 with the introducer device in the non-extended position and the hub assembly in the initial position.

FIG. 20A is a close-up of a portion of the section view of FIG. 20 contained within Rectangle 20A.

FIG. 24 also shows the rotational movement of the inner hub relative to the outer hub in a first direction to move the hub assembly from the supplemental and unlocked position to the supplemental and locked position.

FIG. 33 also shows the rotational movement of the inner hub relative to the outer hub in a first direction to move the hub assembly from the supplemental and unlocked position to the supplemental and locked position FIG. 34 is a perspective and partial section view of FIG. 33 with the stylet removed, with the introducer device in the upright position and the hub assembly in the supplemental and unlocked position, and with the distal end of the access cannula inserted within the vertebral body.

FIG. 35 is a perspective and partial section view of FIG. 34 with a balloon assembly coupled to the introducer device, with the introducer device in the upright position and the hub assembly in the supplemental and unlocked position, and with the balloon in a deflated state.

DETAILED DESCRIPTION

Figure 1:
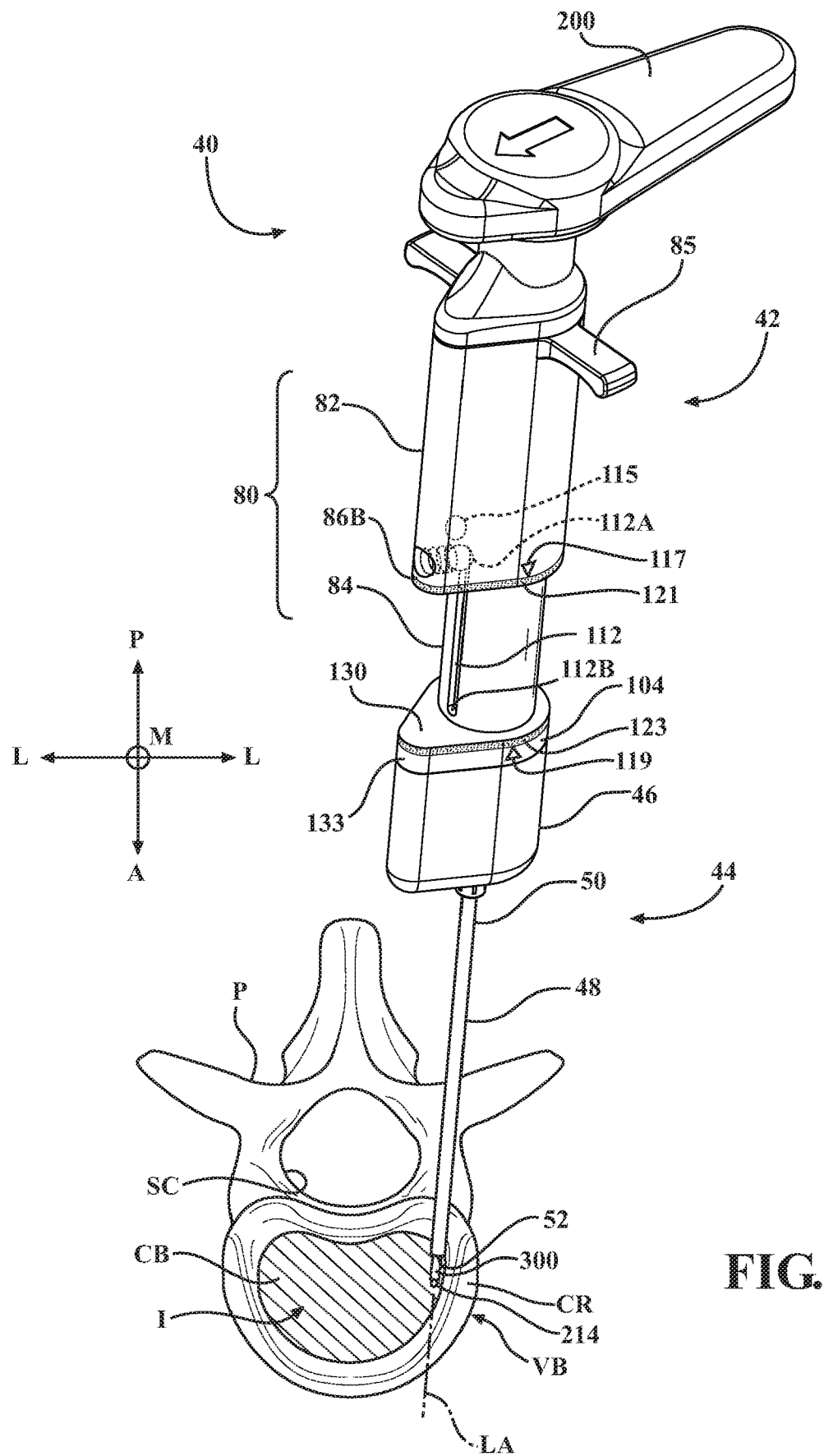
FIG. 1 shows a system for augmenting a vertebral body including a stylet, a telescoping introducer device, and an access cannula, with the stylet coupled to and contained within the introducer device which is coupled to the access cannula, with the introducer device in the non-extended position and the hub assembly in the initial position and unlocked position, and with the distal end of the access cannula inserted within the vertebral body.
Figure 2:
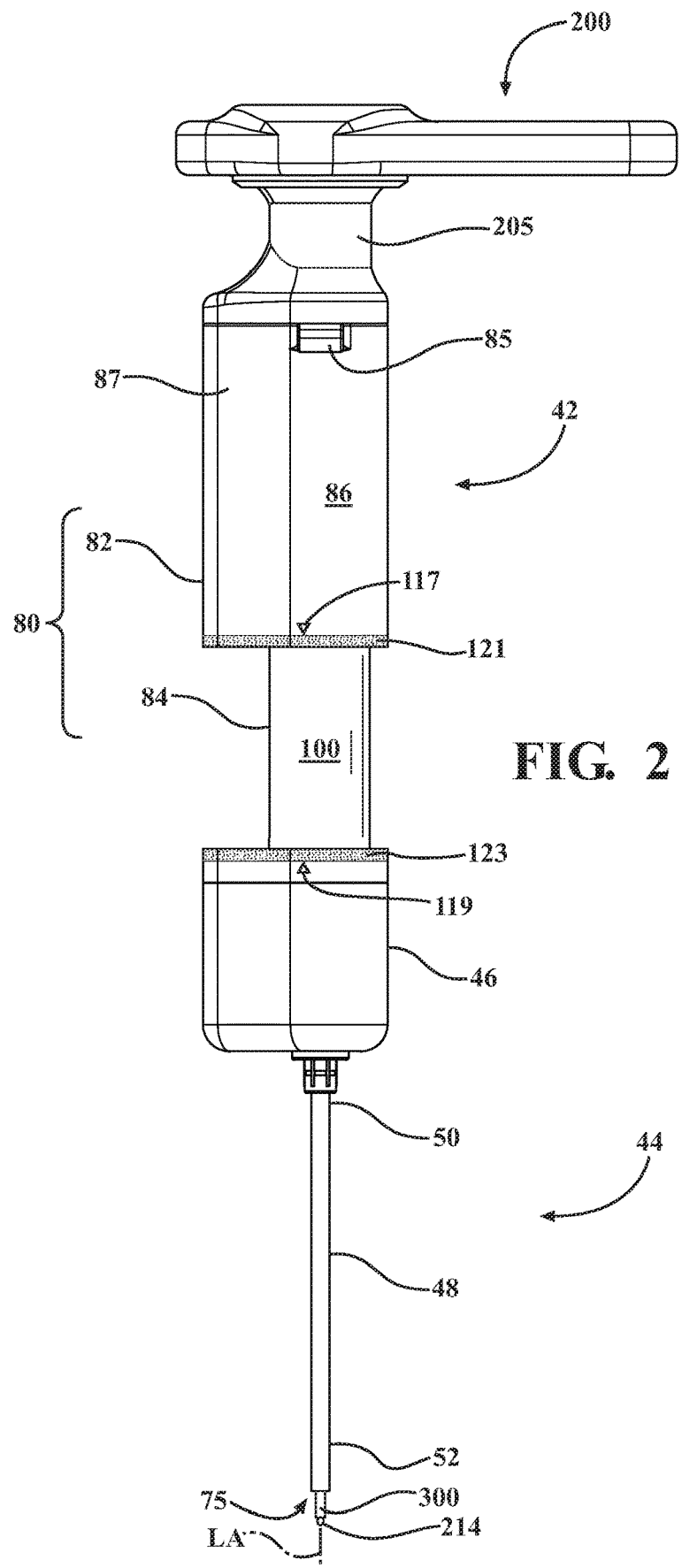
FIG. 2 is a side perspective view of the system of FIG. 1 without the vertebral body.

FIG. 1 shows a system 40 for augmenting a vertebral body. An illustration of an axial section of a vertebra (V) is shown with certain structures and regions to be referenced throughout the present disclosure. The vertebra (V) includes pedicles (P) on opposing lateral sides of a spinal canal (SC) that provide a generally linear path from a posterior approach to an interior (I) region of the vertebral body (VB). The vertebral body (VB) includes a cortical rim (CR) formed from cortical bone that at least partially defines the interior (I) region. A volume of cancellous bone (CB) is within the interior (I) region. With reference to the compass rose of FIG. 1, the anatomical directions may also be referenced in accordance with standard medical convention; i.e., medial (M) to the center of the body, lateral (L) to the sides of the body, anterior (A) to the front of the body, and posterior (P) to the rear of the body.

The system 40 includes an access cannula 44 and an introducer device 42 coupled to the access cannula 44. With further reference to FIGS. 2-14, in addition to FIG. 1, the system 40 also includes a stylet 200 including a shaft 210 extending a length from a stylet base portion 205 between a proximal end 212 and a distal end 214 and having a flexible distal portion 216 near the distal end 214 with the flexible distal portion 216 movable between a constrained state and an unconstrained state. The system 40 also includes a flexible sheath 300 coupled to the introducer device 42 and at least partially overlying the flexible distal portion 216 of the shaft 210.

The access cannula 44 includes a cannula hub portion 46, and a cannula shaft 48 extending from the cannula hub portion 46. The cannula shaft 48 includes a proximal end 50 coupled to the cannula hub portion 46, and a distal end 52 opposite the proximal end 50. The cannula shaft 48 may be straight and defines a lumen 75 extending between the proximal and distal ends 50, 52 such that the cannula shaft 48 is tubular in shape. The cannula shaft 48 may be formed from biocompatible materials with sufficient mechanical properties to maintain integrity as the cannula shaft 48 is driven through the pedicle of the vertebra. The system 40 may include a trocar (not shown) removably positioned within the cannula shaft 48 during placement of the distal end 52 of the cannula shaft 48 into the vertebral body. The trocar may include a length slightly greater than a length of the cannula shaft 48 such that a sharp tip of the trocar pierces the cortical bone of the cortical rim, and the trocar prevents coring of tissue within the lumen 75 of the cannula shaft 48. Once the distal end 52 of the cannula shaft 48 is positioned within the vertebral body, for example as shown in FIG. 1, the trocar is removed. The access cannula 44 provides a working channel to within the interior region of the vertebral body along a longitudinal axis (LA) defined by the cannula shaft 48. The cannula hub portion 46 is exposed above the tissue overlying the vertebra, and configured to be engaged by the introducer device 42.

Figure 3:
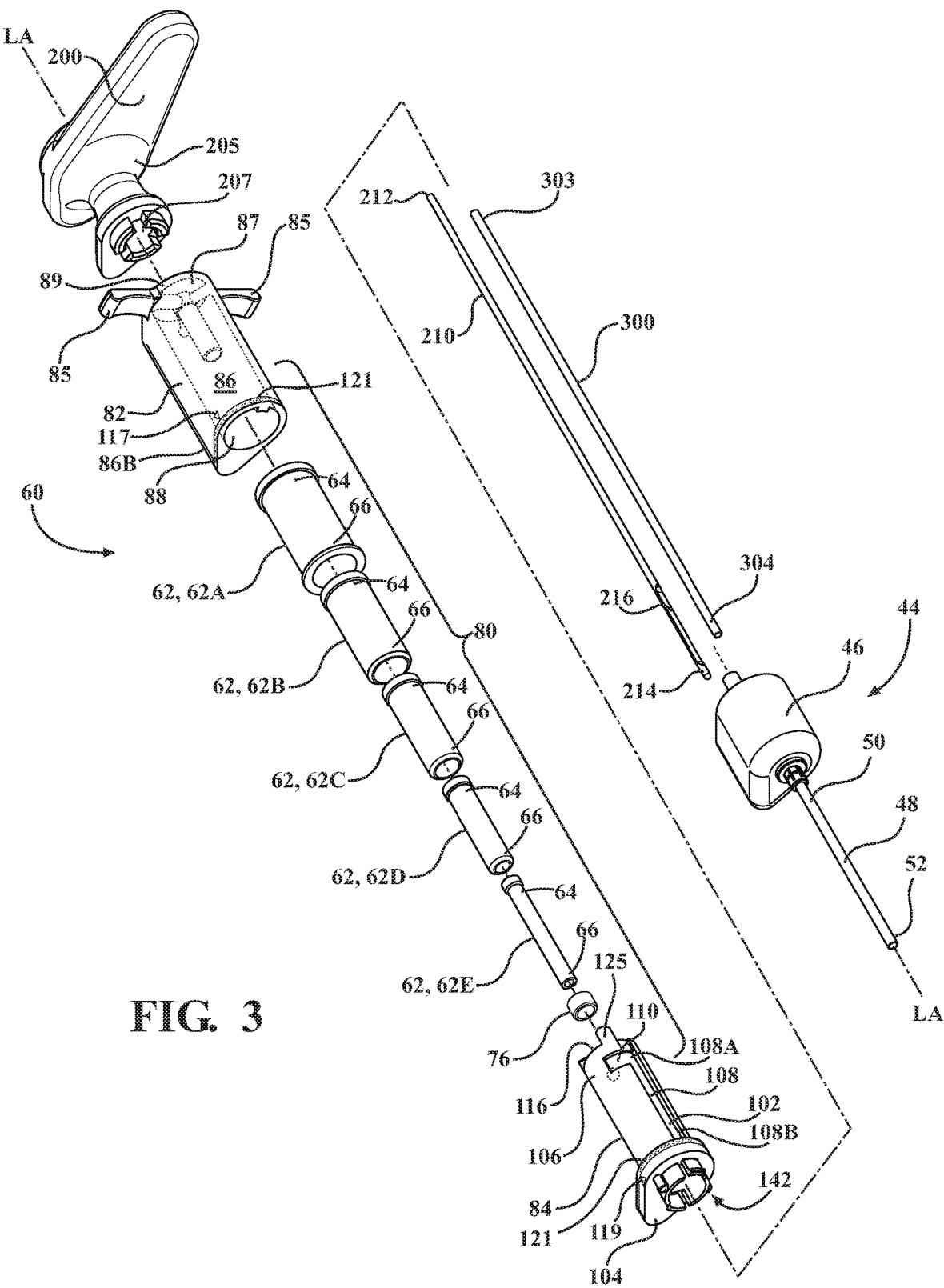
FIG. 3 is an exploded view of the telescoping introducer device of FIGS. 1 and 2.

The introducer device 42 includes a telescoping introducer shaft 60 coupled to a hub assembly 80. The telescoping introducer shaft 60 has a plurality of shaft sections 62 (shown as five shaft sections 62A, 62B, 62C, 62D and 62E as best shown in FIGS. 3-8) moveable between an extended position, or telescoping position (see FIGS. 4, 5 and 8), and a non-extended position (see, for example, FIGS. 6, 6A and 7), with the telescoping introducer shaft 60 defining an internal bore 63 extending along the longitudinal axis LA with the internal bore 63, with the internal bore 63 configured so as to receive the stylet shaft 210 of a stylet assembly 200 when the telescoping introducer shaft 60 is coupled to the cannula hub portion 46 of the access cannula 44 and when the stylet assembly 200 is coupled to the telescoping introducer shaft 60. As best shown in FIGS. 3 and 6A, each one of the plurality of shaft sections 62 is formed of a hollow tubular member extending between a proximal end 64 and a distal end 66. The proximal end 64 of each one of the plurality of shaft sections 62 includes an outwardly projecting proximal ledge 68, while the distal end 66 each one of the plurality of shaft sections 62 includes an inwardly projecting distal ledge 70. The outermost one 62A of the plurality of shaft sections 62 also includes an outwardly projecting distal ledge 72. The telescoping introducer shaft 60 also includes a distal tubular cap 76 coupled to the distal end 66 of the innermost one 62E of the plurality of shaft sections 62 and positioned adjacent to the distal end 66 of each of the additional ones of the plurality of shaft sections 62A-62D in the non-extended position. The distal tubular cap 76 includes a flange portion 78 that is configured to be coupled to the cannula hub portion 46 of the access cannula 44.

Figure 7:
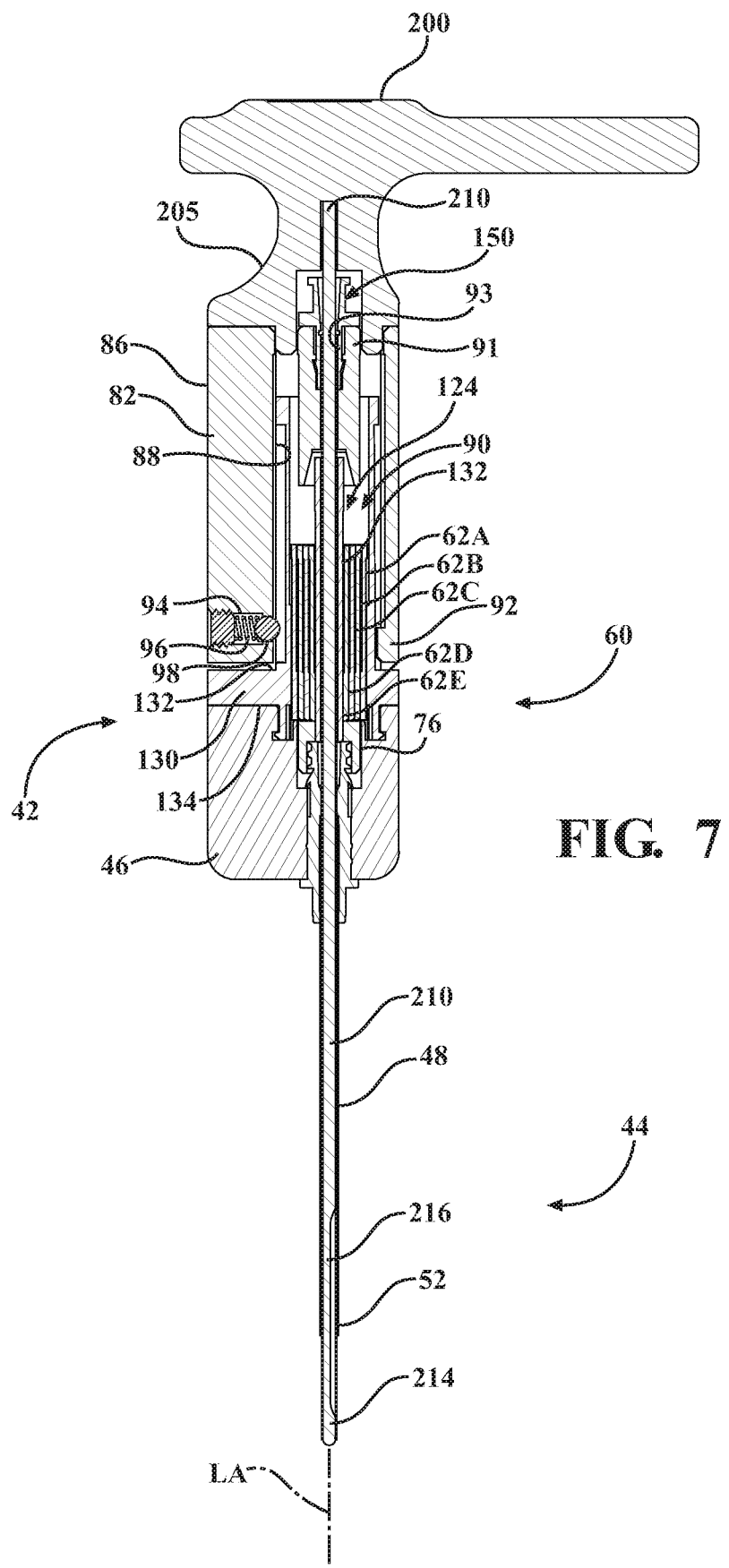
FIG. 7 is a section view of the stylet coupled to and contained within the introducer device of FIG. 4 with the introducer device in the non-extended position and the hub assembly in the supplemental position.
Figure 8:
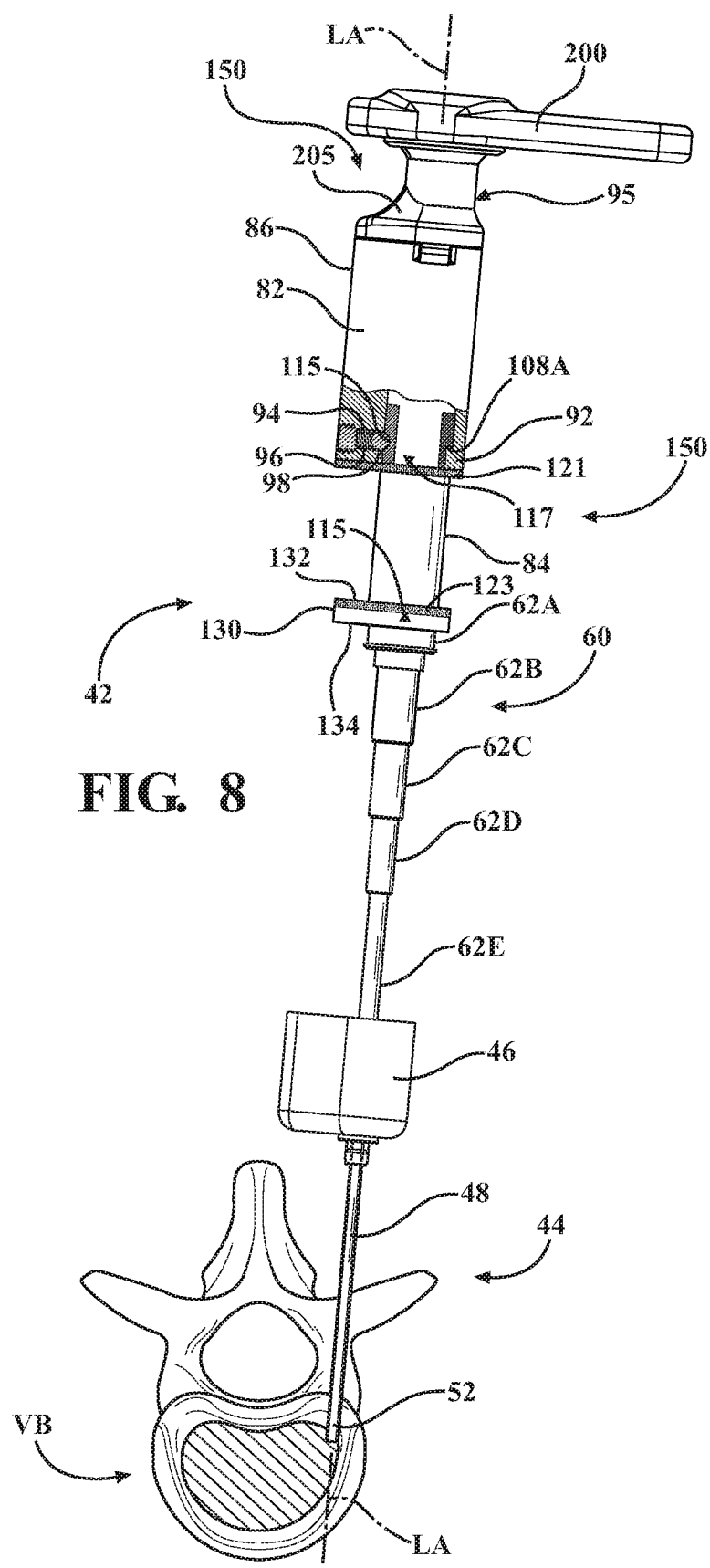
FIG. 8 is a perspective and partial section view of the stylet coupled to and contained within the introducer device which is coupled to the access cannula, with the introducer device in the extended or telescoping position and the hub assembly in the initial and locked position, and with the distal end of the access cannula inserted within the vertebral body.

When in the non-extended position, as shown for example in FIGS. 6 and 7 and best shown in FIG. 6A, each one of the plurality of shaft sections 62 includes wherein the respective proximal ends 64 are aligned with one another in a direction normal to the longitudinal axis LA. In addition, each one of the respective distal ends 66 are also aligned with one another in a direction normal to the longitudinal axis LA and wherein the distal tubular cap 76 is adjacent the distal end 66 of each one of the plurality of shaft sections 62A-62E. In this non-extended position, the inwardly projecting distal ledge 70 of a respective one of the plurality of shaft sections 62 is spaced from and longitudinally aligned with each respective other inwardly projecting distal ledge 70 and with the outwardly projecting distal ledge 72 on the next adjacent inward one of the plurality of shaft sections 62. Conversely, in the extended or telescoping position, as shown in FIGS. 4, 5, and 8, each one of the respective proximal ends 64, and each one of the respective distal ends 66, of the shaft sections 62 are not aligned with one another in a direction normal to the longitudinal axis LA. In this extended or telescoping position, the inwardly projecting distal ledge 70 of a respective one of the plurality of shaft sections 62 is contacting the longitudinally aligned with the outwardly projecting proximal ledge 68 on the next adjacent inward one of the plurality of shaft sections 62.

The hub assembly 80 includes an outer hub 82 and an inner hub 84 moveable along the longitudinal axis relative to and within the outer hub 82 between an initial position (see FIGS. 1, 2, 4, 5, 6, 8, 9, 13) and a supplemental position (see FIGS. 7, 10, 11, 12 and 14) in which the inner hub 84 is moved distally relative to the outer hub 82. The outer hub 82 includes a longitudinally extending outer surface 86 and an opposing longitudinally extending inner surface 88 defining an interior region 90. The longitudinally extending inner surface 88 includes a tab portion 92. The outer hub 82 also includes a semicircular detent channel 94 extending between the longitudinally extending outer surface 86 and inner surface 88. A biasing device 96, shown as a spring 96, and a ball 98 are disposed within the detent channel 94, with the biasing device 96 positioned between the ball 98 and the longitudinally extending outer surface 86. The outer hub 82 also includes a pair of opposing wings 85 extending outwardly from at a position near a proximal end 87.

The proximal end 87 of the outer hub 82 is open, but includes an external coupling device 89 that is sized to receive and couple to with a respective one of the stylet 200, an expandable member assembly or balloon assembly 400 (see FIGS. 12 and 13), and a cement delivery system 500 (see FIG. 14) at various times during the vertebral body augmenting process, as will be described further below. The external coupling device 89, in certain configurations, allows one of the stylet 200, the expandable member assembly 400, and the cement delivery system 500 to be press fit onto the outer hub 82, while in other configurations may include other features that allow the respective one of the stylet 200, the expandable member assembly 400, and the cement delivery system 500 to be coupled in any other manner and retained to the outer hub 82 during use. The proximal end 87 of the outer hub 82 also includes an internal sheath coupling region 91 having an inner surface 93. The inner surface 93 defines a central opening 95 which defines a portion of the proximal end 152 of the lumen 150 of the telescoping introducer shaft 60.

Figure 4A:
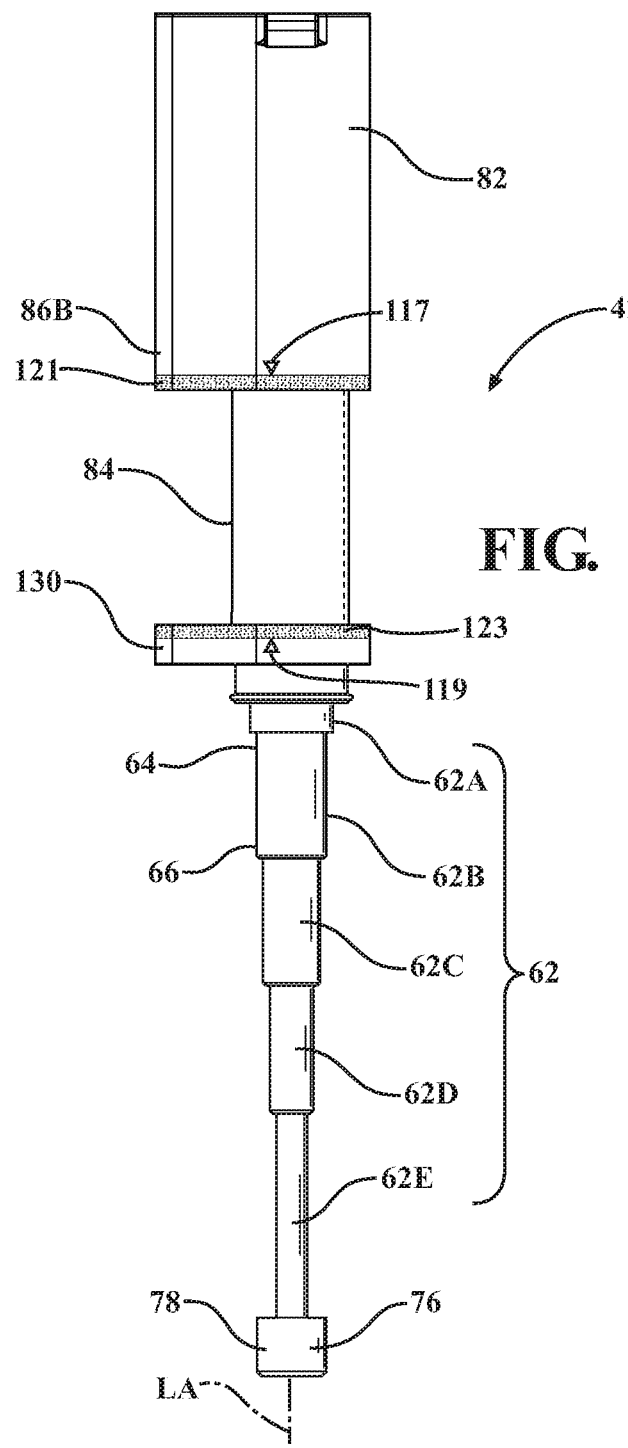
FIG. 4A is a perspective view of the introducer device in the extended or telescoping position and with the hub assembly in the initial position and unlocked position.
Figure 4B:
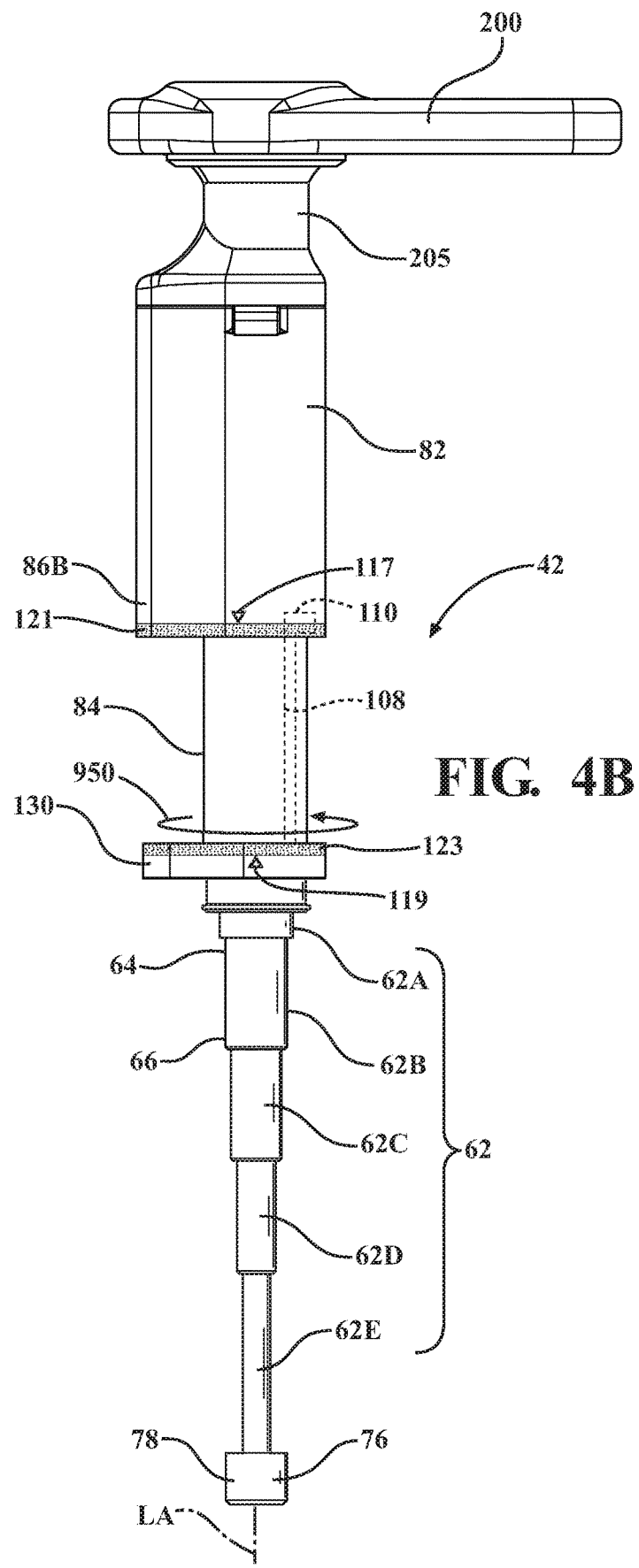
FIG. 4B is a perspective view of the stylet coupled to and contained within the introducer device, with the introducer device in the extended or telescoping position and with the hub assembly in the initial position and locked position.
Figure 5A:
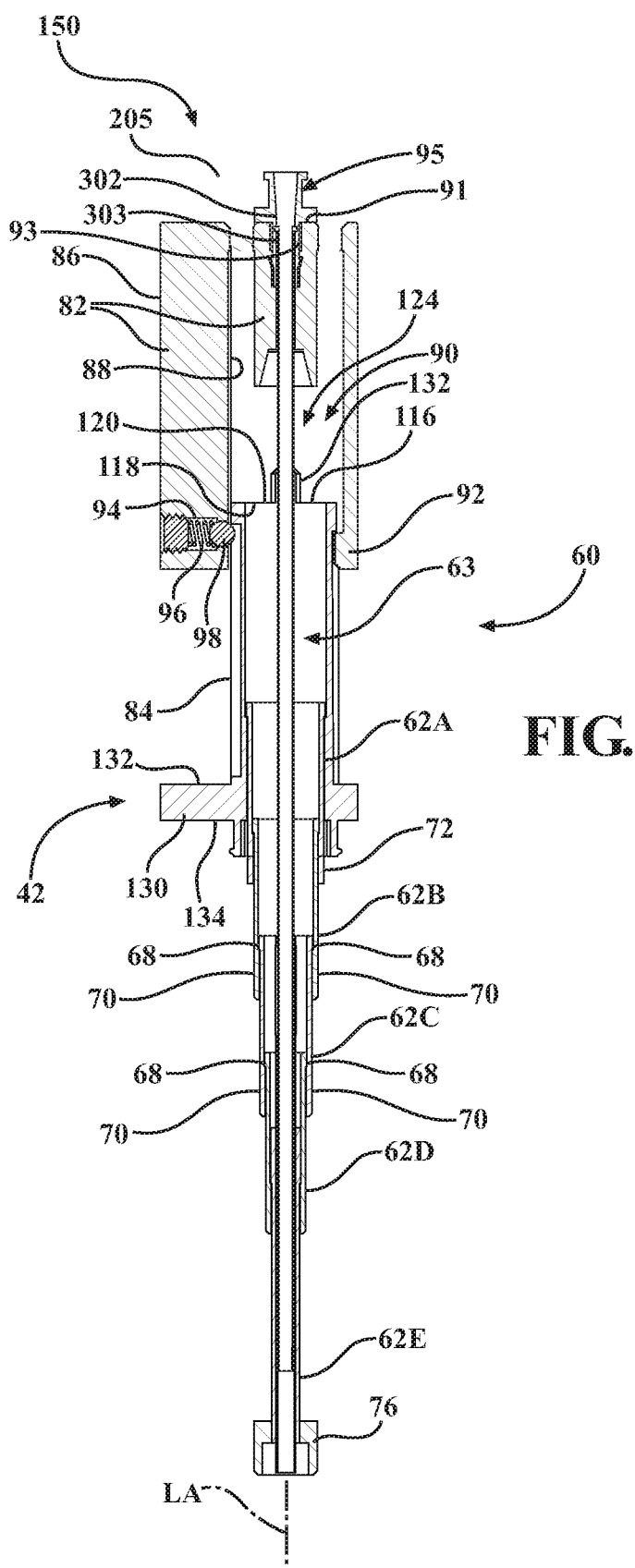
FIG. 5A is a section view of FIG. 4A.

The inner hub 84 has a longitudinally extending outer surface 100 and an opposing longitudinally extending inner surface 140 that defines an inner cavity 142. The longitudinally extending outer surface 100 includes a first channel 102 extending between a distal end 104 and a proximal end 106 configured to receive the tab portion 92 and an opposing second channel 112 distinct from the first channel 102 that is configured to receive the ball 98. The first channel 102 includes a longitudinally extending longitudinal channel portion 108 and a transverse channel portion 110 extending transversely from longitudinally extending longitudinal channel portion 108 at the proximal end 106. The length of the longitudinally extending first channel portion 108, defined between a proximal end 108A and a distal end 108B, is generally equal to the length of the opposing second channel 112, defined between a proximal end 112A and a distal end 112B. The inner hub 84 also includes a proximal ball retention region 115 located transversely and adjacent to, but spaced from, a proximal end 112A of the second channel 112. Accordingly, as the outer hub 82 moves generally longitudinally relative to the inner hub 84, the tab portion 92 generally rides longitudinally along the longitudinal channel portion 108 between the proximal end 108A and the distal end 108B while the ball 98 rides within the second channel 112 between the proximal end 112A and the distal end 112B. When the outer hub 82 is rotated relative to the inner hub 84 in a first rotational direction (shown by arrow 950 in FIGS. 4B and 5B) and when the ball 98 positioned within the second channel 112 at the proximal end 112A (and the tab portion 92 is located at the proximal end 108A—corresponding to the initial and unlocked position as shown in FIGS. 4A and 5A)), The proximal end 106 of the inner hub 84 includes an inwardly extending hub region 116 having an inner surface 118 and an opposing outer surface 120. The inwardly extending hub region 116 terminates into an inner hub surface 122 that connects the inner surface 118 and outer surface 120 and defines a central opening 124. The inner hub surface 122 defines another portion of the proximal end 152 of the lumen 150 (along with the inner surface 93 of the proximal end 87 of the internal sheath coupling region 91 of the outer hub 82) of the telescoping introducer shaft 60. The inner hub surface 122 may include one or more outwardly extending projection portions 125 that are configured to be coupled within slots 207 in the stylet hub 205. The inner surface 93 of the outer hub 82, and the inner hub surface 122 of the inner hub 84, are respectively sized and shaped to receive the stylet shaft 210 therethrough when the stylet 200 is coupled to the introducer device 42. The central openings 95, 124 also perform several additional functions of the vertebral augmentation, for example, providing a pathway for introducing a balloon 406 and/or for the delivery of the curable material from the cement delivery system 500 to the vertebral body.

The distal end 104 of the inner hub 84 includes an outwardly extending ledge 130 having an upper surface 132 and an opposing lower surface 134. The upper surface 132 includes an inwardly extending stepped region 136 and an outwardly extending recessed region 138. The lower surface 134 includes an inwardly extending recessed portion 138 and an outwardly extending stepped portion. The inwardly extending stepped region 136 is configured to be adjacent to the outwardly projecting proximal ledge 68 of the outermost one 62A of the shaft sections 62 when the plurality of shaft sections 62 are in the extended position, as shown in FIG. 4B, and is also configured to be spaced from the outwardly projecting proximal ledge 68 of the outermost one 62A of the shaft sections 62 when the plurality of shaft sections 62 are in the non-extended position, as shown in FIGS. 4A and 4C. The inwardly extending stepped region 136 is configured to be adjacent to the outwardly projecting distal ledge 72 of the outermost one 62A of the shaft sections 62 when the plurality of shaft sections 62 are in the extended position, as shown in FIG. 5, and is also configured to be spaced from the outwardly projecting distal ledge 72 of the outermost one 62A of the shaft sections 62 when the plurality of shaft sections 62 are in the non-extended position, as shown in FIGS. 6 and 7.

The longitudinally extending outer surface 86 of the outer hub 82, and an outer surface 133 of the outwardly extending ledge 130, each include a respective pair of indicia that are visible by the practitioner/surgeon and are used to aid determine whether hub assembly 80 is in the initial or supplemental position, and if the initial position whether the hub assembly 80 is also in the unlocked or locked position. In particular, the longitudinally extending outer surface 86 of the outer hub 82 includes a first indicia 117 (shown as a downward pointing triangular shaped indicia 117) and a second indicia 121 (shown as a band or ring-shaped outer hub indicia 121) located at distal end 86B of the longitudinally extending outer surface 86 of the outer hub 82. In addition, the outer surface 133 of the ledge 130 includes a third indicia 119 (shown as an upward pointing triangular shaped indicia 119) and a fourth indicia 123 (shown as a band or ring-shaped ledge portion indicia 123).

The outwardly extending recessed region 138 of the inner hub 84 is configured to be adjacent to a distal end of the hub assembly 80 is in the supplemental position (i.e., the outer hub 82 is moved distally towards the access cannula 44 relative to the inner hub 84 when the introducer device 42 is coupled to the access cannula 44 such that the second and fourth indicia 121, 123 be adjacent to one another) and is configured to be spaced from the distal end of the hub assembly 80 is in the initial position (i.e., the outer hub 82 is moved proximally away from the access cannula 44 relative to the inner hub 84 such that the second and fourth indicia 121, 123 are spaced from one another when the introducer device 42 relative to the supplemental position is coupled to the access cannula 44).

While in the initial position, the hub assembly 80 can also be moved to a locked position (see FIGS. 4B and 5B) from an unlocked position (see FIGS. 4A and 5A) by rotating the outer hub 82 relative to the inner hub 84 about the longitudinal axis LA in a first rotational direction (the rotation in the first rotational is shown by arrow 950 also shown in FIG. 4A). During the rotational movement to the locked position, the tab portion 92 of the outer hub 82 rides transversely along the transverse channel portion 110 of the first channel 102 and away from the first channel portion 108. At the same time, the ball 98 is displaced from the proximal end 112A of the second channel 112 and compresses the spring 96 within the detent channel 94 opposite the longitudinally extending outer surface 100 of the inner hub 84 until such time as it enters and is seated within the proximal ball retention region 115 to accommodate this transverse movement, with the spring 96 being decompressed to position the ball 98 within the proximal ball retention region 115. In the locked position, the outer hub 82 is prevented from moving longitudinally relative to the inner hub 84 by the tab portion 92 contacting the second channel portion 110. Accordingly, to move the outer hub 82 longitudinally relative to the inner hub 84, the practitioner/surgeon must first rotate the outer hub 82 in a second rotational direction opposite the first rotational direction relative to the locking movement to move the tab portion 92 transversely along the transverse channel portion 110 towards the first channel portion 108, and wherein the ball 98 is unseated from the proximal ball retention region 115 and moves along the longitudinally extending outer surface 100 until such time that it is brought back into position within the second channel 112. As a visual cue to confirm the positioning of the hub assembly 80 in the initial and locked position, the practitioner/surface may visually confirm that the first and third indicia 117, 119 are not in longitudinal alignment with one another (i.e., by confirming that the point of the downward pointing triangular shaped indicia 117 is offset along the longitudinal axis from the point of the upward pointing triangular shaped indicia 119).

As noted above, the introducer device 42 also includes a sheath 300 that overlies the shaft 210 of the stylet 200 when the stylet 200 is coupled to the introducer device 42. The sheath 300 provides a further pathway extending from the central opening 124 for positioning of a balloon 406 and/or for the delivery of the curable material from the cement delivery system 500 to the vertebral body. The sheath 300 includes a proximal end hub portion 302 positioned adjacent to internal sheath coupling region 91 of the outer hub 82. The proximal end hub portion 302 is coupled to the proximal end 303 of the sheath 300. The sheath 300 also includes a distal end 304 opposite the proximal end 303 configured to be positioned at or near the distal end 214 of the shaft 210 of the stylet 200. The sheath 300 may be tubular in shape and define a lumen 306 sized to slidably and snugly receive the shaft 210, with the lumen 306 also being sized to correspond generally to the size of the central opening 124. A length of the sheath 300 defined between the proximal and distal ends 303, 304 may be sufficient for the sheath 300 to extend through and be operable beyond the distal end 52 of the access cannula 44 when the hub assembly 80 is in the supplemental position, as shown in FIG. 4C.

The sheath 300 is flexible and configured to conform to the shaft 210. The sheath 300 may be formed from a flexible biocompatible polymer having sufficient hoop strength such that the lumen 306 remains patent upon removal of the shaft 210 of the stylet from the sheath 300. Suitable flexible polymers include polypropylene, polyether ether ketone (PEEK), and the like. The sheath 300 may be formed from a flexible biocompatible metal, composite, and combinations thereof, with or without reinforcing features such as filament windings or braids. At least a distal end 304 of the sheath 300 is configured to conform to the distal end 214 of the shaft 210 as the pre-set curve is in the constrained state for insertion of the distal end 214 and the distal end 304 of the sheath 300 through the lumen 75 of the access cannula 44 to within the vertebral body, and further configured to conform to the distal end 214 of the shaft 210 as the pre-set curve is moved from the constrained state to the unconstrained state. FIG. 1 shows the pre-set curve in the unconstrained state with the distal end 304 of the sheath 300 conforming to the distal end 214 of the shaft 210.

A workflow of performing a vertebral augmentation with the system 40 (i.e., a method for stabilizing a vertebral body) will now be described with particular reference to FIGS. 2-14. The vertebra with the offending vertebral body may be confirmed on fluoroscopic imaging. An incision may be made in the overlying paraspinal musculature lateral of midline generally in alignment with one of the pedicles of the vertebra.

The method begins by positioning the distal end 58 of the access cannula 44 within the vertebral body such that a lumen 75 of the access cannula 44 provides access to an interior of the vertebral body along the longitudinal axis LA. The distal end 58 of the access cannula 44, with the trocar disposed therein, is then directed through the pedicle a position beyond the cortical rim and within the interior region of the vertebral body, and the trocar is removed. The access cannula 44 provides the working channel to within the interior region of the vertebral body along the longitudinal axis LA. The cannula hub portion 46 is exposed and configured to be engaged by the introducer device 42.

The method continues wherein the introducer device 42 and the stylet 200 are first provided in an uncoupled state, and continues with the step of coupling the stylet 200 within the introducer device 42 such that stylet shaft 210 of the stylet 200 is contained within the internal bore 63 of the introducer device 42 with the telescoping introducer shaft 60 is in the extended position, or telescoping position, while the hub assembly 80 is in the initial position. In particular prior to inserting the stylet 200, the hub assembly 80 of the introducer device 42 is first placed in the extended position or telescoping position while also remaining in the initial and unlocked position, as shown in FIGS. 4A and 5A and as described above. As noted above, in the extended or telescoping position, the inwardly projecting distal ledge 70 of a respective one of the plurality of shaft sections 62 is contacting the outwardly projecting distal ledge 72 on the next adjacent inward one of the plurality of shaft sections 62. In addition, while the proximal tubular cap 74 remains connected to the outermost one 62A of the plurality of shaft sections 62, the proximal tubular cap 74 is spaced from the proximal end 64 of each of the additional ones of the plurality of shaft sections 62B-62E. Still further, while the distal tubular cap 76 remains connected to the innermost one 62E of the plurality of shaft sections 62, the proximal tubular cap 74 is spaced from the distal end 66 of each of the additional ones of the plurality of shaft sections 62A-62D.

In addition, and as also described above, when the hub assembly 80 of the introducer device 42 is in the initial and unlocked position, the ball 98 is positioned at the proximal end 108A within the second channel 108, while the tab portion 92 is positioned at the proximal end 112A of the first channel 112, The practitioner/surgeon may confirm that the hub assembly 80 is in the initial position by visually confirming the spaced relationship of the second indicia 121 and fourth indicia 123. In addition, practitioner/surgeon may visually confirm that the hub assembly 80 is in the unlocked position by visually confirming alignment of the first indicia 117 and second indicia 119 along the longitudinal axis.

Figure 5B:
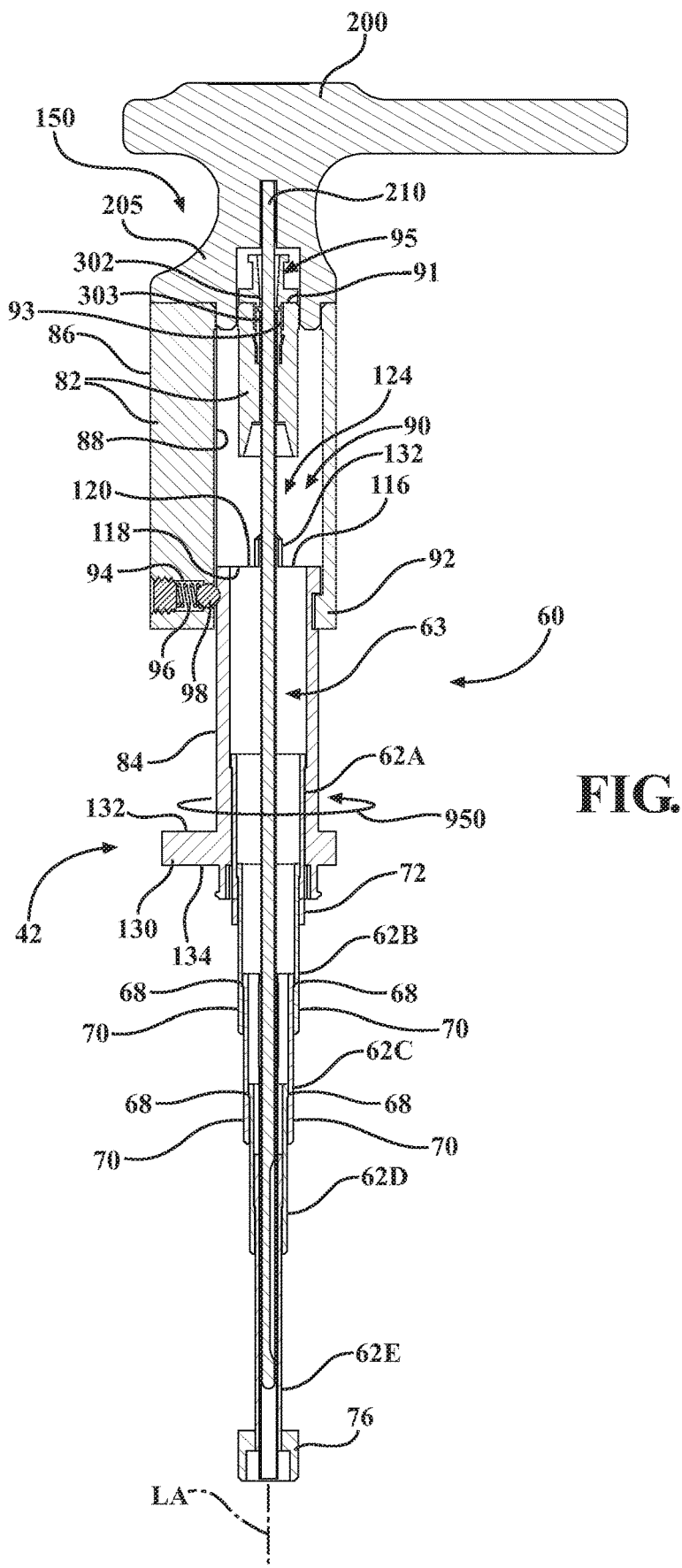
FIG. 5B is a section view of FIG. 4B.

Next, as shown in FIGS. 4B and 5B, the hub assembly 80 is moved from the unlocked position to the locked position, while maintaining the hub assembly 80 in the initial position. In particular, the outer hub 82 is rotated relative to the inner hub 84 in the first rotational direction, shown by arrow 950. During the rotational movement to the locked position, as also noted above, the tab portion 92 of the outer hub 82 rides transversely along the transverse channel portion 110 of the first channel 102 and away from the first channel portion 108. At the same time, the ball 98 is displaced from the proximal end 112A of the second channel 112 and compresses the spring 96 within the detent channel 94 opposite the longitudinally extending outer surface 100 of the inner hub 84 until such time as it enters and is seated within the proximal ball retention region 115 to accommodate this transverse movement, with the spring 96 being decompressed to position the ball 98 within the proximal ball retention region 115. In the locked position, the outer hub 82 is prevented from moving longitudinally relative to the inner hub 84 by the tab portion 92 contacting the second channel portion 110. The user/practitioner can confirm that the hub assembly 80 is in the locked position by visually confirming non-alignment of the first indicia 117 and second indicia 119 along the longitudinal axis.

Next, the stylet 200 is coupled to the introducer device 42 while the hub assembly 80 is in the initial and locked position and while the telescoping introducer shaft 60 is in the extended or telescoping position. In particular, the practitioner/surgeon introduces the distal end 214 of the stylet shaft 210 within the central opening 95 at the proximal end 87 and within the proximal end 152 of the lumen 150. To aid in applying force distally on the stylet 200 to move the stylet shaft 210 towards the shaft sections 62 during the insertion process, the practitioner/surgeon may grasps the wings 85 with his fingers to apply a counter force in a proximal direction to the distal force applied by the practitioner/surgeon's thumb. Alternatively, the user may grasp the wings 85 while tapping the top surface of the stylet hub 205 with a hammer or other instrument. The process continues until the stylet hub 205 is received onto the external coupling device 89, such as being press fit onto the external coupling device 89, completing the coupling process. The movement of the distal end 214 of the stylet shaft 210 into the sheath 300 moves the sheath 300 in conjunction therewith. Because the telescoping introducer shaft 60 is in the extended or telescoping position, the entirety of the stylet shaft 210 and sheath 300 are retained within the internal bore 63 of the introducer device 42, with the flexible distal portion 216 of the stylet shaft 210 in the constrained state (i.e., generally straight as shown in FIG. 5B)

Next, as shown in FIG. 8, the introducer device 42 is coupled to the access cannula 44 with the telescoping introducer shaft 60 in the extended position and the hub assembly 80 in the initial position and locked position. In particular, the distal tubular cap 76 of the introducer device 42 is engaged with the cannula hub portion 46 such that the lumen 75 of the cannula shaft 48 is aligned with the lumen 150 of the telescoping introducer shaft 60.

Figure 9:
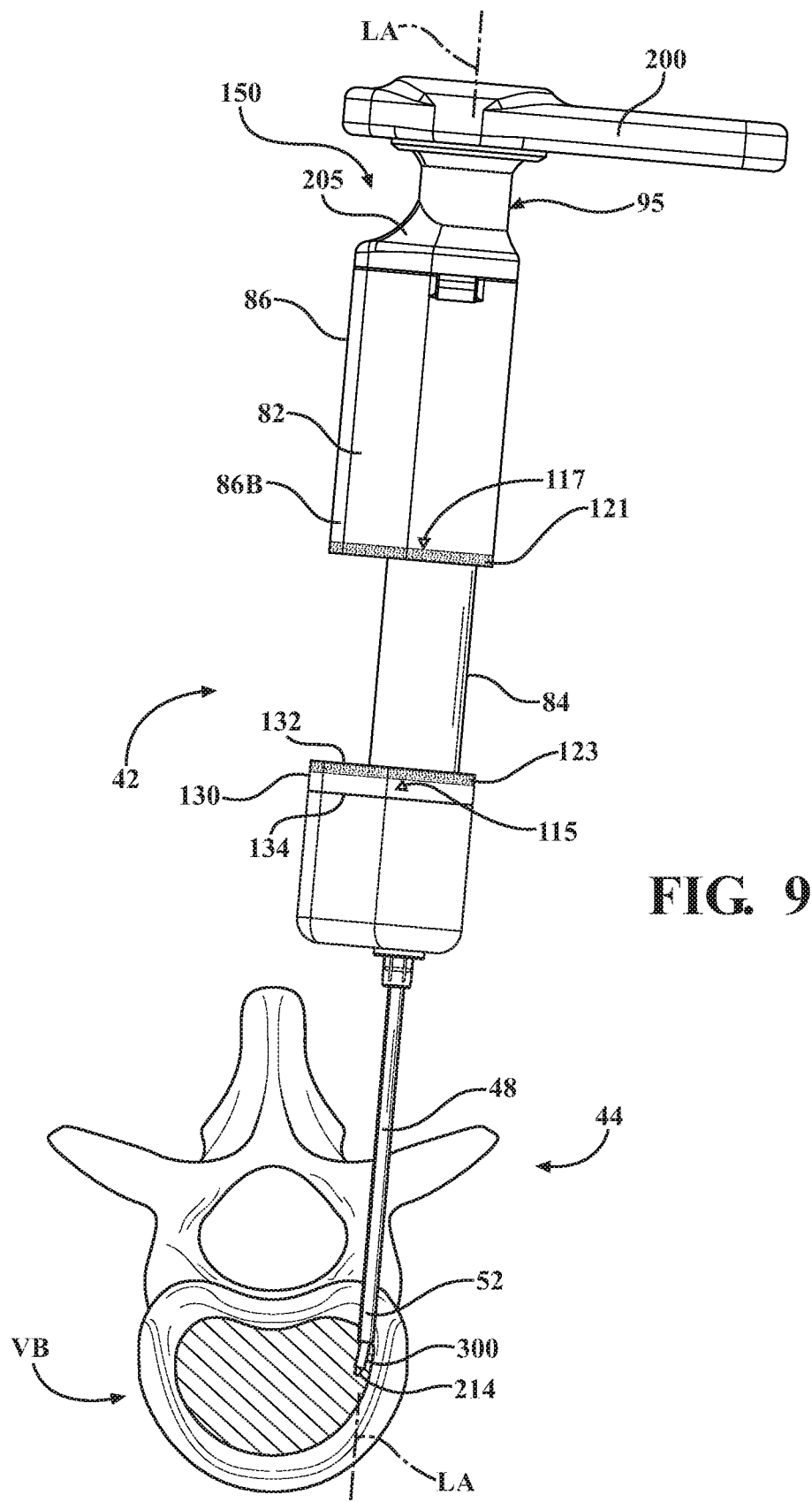
FIG. 9 is a perspective and partial section view of the stylet coupled to and contained within the introducer device which is coupled to the access cannula, with the introducer device in the non-extended position and the hub assembly in the initial position and unlocked position, and with the distal end of the access cannula inserted within the vertebral body.

Next, after the coupling of the introducer device 42 to the access cannula 44, the telescoping introducer shaft 60 is moved from the extended and telescoping position (i.e., the shaft sections 62 of the telescoping introducer shaft 60 are collapsed), as shown in FIG. 8, to the non-extended position (i.e., collapsed position) as shown in FIG. 9. The collapsing of the shaft sections 62 results in the distal end 214, 304 of the stylet shaft 210 and flexible sheath 300, respectively, moving from the internal bore 63 to within the lumen 75 of the cannula shaft 48, but wherein the flexible distal portion 216 remains in the constrained state within the cannula shaft 48. In particular, the distal end 214 of the stylet shaft 210 is brought into registration with the distal end 52 of the access cannula 44. Notably, the collapsing does not, however, bring the distal end 214 of the stylet shaft 210 in penetration within the vertebral body, which prevents damage to the vertebral body associated with the collapsing movement.

The introduction of the stylet shaft 210 and flexible sheath 300 within the lumen 75 through the collapsing of the shaft sections 62 does not require manual manipulation of the distal end 214 of the stylet shaft 210, and in particular and the flexible distal portion 216 of the distal end 214, in order to introduce the stylet shaft within the lumen 75 of the access cannula 44. This offers a significant advantage over conventional introducer devices and stylets utilized in the unipedicular approach, which typically requires such manual manipulations.

After collapsing the shaft sections 62, the hub assembly 80 is then moved from the initial and locked position (as shown in FIG. 8 prior to collapsing of the shaft sections 62) to the initial and unlocked position (as shown in FIG. 9 after the collapsing of the shaft sections 62). In particular, to the outer hub 82 is rotated relative to the inner hub 84 in the second rotational direction opposite the first rotational direction (i.e., opposite the rotational direction shown by arrow 950 in FIGS. 4 and 5). During the rotational movement to the unlocked position, as also noted above, the tab portion 92 of the outer hub 82 rides transversely along the transverse channel portion 110 of the first channel 102 towards the first channel portion 108. At the same time, the ball 98 is displaced from the proximal ball retention region 115, which compresses the spring 96 within the detent channel 94 opposite the longitudinally extending outer surface 100 of the inner hub 84 until such time as it enters and is seated within the proximal end 212 of the second channel 112, with the spring 96 being decompressed to position the ball 98 within proximal end 212 of the second channel 112. Alternatively, the hub assembly 80 may be moved from the initial and locked position to the initial and unlocked position prior to the collapsing of the shaft sections 62, although it is preferable to maintain the hub assembly 80 in the locked position to prevent premature introduction of the stylet shaft 210 and sheath within the vertebral body.

Figure 10:
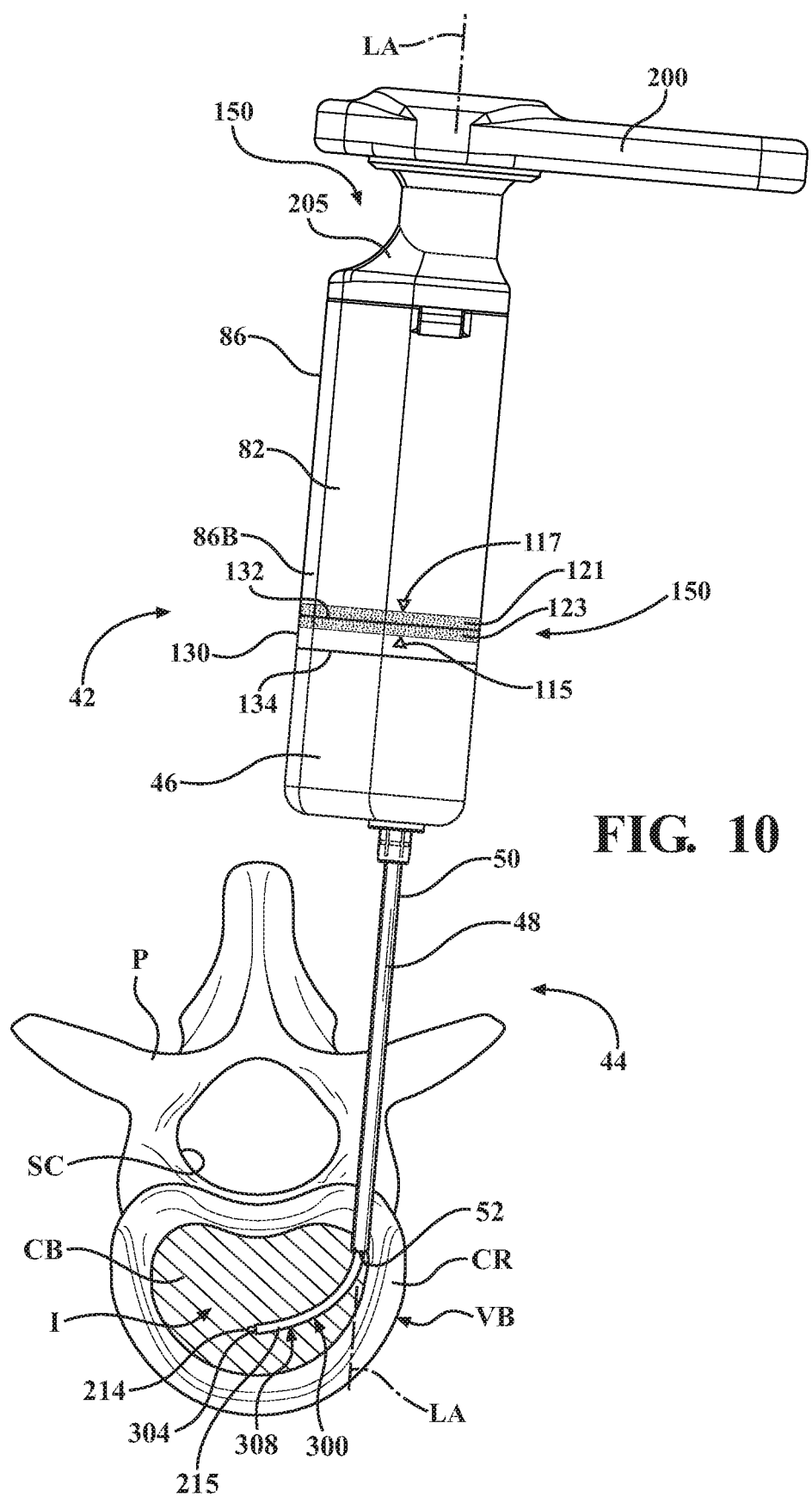
FIG. 10 is a perspective and partial section view of the stylet coupled to and contained within the introducer device which is coupled to the access cannula, with the introducer device in the non-extended position and the hub assembly in the supplemental position, and with the distal end of the access cannula inserted within the vertebral body.
Figure 11:
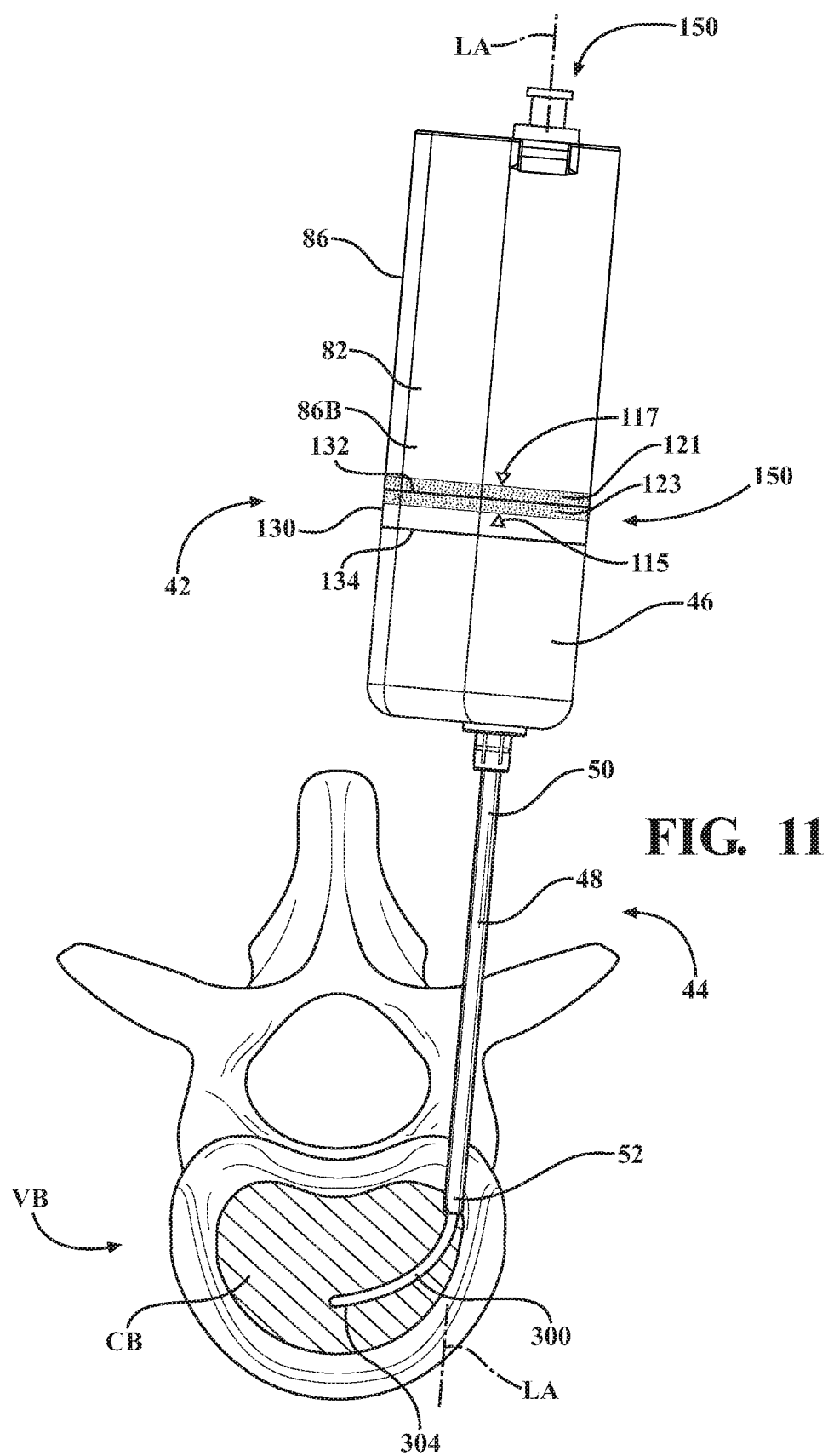
FIG. 11 is a perspective and partial section view of FIG. 10 with the stylet removed, with the introducer device in the non-extended position and the hub assembly in the supplemental, and with the distal end of the access cannula inserted within the vertebral body.

Next, the hub assembly 80 is moved from the initial position and unlocked position, as shown in FIG. 9, to the supplemental position, as shown in FIG. 10. In particular, while in the initial and unlocked position, the outer hub 82 is moved distally in a direction towards the access cannula 44 relative to the stationary inner hub 84, which results in the corresponding distal movement of the sheath 300 coupled within the outer hub 82 and the stylet 200 (and stylet shaft 210) coupled to the outer hub 82. During this movement, the tab portion 92 rides along the longitudinally extending first channel portion 110 of the first channel 108 towards the distal end 108B. At the same time, the ball 98 rides along the second channel 112 towards the distal end 112B. This results in the distal end 214, 304 of the stylet shaft 210 and flexible sheath 300, respectively, moving beyond the distal end 52 of the access cannula 44 to within the target site in the vertebral body offset from the longitudinal axis LA, wherein the flexible distal portion 216 moving from the constrained state to the unconstrained state (see FIG. 10) to displace cancellous bone (CB) within the target site of the vertebral body target.

Next, the method continues by removing the stylet 200 from the introducer device 42 while hub assembly 80 is in the supplemental position and with the telescoping introducer shaft 60 in the non-extended position. In particular, the stylet 200 is uncoupled from the outer hub 82 and pulled in a direction away from the introducer device 42, resulting in the shaft 210 being retracted through the lumen 75 of the cannula shaft 48 and through the lumen 150 of the telescoping introducer shaft 60 until the distal end 214 exits from the central opening 124. During this step, the distal end 304 of the flexible sheath 300 remaining positioned at the target site offset from the longitudinal axis LA.

Figures 12, 12A:
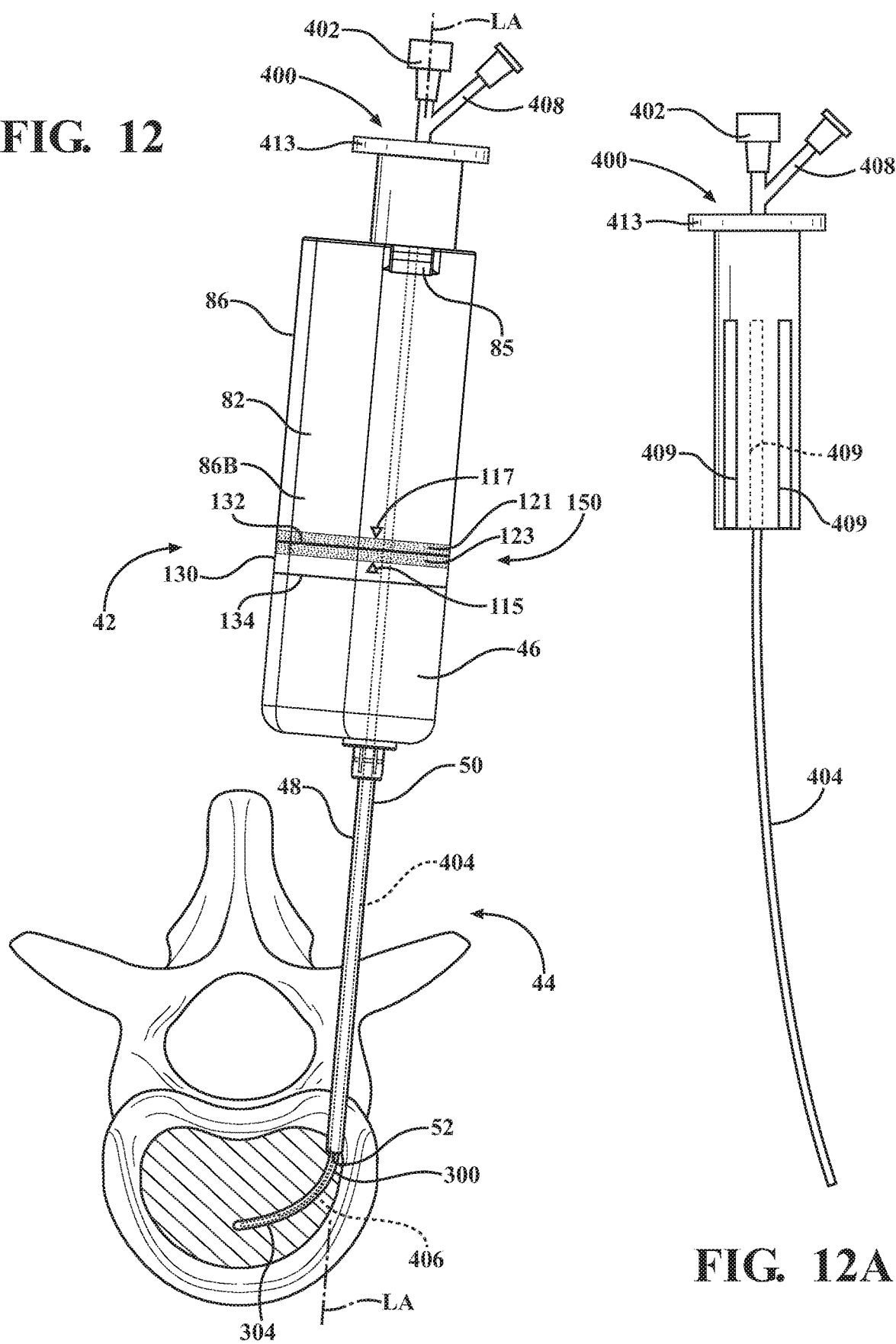
FIG. 12 is a perspective and partial section view of FIG. 11 with a balloon assembly coupled to the introducer device, with the introducer device in the non-extended position and the hub assembly in the supplemental position, and with the balloon in a deflated state.
FIG. 12A is a perspective view of an alternative balloon assembly from the balloon assembly of FIG. 11 that can be used with the introducer device.

Next, the balloon assembly 400, shown in FIG. 12, is coupled onto the introducer device 42 while the hub assembly 80 remains in the supplemental position. Referring now to FIGS. 12 and 12A, the balloon assembly 400 includes a balloon hub 402, the balloon tube 404, and a balloon 406 (shown in FIG. 12 only). The balloon tube 404 extends from the balloon hub 402, and the balloon 406 is disposed at a distal end of the balloon tube 404. The balloon hub 402 includes a fitting, or inflation port 408, adapted to be coupled with a fluid line in communication with a source of incompressible fluid (not shown), for example, air. The hub 402 also includes a keyed region 409 that is inserted within the bore 63 of the inner hub 84 of the introducer device 42 that aides the practitioner/surgeon in the unsheathing of the balloon 406 after introduction into the vertebral body VB to facilitate fine adjustment of balloon 406 placement in the vertebral body VB. The balloon 406 is configured to receive fluid from the source of fluid through the balloon hub 402 and the balloon tube 404 to be moved between a deflated state and an inflated state having a volume greater than the deflated state. In the deflated state, the balloon 406 and the balloon tube 404 are sized to be slidably inserted or directed through the lumen 306 of the sheath 300. The balloon tube 404 may include a length sufficient for the balloon 406 to extend beyond the distal end 304 of the sheath 300 and within the interior region of the vertebral body. The balloon 406 is moved to the inflated state to compress or otherwise displace cancellous bone within the vertebral body at the target site. Returning the balloon 406 to the deflated state may result in a cavity being formed within the cancellous bone for delivery of the curable material from the cement delivery system 500. The hub 402 also may include a thumb target ledge portion 413 located adjacent to the inflation port 408 that provides a place for the practitioner/surgeon's thumb during the balloon insertion and inflation process.

The balloon tube 404 and/or the balloon 406 are sufficiently flexible to follow the pathway defined by the lumen 306 of the sheath 300, including the distal end 304 in the curved configuration. In other words, directing the balloon 406 through the sheath 300 should not alter the curvature of the distal end 304 of the sheath 300. Owing to the flexibility of the balloon tube 404 and/or the balloon 406, the expandable member assembly 400 may lack sufficient columnar strength to be advanced beyond the distal end 304 of the sheath 300 to penetrate the cancellous bone of the interior region. Additionally or alternatively, urging the expandable member assembly 400 to penetrate the cancellous bone may result in the trabeculae of the cancellous bone causing the balloon 406 to deviate from the desired path previously created by the introducer device 42 and/or the target site previously accessed by the introducer device 42. The system 40 of the present disclosure advantageously provides for moving the sheath 300 relative to the expandable member assembly 400 to unsheathe and sheathe the balloon 406.

With the balloon hub 402 engaging the coupling region 89 of the outer hub 82 and with the hub assembly 80 in the supplemental position, the balloon tube 404 may extend through, in sequence, the central opening 124, the lumen 150 and bore 63 of the introducer device 42, the lumen 306 of the sheath 300 extending through the bore of the cannula hub portion 46 and the lumen 75 of the cannula shaft 48. With the hub assembly 80 in the supplemental position, a distal end 410 of the balloon 406 is near or in registration with the distal end 304 of the sheath 300, as shown in FIG. 12. The balloon 406 is in the deflated state and sheathed within the distal end 304 of the sheath 300 in the curved configuration.

Figure 13:
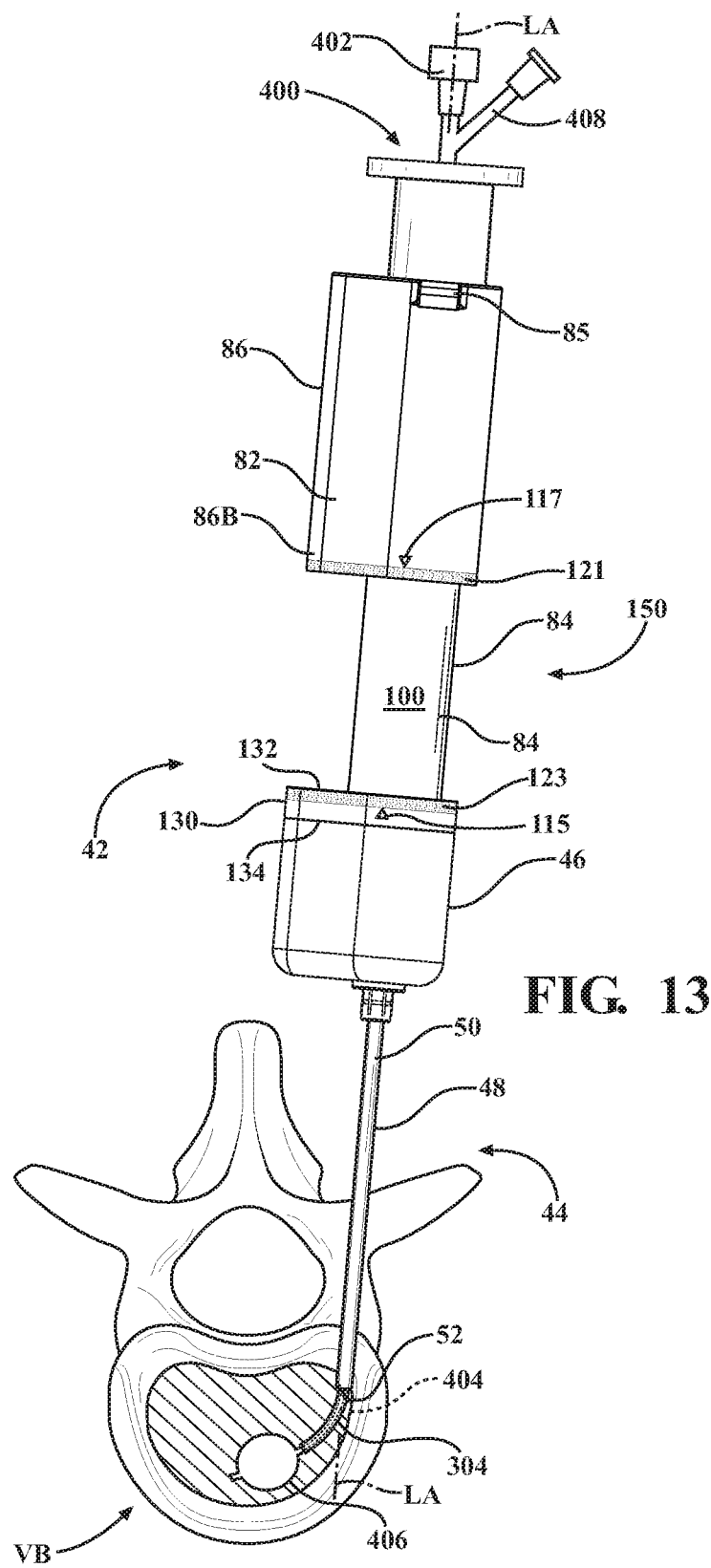
FIG. 13 is a perspective and partial section view of FIG. 11 with a balloon assembly coupled to the introducer device, with the introducer device in the non-extended position and the hub assembly in the initial and unlocked position, and with the balloon in an inflated state

After the balloon 406 is positioned near or in registration with the distal end 304 of the sheath 300 in the deflated state, the balloon 406 may be unsheathed by moving the hub assembly 80 from the supplemental position towards the initial position such that the balloon 406 extends beyond the distal end 304 of the sheath 300 and within the target area of the vertebral body, as shown in FIG. 13. In particular, the outer hub 82 is moved proximally relative to the inner hub 84. As noted above, the outer hub 82 includes wings 85 extending laterally from the longitudinally extending outer surface 86 for receiving the input from the practitioner. FIG. 1 best shows the wings 85 being arcuate in shape and mirrored relative to one another with each of the wings 85 configured to ergonomically be engaged by one or more fingers of the practitioner. In one example, one of the wings 85 is engaged by the index finger of the practitioner, and the other one of the wings 85 is engaged by the middle finger of the practitioner. In at least some respects the ergonomics are similar to the flanges of a barrel of a medical syringe. The outer hub 82 may be moved a desired distance, and/or a set distance to the initial position. The set distance may correspond to at least the distance required to unsheathe the balloon 406 based on its length. With continued reference to FIG. 13, the proximal movement of the outer hub 82 results in proximal movement of the sheath 300 coupled to the outer hub 82 with such movement being relative to the expandable member assembly 400 remaining in a static position. The balloon 406 is unsheathed and exposed within the interior region of the vertebral body in the deflated state, after which the balloon 406 may be moved to the inflated state to displace the cancellous bone. As noted above, the keyed region 409 of the hub 402 may facilitate fine adjustment of the placement of the balloon 406 in the vertebral body VB after the movement of the hub assembly towards the initial position.

After the deflated balloon 406 is unsheathed by moving the outer hub 82 to the initial position, the balloon 406 may then be inflated by introducing fluid from the source of fluid through the balloon hub 402 and the balloon tube 404, as shown in FIG. 13. The inflated balloon 406 displaces cancellous bone within the vertebral cavity. With the balloon 406 in the inflated state, the balloon 406 is returned to the deflated state to form the cavity 420 within the cancellous bone for delivery of the curable material (see FIG. 14). The balloon 406 is then removed by moving the balloon 406 into and through the sheath 300. This movement may be associated with undesirable interference at the distal end 304 of the sheath 300. The retraction of the balloon 406 into the aperture at the distal end 304 may result in component compromise (e.g., galling), and/or the forces on the distal end 304 of the sheath 300 may cause the sheath 300 deviate from its existing path or curvature. The subsequent delivery of the curable material may not be properly located with the formed cavity.

As a result, the present system 40 may advantageously provide for sheathing the balloon 406 prior to withdrawal by moving the hub assembly 80 back to the supplemental position prior to withdrawing the balloon 406. Any resistance may be felt by the practitioner/surgeon, which can be gradually addressed through further deflation of the balloon 406 and urging of the hub assembly 80 from the initial position by moving the outer hub 82 distally relative to the inner hub 84. The balloon 406 is sheathed within the distal portion 212 of the sheath 300, after which the balloon assembly 400 can be confidently removed from the introducer device 42.

Figure 14:
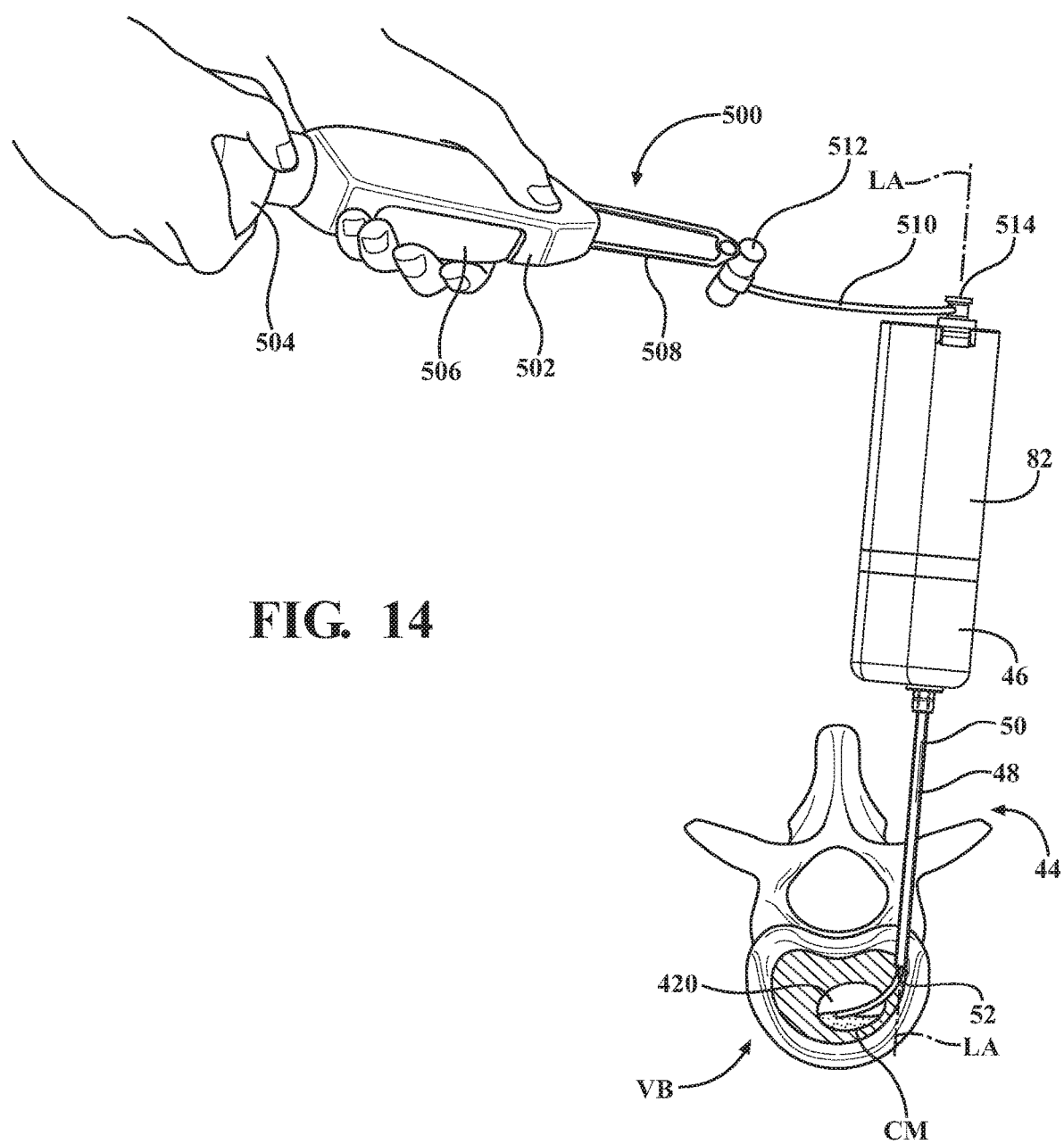
FIG. 14 is a perspective and partial section view of FIG. 11 with a bone cement delivery device coupled to the introducer device, with the introducer device in the non-extended position and the hub assembly in the supplemental position, and with the bone delivery device delivering a curable material to the vertebral body.
Figure 15:
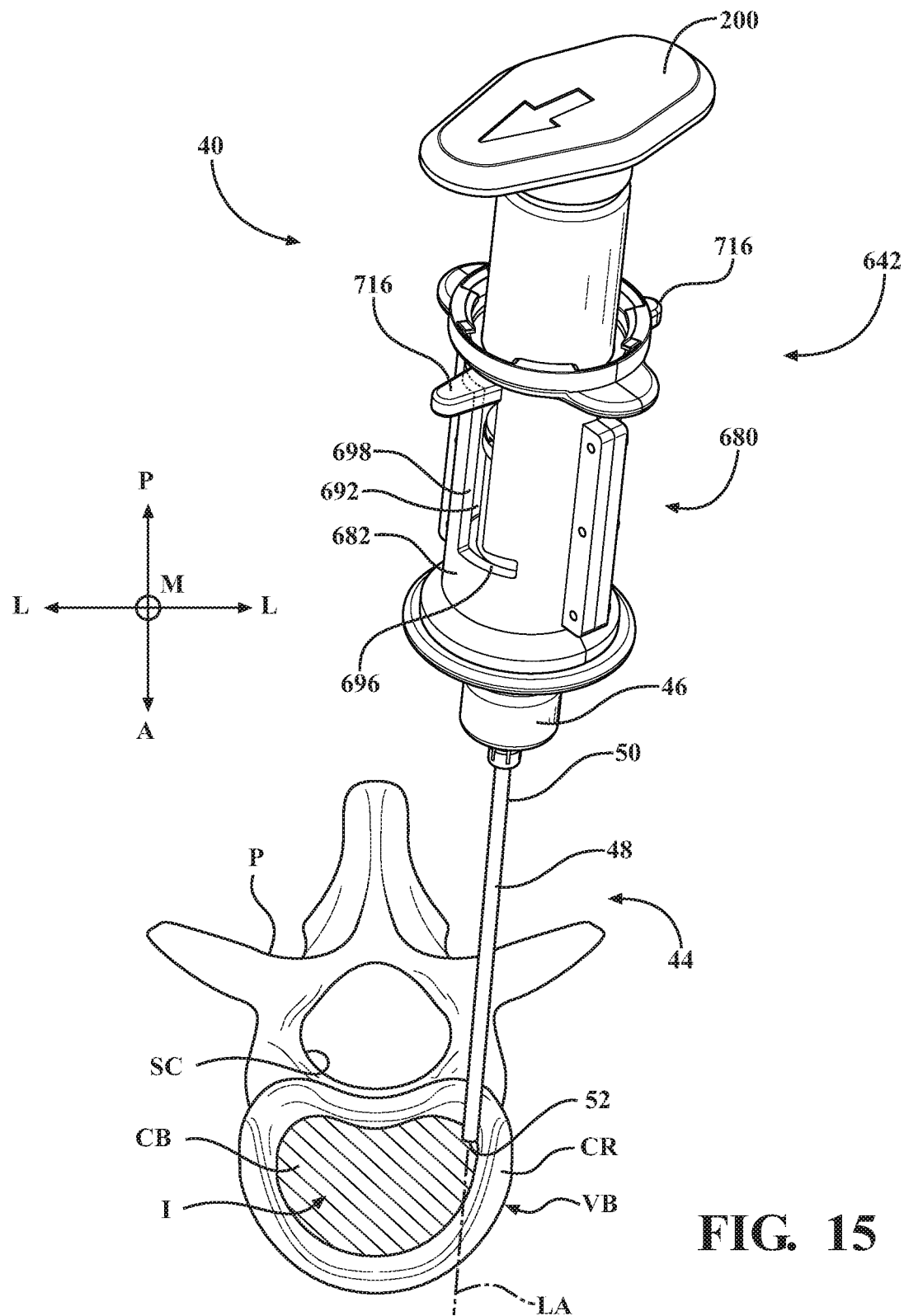
FIG. 15 shows a system for augmenting a vertebral body including a stylet, an alternative telescoping introducer device from the telescoping introducer device of FIGS. 1-14, and an access cannula, with the stylet coupled to and contained within the introducer device which is coupled to the access cannula, with the introducer device in the non-extended position and the hub assembly in the initial position, and with the distal end of the access cannula inserted within the vertebral body.
Figure 16:
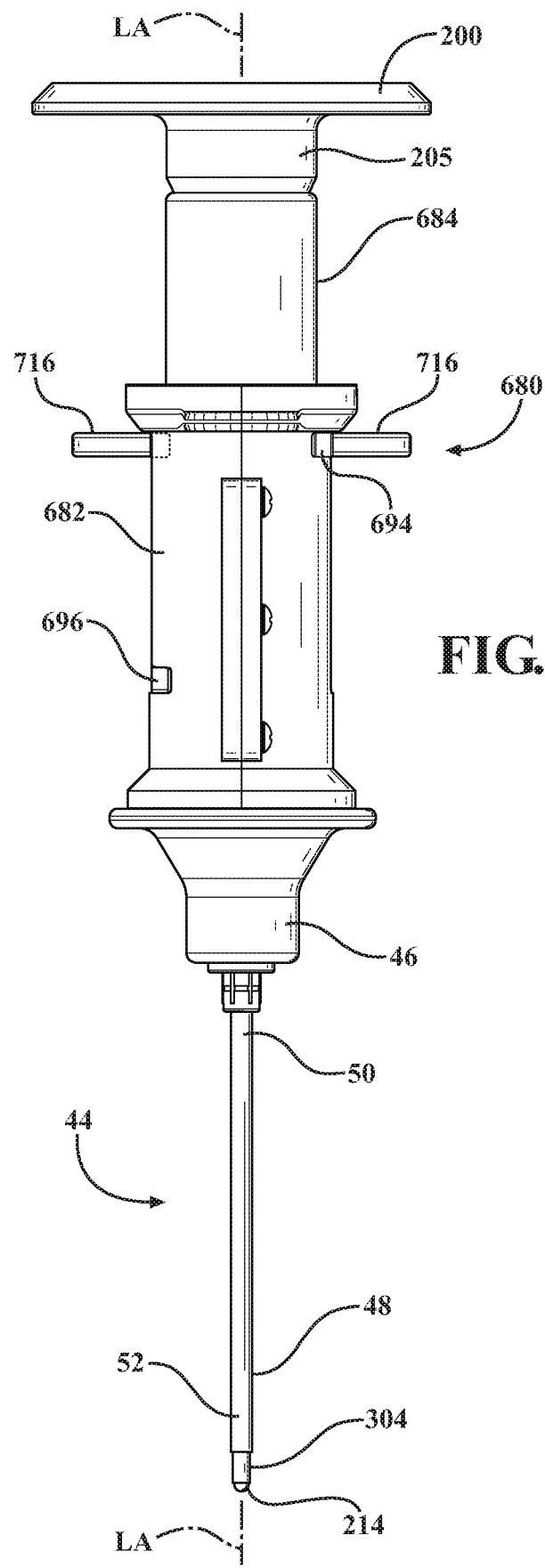
FIG. 16 is a side perspective view of the system of FIG. 15 without the vertebral body.
Figure 17:
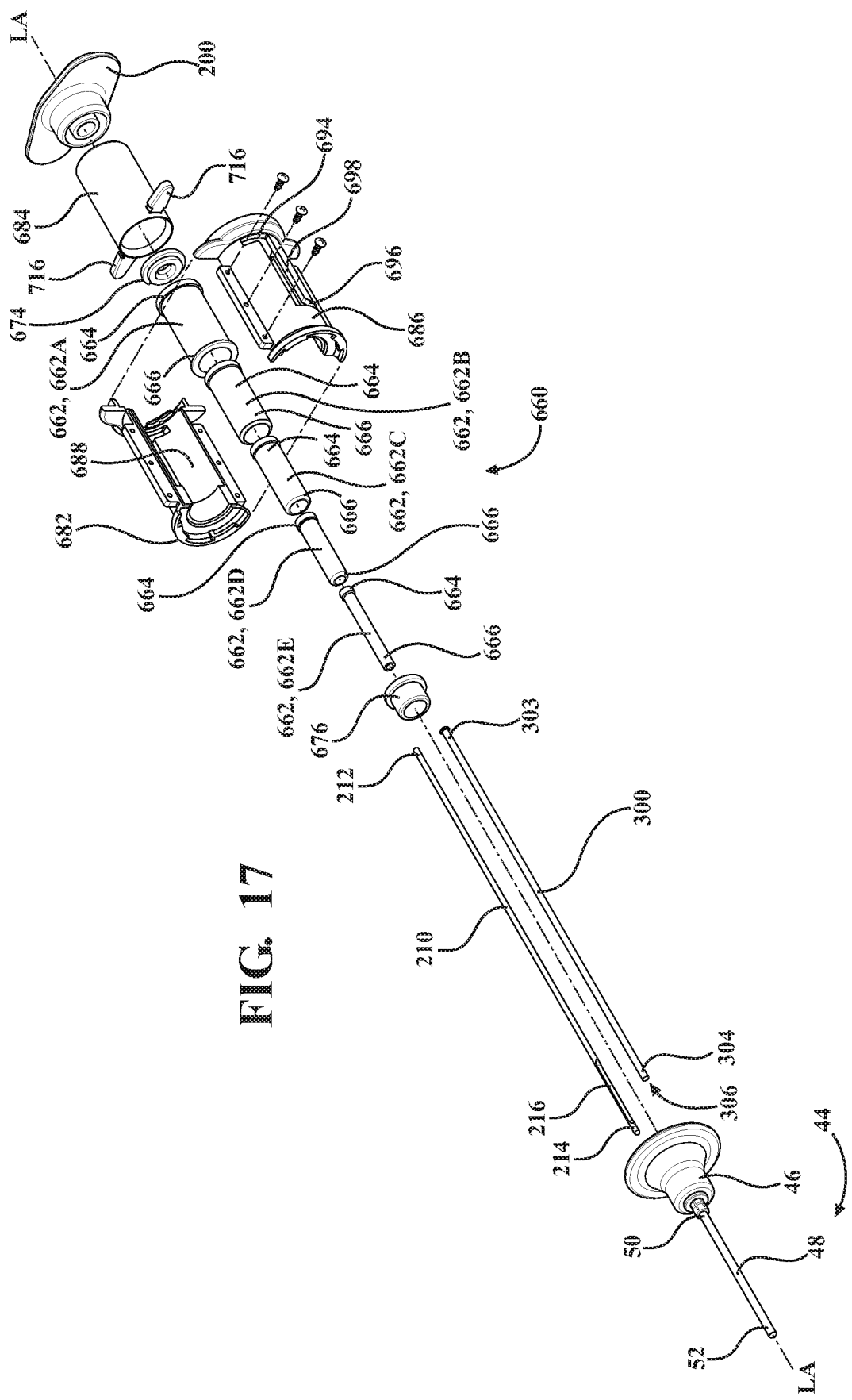
FIG. 17 is an exploded view of the telescoping introducer device of FIGS. 15 and 16.
Figure 18:
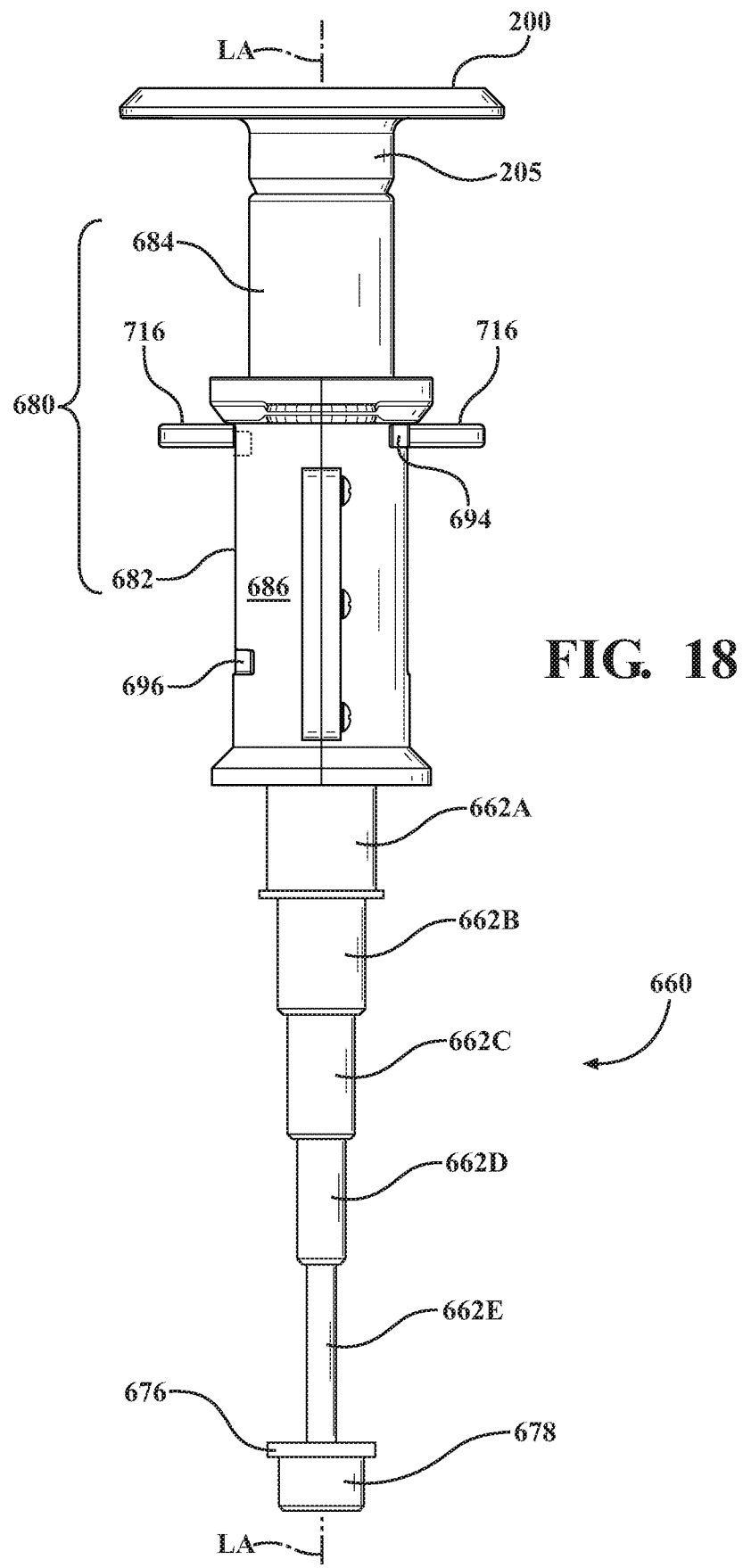
FIG. 18 is a perspective view of the stylet coupled to and contained within the introducer device, with the introducer device in the extended or telescoping position and with the hub assembly in the initial position.

Next, the cement delivery system 500, or cement delivery system 500, is coupled to the introducer device 42, as shown in FIG. 14. A curable material, here bone cement, is then introduced from the cement delivery system 500 through the lumen 306 of the sheath 300 and into the internal cavity of the vertebral body to fill the internal cavity. As shown in FIG. 14, the cement delivery system 500 may include a housing 502, a first control surface 504 coupled to the housing, and a second control surface 506 coupled to the housing 502. The first and second control surfaces 504, 506 are configured to receive inputs from the practitioner. For example, a rotational input to the first control surface 504 with one hand of the practitioner may advance a piston (not shown) with a chamber 508 to urge the curable material through the cement delivery system 500. An input to the second control surface 506 with the other hand of the practitioner may be required to permit advancement of the piston, and release of the input to the second control surface 506 may act as a "dead man's switch" for ceasing distal movement of the piston (and permitting proximal movement of the piston). Operation of the cement delivery system 500 is further disclosed in commonly owned International Publication No. WO2019/200091, published Oct. 17, 2019, the entire contents of which are hereby incorporated by reference. Another suitable cement delivery system is disclosed in commonly owned U.S. Pat. No. 6,547,432, issued Apr. 15, 2003, the entire contents of which are hereby incorporated by reference, and sold under the tradename PCD System by Stryker Corporation (Kalamazoo, Mich.). Still another suitable cement delivery system is disclosed in commonly owned U.S. Pat. No. 7,658,537, issued Feb. 9, 2010, the entire contents of which are hereby incorporated by reference, and sold under the tradename AutoPlex by Stryker Corporation (Kalamazoo, Mich.).

The cement delivery system 500 may include an extension tube 510 is adapted to be coupled to the coupling region 89 of the outer hub 82, as also shown in FIG. 14. The extension tube 510 includes a proximal coupler 512 coupled to the chamber 508, and a distal coupler 514 coupled to the outer hub 82. The arrangement establishes communication between the chamber 508 and the sheath 300. One or both of the proximal and distal couplers 512, 514 may be pivotable, and additional segments of tubing may be provided. Further construction of the extension tube 510 is disclosed in the aforementioned International Publication No. WO2019/200091. The extension tube 510 advantageously provides the physician with improved maneuverability about the patient and the surgical site without placing undue stress on the surgical instrument rigidly secured within the patient. Further, in procedures where fluoroscopy is utilized, the practitioner may deliver the curable material to within the interior region the vertebral body while avoiding unnecessary exposure to radiation.

With continued reference to FIG. 14, the hub assembly 80 is once in the supplemental position. The distal coupler 514 of the extension tube 510 may be coupled to the outer hub 82, and the cement delivery system 500 operated to direct the curable material (CM) from the chamber 508 through central openings 95, 124, lumen 150 and bore 63 of the introducer device 42, and through the lumen 306 of the sheath 300 including the distal end 304 in the curve configuration, and into the cavity (CA) within the interior region of the vertebral body. It is contemplated that the sheath 300 may be proximally retracting while the curable material is being delivered so as to move the distal end 304 of the sheath 300 and locate the entry point of the curable material as desired. For example, the hub assembly 80 may be returned to the initial position from the supplemental position to facilitate the practitioner utilizing the syringe-style input previously described. The cement delivery system 500 is then uncoupled from the introducer device 42. The introducer device 42 is then uncoupled from the access cannula 44 and removed. The trocar may be reintroduced through the access cannula 44, and the access cannula 44 and trocar removed from the vertebral body. The overlying tissue may be sutured, completing the stabilization of the vertebral body.

FIGS. 15-22 illustrate the system 40 similar to that in FIGS. 1-14, but wherein the design of the introducer device 642 is slightly altered while generally describing the same method for augmenting the vertebral body as described above. Accordingly, the introducer device 642 includes a telescoping introducer shaft 660 coupled to a hub assembly 680. Similar to the telescoping introducer shaft 60 of FIGS. 1-14, the telescoping introducer shaft 660 has a plurality of shaft sections 662 (shown as five shaft sections 662A, 662B, 662C, 662D and 662E in FIGS. 17, 19, 20, and 20A) moveable between an extended position (see FIG. 19) and a non-extended position (see FIGS. 20, 20A, 21), with the telescoping introducer shaft 660 defining an internal bore 663 extending along the longitudinal axis LA with the internal bore 663 configured so as to receive the stylet 200 when the telescoping introducer shaft 660 is coupled to the cannula hub portion 46 of the access cannula 44. Each one of the plurality of shaft sections 662 is formed of a hollow tubular member extending between a proximal end 664 and a distal end 666. As best shown in FIG. 20A, the proximal end 664 of each one of the plurality of shaft sections 662 includes an outwardly projecting proximal ledge 668, while the distal end 666 each one of the plurality of shaft sections 662 includes an inwardly projecting distal ledge 670. The outermost one 662A of the plurality of shaft sections 662 also includes an outwardly projecting distal ledge 672.

The telescoping introducer shaft 660 also includes a proximal tubular cap 674 coupled to the outwardly projecting proximal ledge 668 of the innermost one 662E of the plurality of shaft sections 662 and positioned adjacent to the proximal end 664 of each of the additional ones of the plurality of shaft sections 662A-662D in the non-extended position. The telescoping introducer shaft 660 also includes a distal tubular cap 676 coupled to the distal end 666 of the outermost one 662A of the plurality of shaft sections 662 and positioned adjacent to the distal end 666 of each of the additional ones of the plurality of shaft sections 662B-662E in the non-extended position. The distal tubular cap 676 includes a flange portion 678 that is used to couple the telescoping introducer shaft 660 to the cannula hub portion 46 of the access cannula 44.

Figure 19:
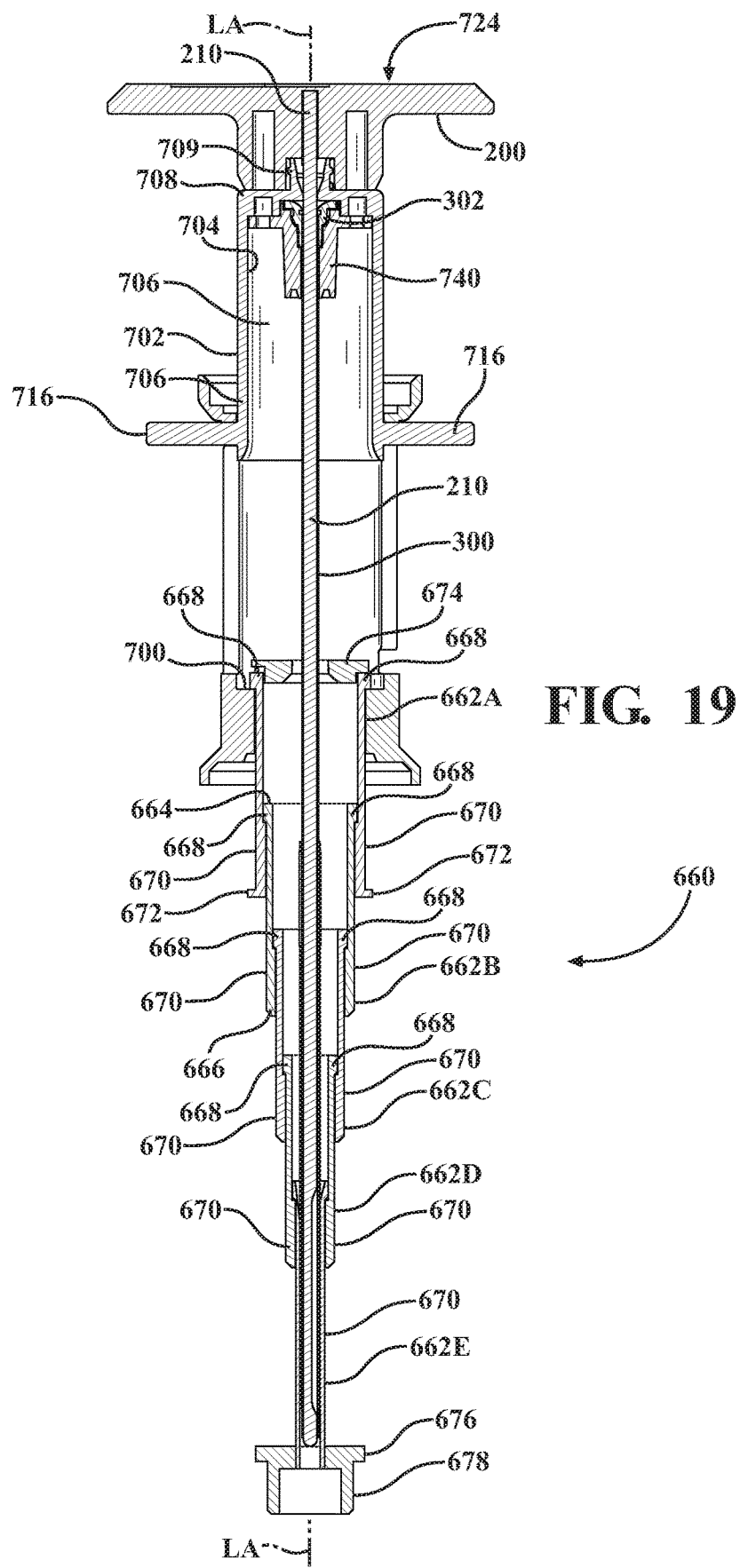
FIG. 19 is a section view of FIG. 18.
Figure 21:
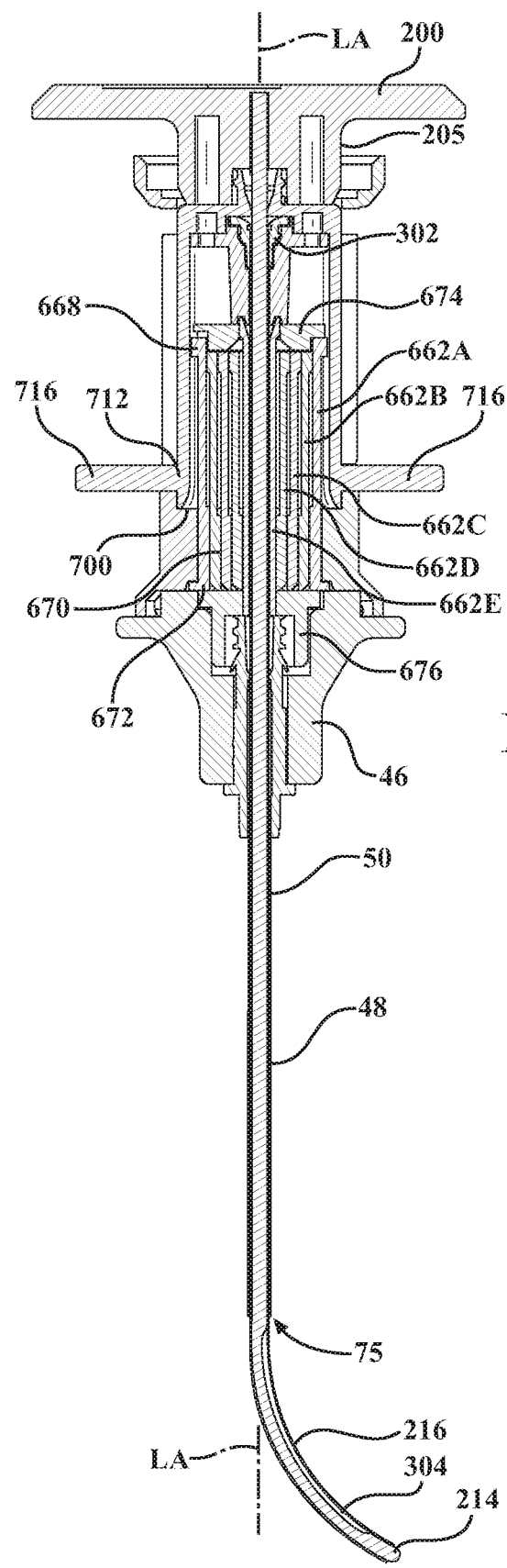
FIG. 21 is a section view of the stylet coupled to and contained within the introducer device of FIG. 18 with the introducer device in the non-extended position and the hub assembly in the supplemental position.

When in the non-extended position, as best shown in FIG. 20A, each one of the plurality of shaft sections 662 includes wherein the respective proximal ends 664 are aligned with one another in a direction normal to the longitudinal axis LA and wherein the proximal tubular cap 674 is adjacent the proximal end 664 of each one of the plurality of shaft sections 662A-662E. In addition, each one of the respective distal ends 666 are also aligned with one another in a direction normal to the longitudinal axis LA and wherein the distal tubular cap 676 is adjacent the distal end 666 of each one of the plurality of shaft sections 662A-662E. In this non-extended position, the inwardly projecting distal ledge 670 of a respective one of the plurality of shaft sections 662 is spaced from and longitudinally aligned with the inwardly projecting distal ledge 670 on the next adjacent inward one of the plurality of shaft sections 662 and with the outwardly projecting distal ledge 672. Conversely, in the extended position, as best shown in FIG. 19, each one of the respective proximal ends 664, and each one of the respective distal ends 666, of the shaft sections 662 are not aligned with one another in a direction normal to the longitudinal axis LA. In this non-extended position, the inwardly projecting distal ledge 670 of a respective one of the plurality of shaft sections 662 is contacting the longitudinally aligned with the outwardly projecting proximal ledge 668 on the next adjacent inward one of the plurality of shaft sections 662. In addition, while the proximal tubular cap 674 remains connected to the outermost one 662A of the plurality of shaft sections 662, the proximal tubular cap 674 is spaced from the proximal end 664 of each of the additional ones of the plurality of shaft sections 662B-662E. Still further, while the distal tubular cap 676 remains connected to the innermost one 662E of the plurality of shaft sections 662, the proximal tubular cap 674 is spaced from the distal end 666 of each of the additional ones of the plurality of shaft sections 662A-662D.

The hub assembly 680 includes an outer hub 682 and an inner hub 684 moveable along the longitudinal axis relative to and within the outer hub 682 between an initial position and a supplemental position in which the inner hub 684 is moved distally relative to the outer hub 682. The outer hub 682 includes a longitudinally extending outer surface 686 and an opposing longitudinally extending inner surface 688 defining an interior region 690 configured for receiving the inner hub 684. The outer hub 682 also includes at least one slot 692, here shown as a pair of slots 692, extending through and between the longitudinally extending outer surface 686 and the opposing longitudinally extending inner surface 688. The slot 692 has an initial slot locking region 694 corresponding to the initial position and a supplemental slot locking region 696 corresponding to the supplemental position. The slot 692 also includes a longitudinally extending middle slot region 698 connecting the initial and supplemental slot locking regions 694, 696, with the initial and supplemental slot locking regions 694, 696 extending in a direction transverse to the longitudinally extending middle slot region 698. The inner surface 688 of the outer hub 682 includes a ledge portion 700, which extends inwardly towards the longitudinal axis LA and extends between the outwardly projecting distal ledge 672 and the outwardly projecting proximal ledge 668 of the outermost one 662A of the plurality of shaft sections 662.

The inner hub 684 also includes a longitudinally extending outer surface 702 and an opposing longitudinally extending inner surface 704 defining an interior region 706, with the interior region 706 further defining the bore 663. A proximal portion 708 of the inner hub 684 is open to the exterior of the outer hub 682 and includes a projecting hub portion 709 defining a central opening 724 through which the stylet 200 may be introduced after the introducer device 642 is coupled to the cannula hub portion 46 of the access cannula 44. The distal portion 712 of the inner hub 684 is contained within the outer hub 682 in both the initial and locking position, with the distal portion 712 positioned adjacent to the ledge portion 700 in the locked position and spaced from the ledge portion 700 in the supplemental position.

The inner hub 684 also includes at least one alignment member 716, here shown as a pair of alignment members, extending outwardly from the longitudinally extending outer surface 702. Each one of the alignment members 716 is disposed through a corresponding one of the one or more slots 692. Accordingly, the movement of the inner hub 684 relative to the outer hub 682 is limited to a path corresponding to the respective slot 692.

The telescoping introducer device 642 also includes the sheath 300 (as described above with respect to FIGS. 1-14), with the proximal end hub portion 302 positioned adjacent to the inner surface 704 of the proximal portion 708 of the inner hub 684. The sheath 300 also includes a distal end 304 opposite the proximal end 303 configured to be positioned at or near the distal end 214 of the shaft 210 of the stylet 200.

The telescoping introducer device 642 also includes a fastener device 740 that is positioned within the interior region 706 of the inner hub 684 between the proximal tubular cap 674 and the inner surface 704 that is used to couple the proximal end hub portion 302 of the sheath 300 between the fastener device 740 and the inner surface 704.

A workflow of performing a vertebral augmentation with the system 40 (i.e., a method for stabilizing a vertebral body) with the modified introducer device 642 will now be described with particular reference to FIGS. 15-27. The vertebra with the offending vertebral body may be confirmed on fluoroscopic imaging. An incision may be made in the overlying paraspinal musculature lateral of midline generally in alignment with one of the pedicles of the vertebra.

The method begins by positioning the distal end 58 of the access cannula 44 within the vertebral body such that a lumen 75 of the access cannula 44 provides access to an interior of the vertebral body along the longitudinal axis LA. The distal end 58 of the access cannula 44, with the trocar disposed therein, is then directed through the pedicle a position beyond the cortical rim and within the interior region of the vertebral body, and the trocar is removed. The access cannula 44 provides the working channel to within the interior region of the vertebral body along the longitudinal axis LA. The cannula hub portion 46 is exposed and configured to be engaged by the introducer device 42.

Figure 22:
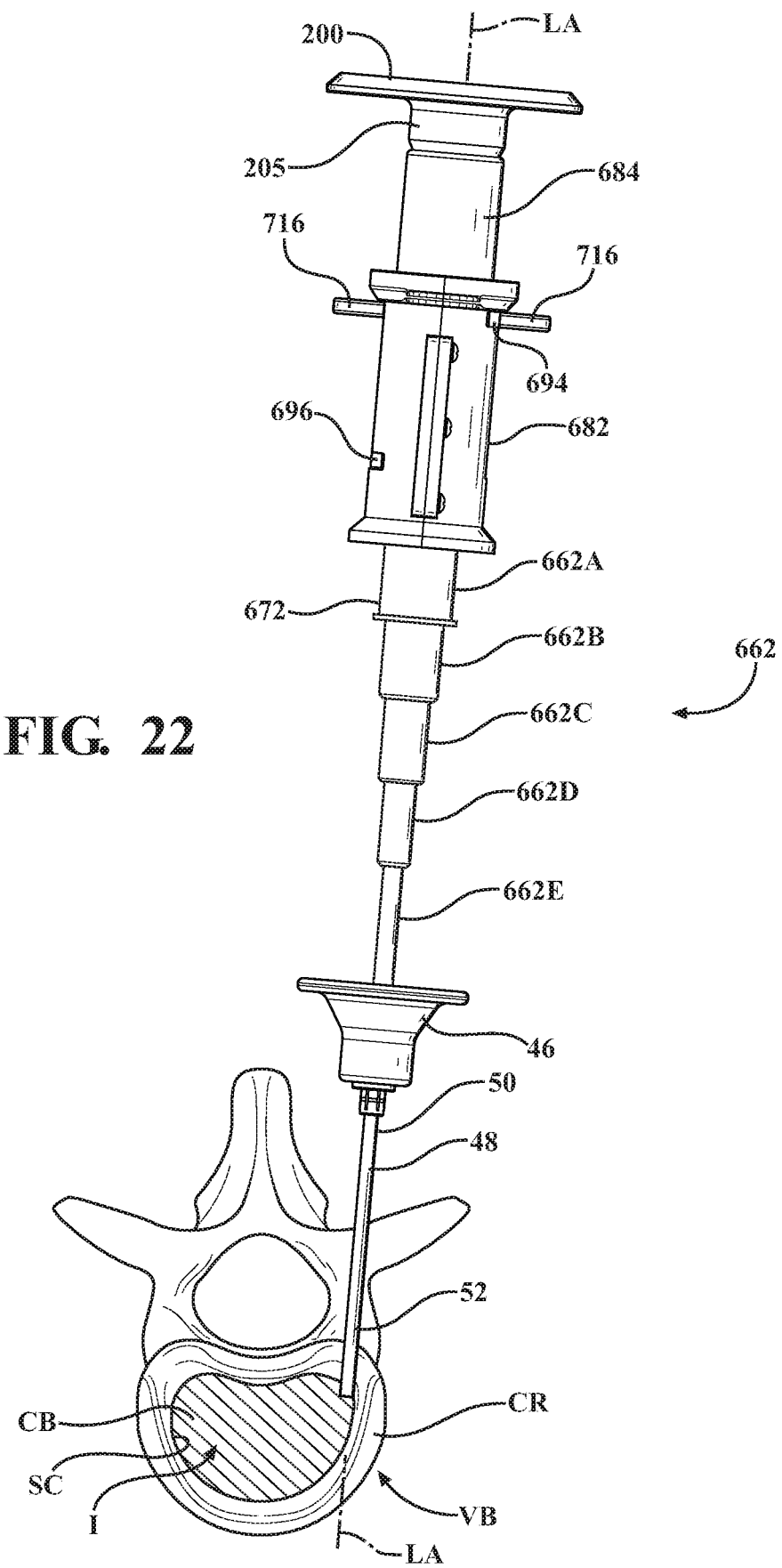
FIG. 22 is a perspective and partial section view of the stylet coupled to and contained within the introducer device which is coupled to the access cannula, with the introducer device in the extended or telescoping position and the hub assembly in the initial position, and with the distal end of the access cannula inserted within the vertebral body.

The method continues wherein the introducer device 642 is provided with the stylet 200 coupled thereto, and in particular where the stylet shaft 210 of the stylet 200 is contained within the internal bore 663 of the introducer device 642. In addition, the telescoping introducer shaft 660 is in the extended position, or telescoping position, while the hub assembly 680 is in the initial position, as shown in FIG. 22. As noted above, in the extended position, the inwardly projecting distal ledge 670 of a respective one of the plurality of shaft sections 662 is contacting the outwardly projecting distal ledge 672 on the next adjacent inward one of the plurality of shaft sections 662. In addition, while the proximal tubular cap 674 remains connected to the outermost one 662A of the plurality of shaft sections 662, the proximal tubular cap 674 is spaced from the proximal end 664 of each of the additional ones of the plurality of shaft sections 662B-662E. Still further, while the distal tubular cap 676 remains connected to the innermost one 662E of the plurality of shaft sections 662, the proximal tubular cap 674 is spaced from the distal end 666 of each of the additional ones of the plurality of shaft sections 662A-662D. As a result, the entirety of the stylet shaft 210 and sheath 300 are retained within the internal bore 663 of the introducer device 642, with the flexible distal portion 216 of the stylet shaft 210 in the constrained state (i.e., generally straight as shown in FIG. 20).

Next, the introducer device 642 is coupled to the access cannula 44 with the telescoping introducer shaft 660 in the extended position and the hub assembly 680 in the initial position. In particular, the distal tubular cap 676 of the introducer device 642 is engaged with the cannula hub portion 46 such that the lumen 75 of the cannula shaft 48 is aligned with the lumen 650 of the telescoping introducer shaft 660.

Figure 23:
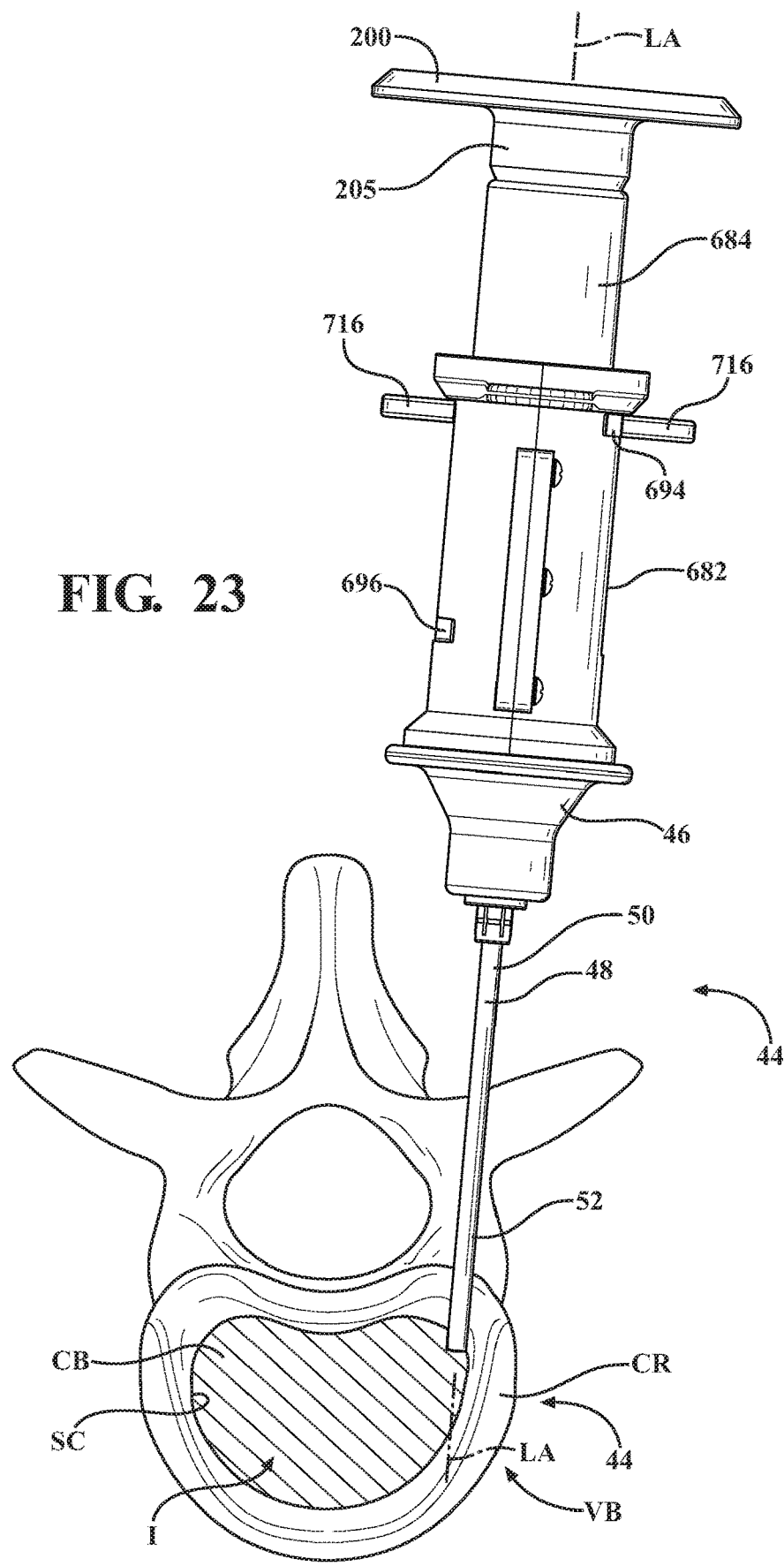
FIG. 23 is a perspective and partial section view of the stylet coupled to and contained within the introducer device which is coupled to the access cannula, with the introducer device in the non-extended position and the hub assembly in the initial position, and with the distal end of the access cannula inserted within the vertebral body.

Next, the telescoping introducer shaft 660 is moved from the extended position, as shown in FIG. 22, to the non-extended position, while maintaining the hub assembly 80 in the initial position, as shown in FIG. 23. The collapsing of the shaft sections 662 results in the distal end 214, 304 of the stylet shaft 210 and flexible sheath 300, respectively, moving from the internal bore 663 to within the lumen 75 of the cannula shaft 48, but wherein the flexible distal portion 216 remains in the constrained state within the cannula shaft 48. In particular, the distal end 214 of the stylet shaft 210 is brought into registration with the distal end 52 of the access cannula 44. Notably, the collapsing does not, however, bring the distal end 214 of the stylet shaft 210 in penetration within the vertebral body, which prevents damage to the vertebral body associated with the collapsing movement.

Next, the hub assembly 680 is moved from the initial position to the supplemental position. This results in the distal end 214, 304 of the stylet shaft 210 and flexible sheath 300, respectively, moving beyond the distal end 52 of the access cannula 44 to within the target site in the vertebral body offset from the longitudinal axis LA, wherein the flexible distal portion 216 moving from the constrained state to the unconstrained state (see FIG. 24) to displace cancellous bone within the target site of the vertebral body target. In particular, the practitioner can engage the alignment member 716 to move the alignment member 716 along the middle slot region 698 from a position corresponding to the initial slot locking region 694 to a position corresponding to the supplemental slot locking region 696. This results in the inner hub 684 moving in a direction distally towards the access cannula 44 and relative to the outer hub 682 such that the distal portion 712 of the inner hub 684 adjacent to the distal ledge portion 700. The movement of the inner hub 684 also results in the movement of the coupled stylet 200 (and hence the coupled stylet shaft 210) and the coupled sheath 300 distally as well relative to the outer hub 682 and access cannula 44. This results in the distal end 214, 304 of the stylet shaft 210 and flexible sheath 300, respectively, moving beyond the distal end 52 of the access cannula 44 to within the target site in the vertebral body offset from the longitudinal axis LA, as noted above and as illustrated in FIGS. 15 and 24, and with the flexible distal portion 216 moving from the constrained state to the unconstrained state to displace cancellous bone within the target site of the vertebral body target.

Figure 24:
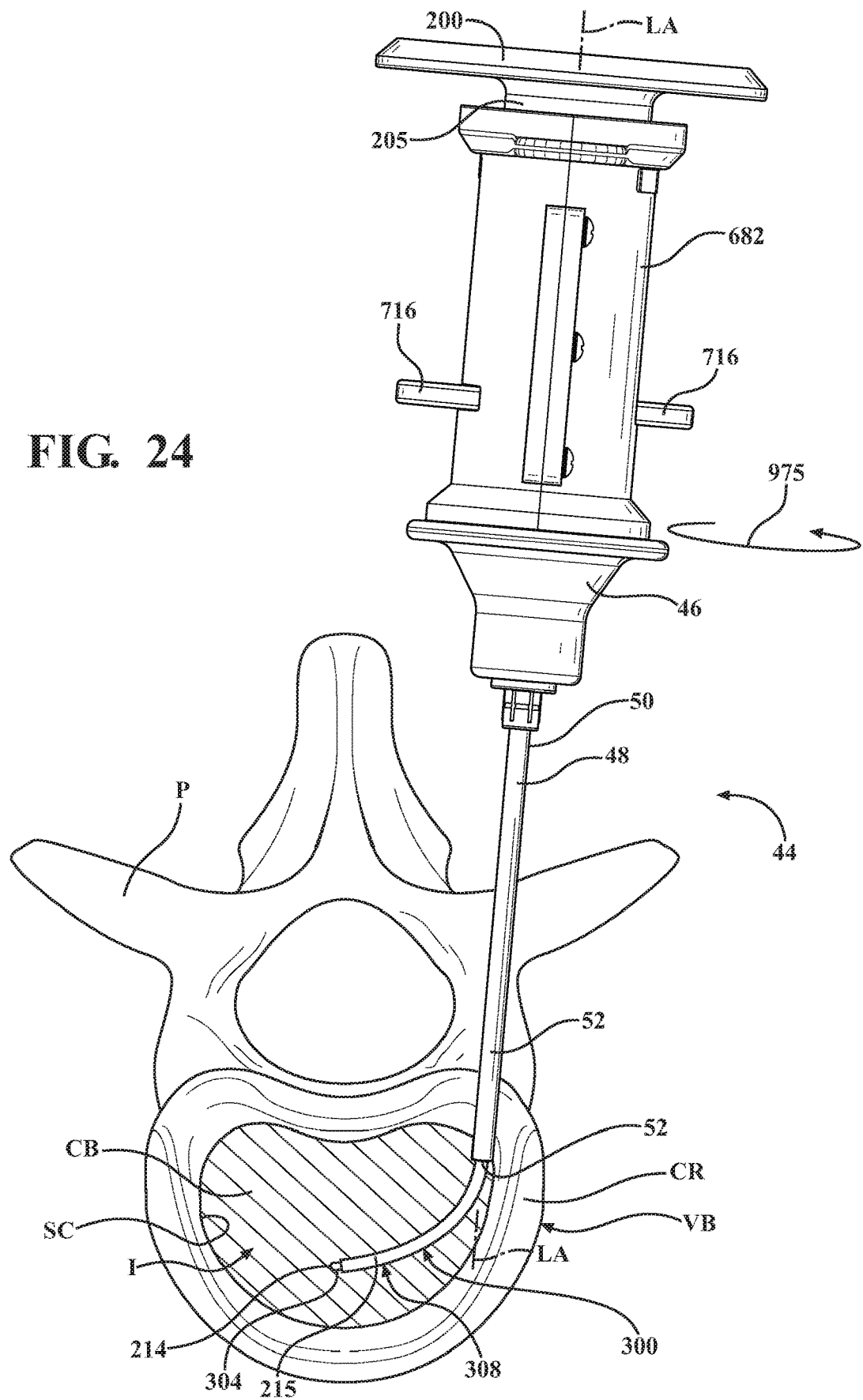
FIG. 24 is a perspective and partial section view of the stylet coupled to and contained within the introducer device which is coupled to the access cannula, with the introducer device in the non-extended position and the hub assembly in the supplemental and unlocked position, and with the distal end of the access cannula inserted within the vertebral body.

Next, the method continues by locking the inner hub 684 with the outer hub 682 in the supplemental position by rotating the inner hub 684 relative to the outer hub 682 about the longitudinal axis LA in a first rotational direction (shown by arrow 975 in FIG. 24). In particular, the practitioner can engage the alignment member 716 to move the alignment member 716 along the supplemental slot locking region 696 in a direction away from the middle slot region 698. In this position, the inner hub 684 is prevented from moving in the longitudinal direction A by virtue of the alignment member 716 contacting supplemental slot locking region 696.

Figure 25:
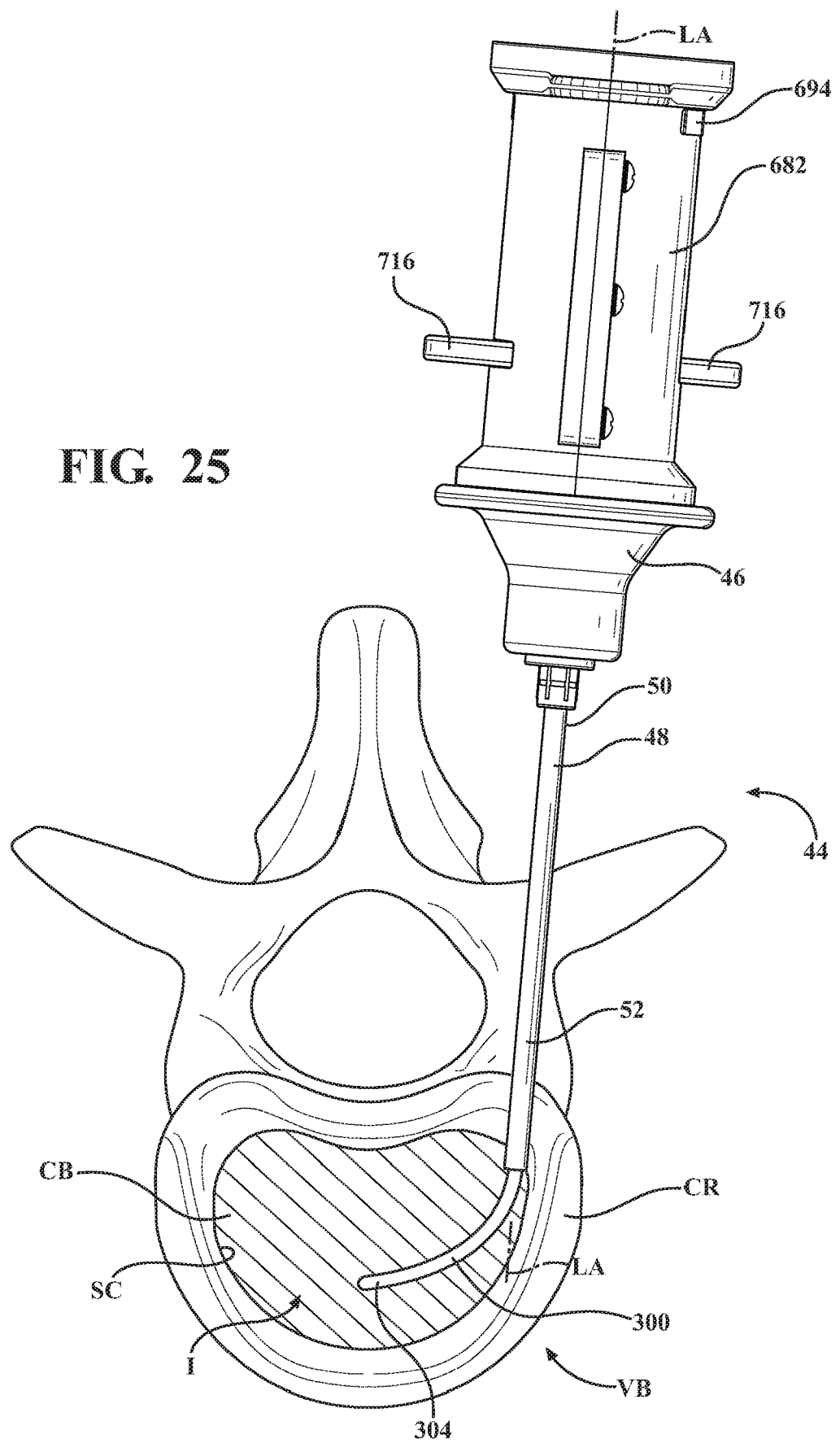
FIG. 25 is a perspective and partial section view of FIG. 24 with the stylet removed, with the introducer device in the non-extended position and the hub assembly in the supplemental and locked position, and with the distal end of the access cannula inserted within the vertebral body.

Next, the method continues by removing the stylet 200 from the introducer device 642 while the inner hub 684 is locked with the outer hub 682 in the supplemental position and with the telescoping introducer shaft 660 in the non-extended position, as shown in FIG. 25. In particular, the stylet 200 is uncoupled from the outer hub 682 and pulled in a direction away from the introducer device 642, resulting in the shaft 210 being retracted through the lumen 75 of the cannula shaft 48 and through the lumen 650 of the telescoping introducer shaft 660 until the distal end 214 exits from the central opening 724. During this step, the distal end 304 of the flexible sheath 300 remaining positioned at the target site offset from the longitudinal axis LA.

Figure 26:
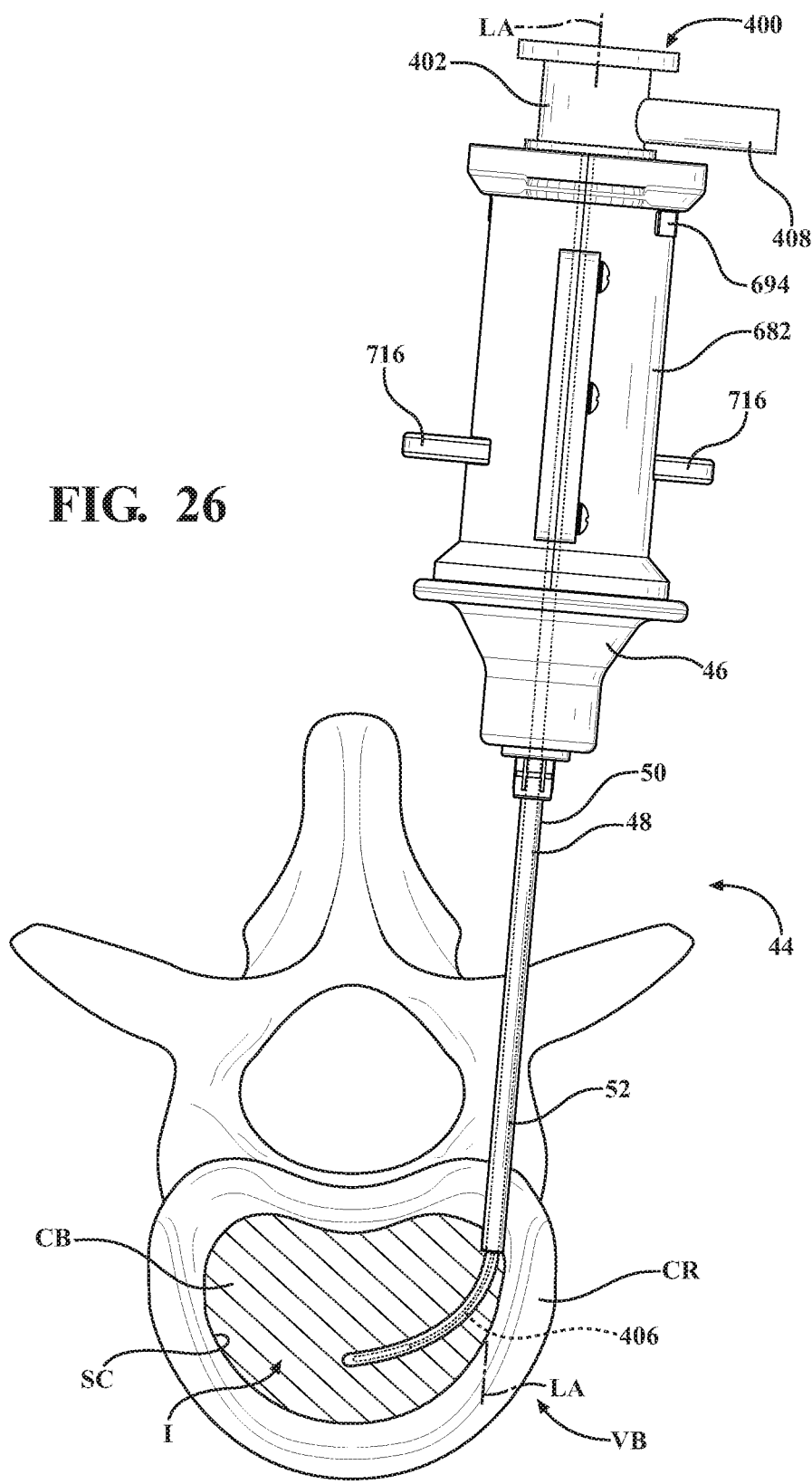
FIG. 26 is a perspective and partial section view of FIG. 25 with a balloon assembly coupled to the introducer device, with the introducer device in the non-extended position and the hub assembly in the supplemental and locked position, and with the balloon in a deflated state.

The removal of the stylet 200, while the inner hub 684 is locked with the outer hub 682 in the supplemental and locked position, does not require the practitioner/surgeon to simultaneously hold the sheath 300 in place during stylet removal as is necessary in typical introducer devices used in performing the unipedicular approach. Next, the balloon assembly 400 is coupled onto the introducer device 642 while the hub assembly 680 remains in the supplemental and locked position, as shown in FIG. 26. In particular, the balloon hub 402 is engaged with outwardly projecting proximal ledge 668 of the outer hub 682 to secure the balloon assembly 400 to the hub assembly 680 with the hub assembly 680 in the supplemental position. The balloon tube 404 may extend through, in sequence, the central opening 124, the lumen 150 and bore 63 of the introducer device 642, the lumen 306 of the sheath 300 extending through the bore of the cannula hub portion 46 and the lumen 75 of the cannula shaft 48. With the hub assembly 680 in the supplemental position, a distal end 410 of the balloon 406 is near or in registration with the distal end 304 of the sheath 300, as also shown in FIG. 26. The balloon 406 is in the deflated state and sheathed within the distal end 304 of the sheath 300 in the curved configuration.

Figure 27:
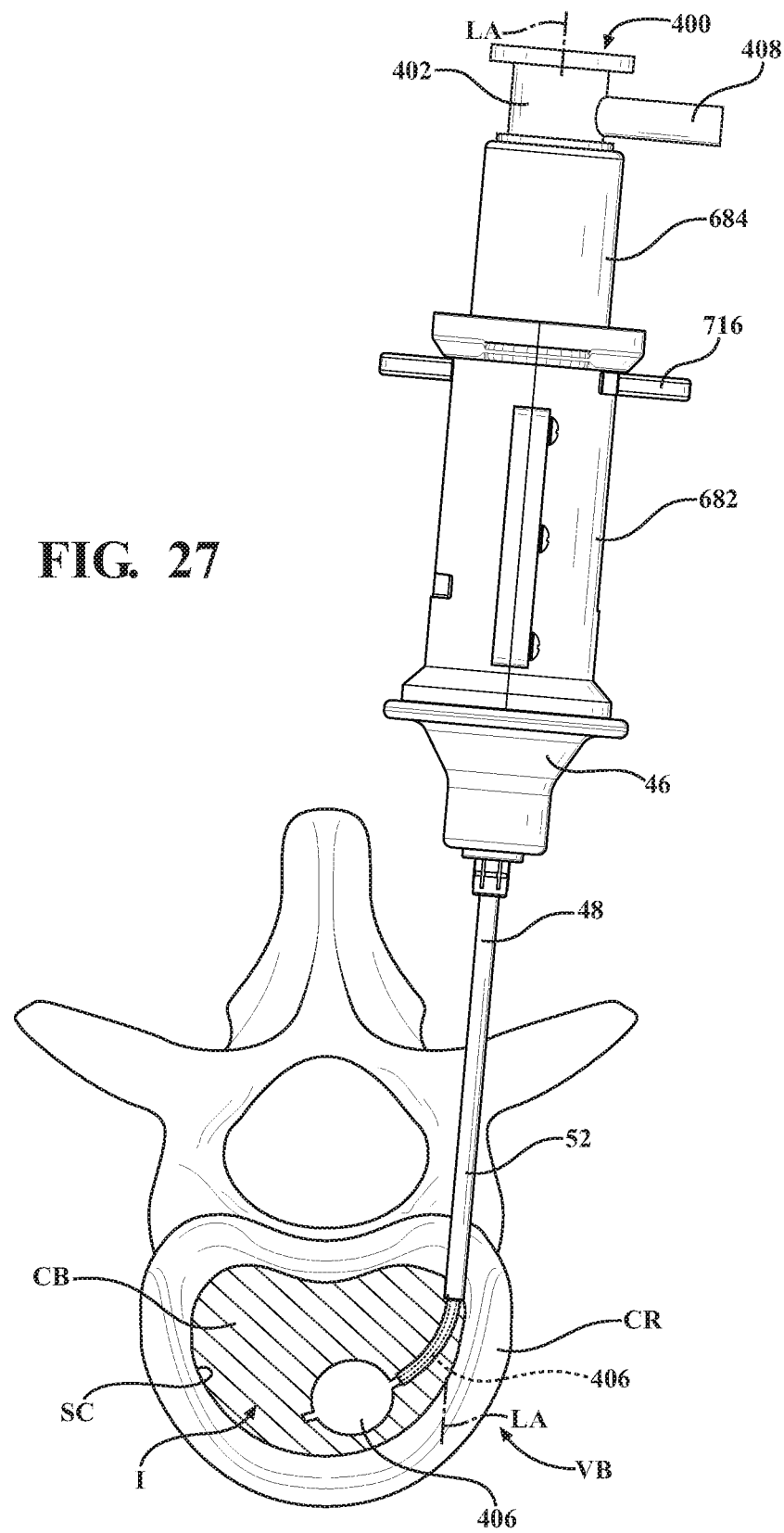
FIG. 27 is a perspective and partial section view of FIG. 25 with a balloon assembly coupled to the introducer device, with the introducer device in the non-extended position and the hub assembly in the initial position, and with the balloon in an inflated state

After the balloon 406 is positioned near or in registration with the distal end 304 of the sheath 300 in the deflated state, the balloon 406 may be unsheathed by moving the hub assembly 680 from the supplemental position towards the initial position such that the balloon 406 extends beyond the distal end 304 of the sheath 300 and within the target area of the vertebral body. In particular, as shown in FIG. 27, the practitioner may move the hub assembly 680 from the supplemental and locked position to the supplemental and unlocked position by moving the alignment member 716 along the supplemental slot locking region 696 in a direction towards from the middle slot region 698, causing the inner hub 684 to rotate around the longitudinal axis LA in the opposite direction to arrow 975 in FIG. 24. Next, the practitioner moves the alignment member 716 proximally away from the access cannula 44 within the middle slot region 698, which causes the coupled sheath 300 to move proximally as well. The balloon 406 is unsheathed and exposed within the interior region of the vertebral body in the deflated state, after which the balloon 406 may be moved to the inflated state to displace the cancellous bone, as also shown in FIG. 27. In particular, after the deflated balloon 406 is unsheathed by moving the hub assembly 680 to the initial position or towards the initial position within the middle slot region 698, the balloon 406 may then be inflated by introducing fluid from the source of fluid through the balloon hub 402 and the balloon tube 404. The inflated balloon 406 displaces cancellous bone within the vertebral cavity. With the balloon 406 in the inflated state, the balloon 406 is returned to the deflated state to form the cavity 420 within the cancellous bone for delivery of the curable material from the cement delivery system 500. The balloon 406 is then removed by moving the balloon 406 into and through the sheath 300. The balloon assembly 400 is simultaneously or otherwise uncoupled from the hub assembly 680.

Figure 28:
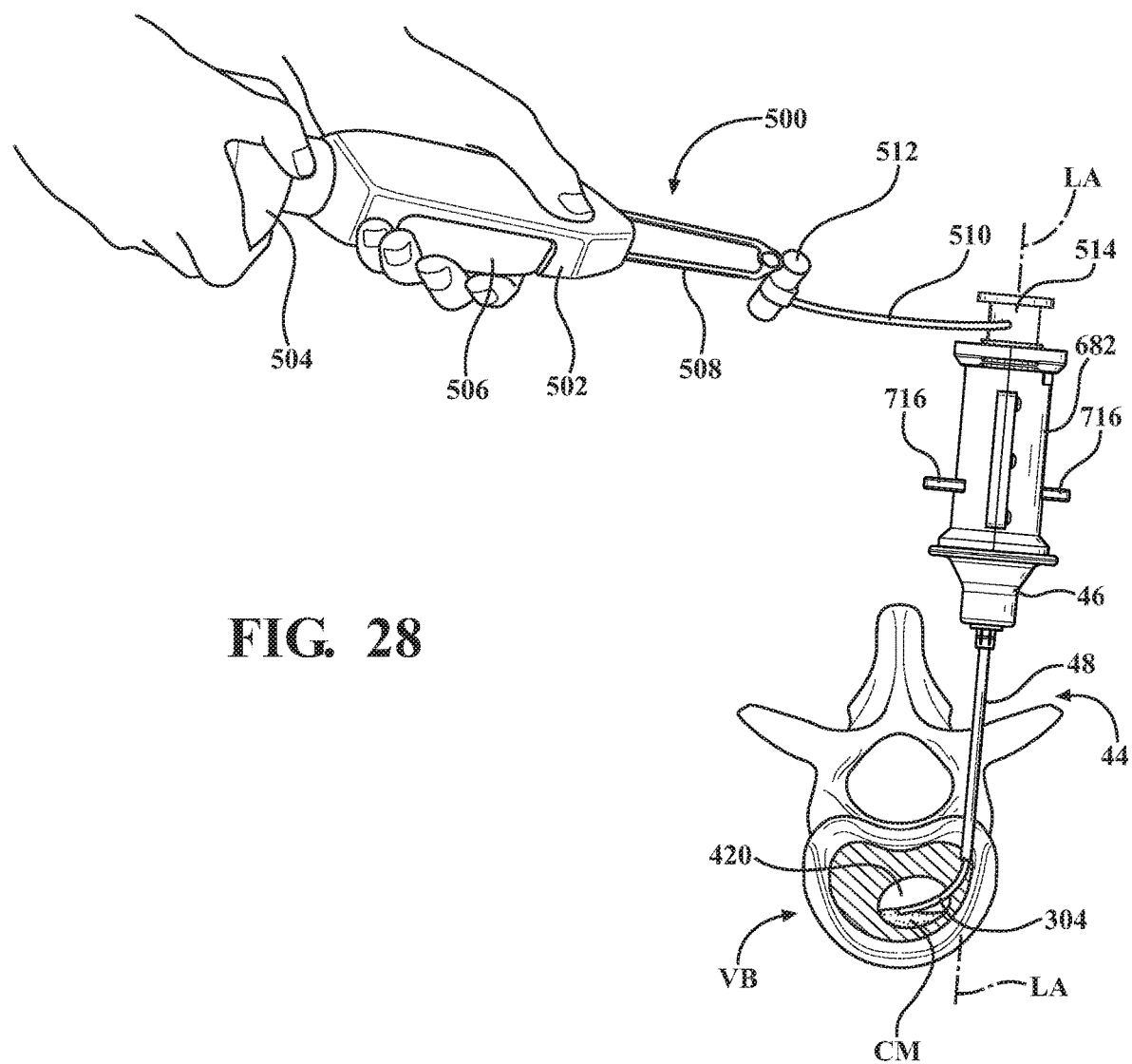
FIG. 28 is a perspective and partial section view of FIG. 25 with a bone cement delivery device coupled to the introducer device, with the introducer device in the non-extended position and the hub assembly in the supplemental position, and with the bone delivery device delivering a curable material to the vertebral body.

Next, the cement delivery system 500, or cement delivery system 500, is coupled to the introducer device 642, as shown in FIG. 28. In particular, the cement delivery system 500 is coupled to the introducer device 642, and in particular the cement delivery system 500 is engaged with outwardly projecting proximal ledge 668 of the outer hub 682 to secure the cement delivery system 500 to the hub assembly 680 with the hub assembly 680 in the supplemental position, or in the supplemental and locked position. A curable material CM, here bone cement, is then introduced from the cement delivery system 500 through the lumen 306 of the sheath 300 and into the internal cavity of the vertebral body to fill the internal cavity in the same manner generally described above with respect to FIG. 14. The cement delivery system 500 is then uncoupled from the introducer device 642. The introducer device 642 is then uncoupled from the access cannula 44 and removed. The trocar may be reintroduced through the access cannula 44, and the access cannula 44 and trocar removed from the vertebral body. The overlying tissue may be sutured, completing the stabilization of the vertebral body.

FIGS. 29-37 describe yet another related introducer device for use in the system 40 for augmentation of the vertebral body. The introducer device, as opposed to utilizing a telescoping introducer shaft as in the introducer devices 42 and 642 as described above, is a pivoting introducer device 1000 that includes a hub assembly 1002, moveable along the longitudinal axis between an initial position and a supplemental position, and a pivoting member 1050 configured for coupling to the cannula hub portion 46 (i.e. hub portion) of the access cannula 44.

The hub assembly 1002 is similar to the hub assembly 680 described in FIGS. 15-28 above and includes an outer hub 1012 and an inner hub 1014 moveable along the longitudinal axis relative to and within the outer hub 1012 between an initial position and a supplemental position in which the inner hub 1014 is moved distally relative to the outer hub 1012. The outer hub 1012 includes a longitudinally extending outer surface 1016 extending between a proximal end 1017 and a distal end 1019 and an opposing longitudinally extending inner surface 1018 defining an interior region 1020 configured for receiving the inner hub 1014. The outer hub 1012 also includes at least one slot 1022, here shown as a pair of slots 1022, extending through and between the longitudinally extending outer surface 1016 and the opposing longitudinally extending inner surface 1018. The slot 1022 has an initial slot locking region 1024 corresponding to the initial position and a supplemental slot locking region 1026 corresponding to the supplemental position. The slot 1022 also includes a longitudinally extending middle slot region 1028 connecting the initial and supplemental slot locking regions 1024, 1026, with the initial and supplemental slot locking regions 1024, 1026 extending in a direction transverse to the longitudinally extending middle slot region 1028.

The inner hub 1014 also includes a longitudinally extending outer surface 1032 and an opposing longitudinally extending inner surface 1034 defining an interior region 1036, with the interior region 1036 further defining the bore 1030. A proximal portion 1038 of the inner hub 1014 is open to the exterior of the outer hub 1012 and includes a projecting hub portion 1040 defining a central opening 1044 through which the stylet 200 may be introduced after the introducer device 1000 is coupled to the cannula hub portion 46 of the access cannula 44. The distal portion 1042 of the inner hub 1014 is contained within the outer hub 1012 in both the initial and locking position.

The inner hub 1014 also includes at least one alignment member 1046, here shown as a pair of alignment members, extending outwardly from the longitudinally extending outer surface 1032. Each one of the alignment members 1046 is disposed through a corresponding one of the one or more slots 1022. Accordingly, the movement of the inner hub 1014 relative to the outer hub 1012 is limited to a path corresponding to the respective slot 1022.

The introducer device 1000 also includes the sheath 300 (as described above with respect to FIGS. 1-14), with the proximal end hub portion 302 positioned adjacent to the inner surface 1034 of the proximal portion 1038 of the inner hub 1014. The sheath 300 also includes a distal end 304 opposite the proximal end 303 configured to be positioned at or near the distal end 214 of the shaft 210 of the stylet 200.

The pivoting introducer device 1000 also includes a fastener device 1046 that is positioned within the interior region 1036 of the inner hub 1014 that is used to couple the proximal end hub portion 302 of the sheath 300 between the fastener device 1046 and the inner surface 1034.

Figure 29:
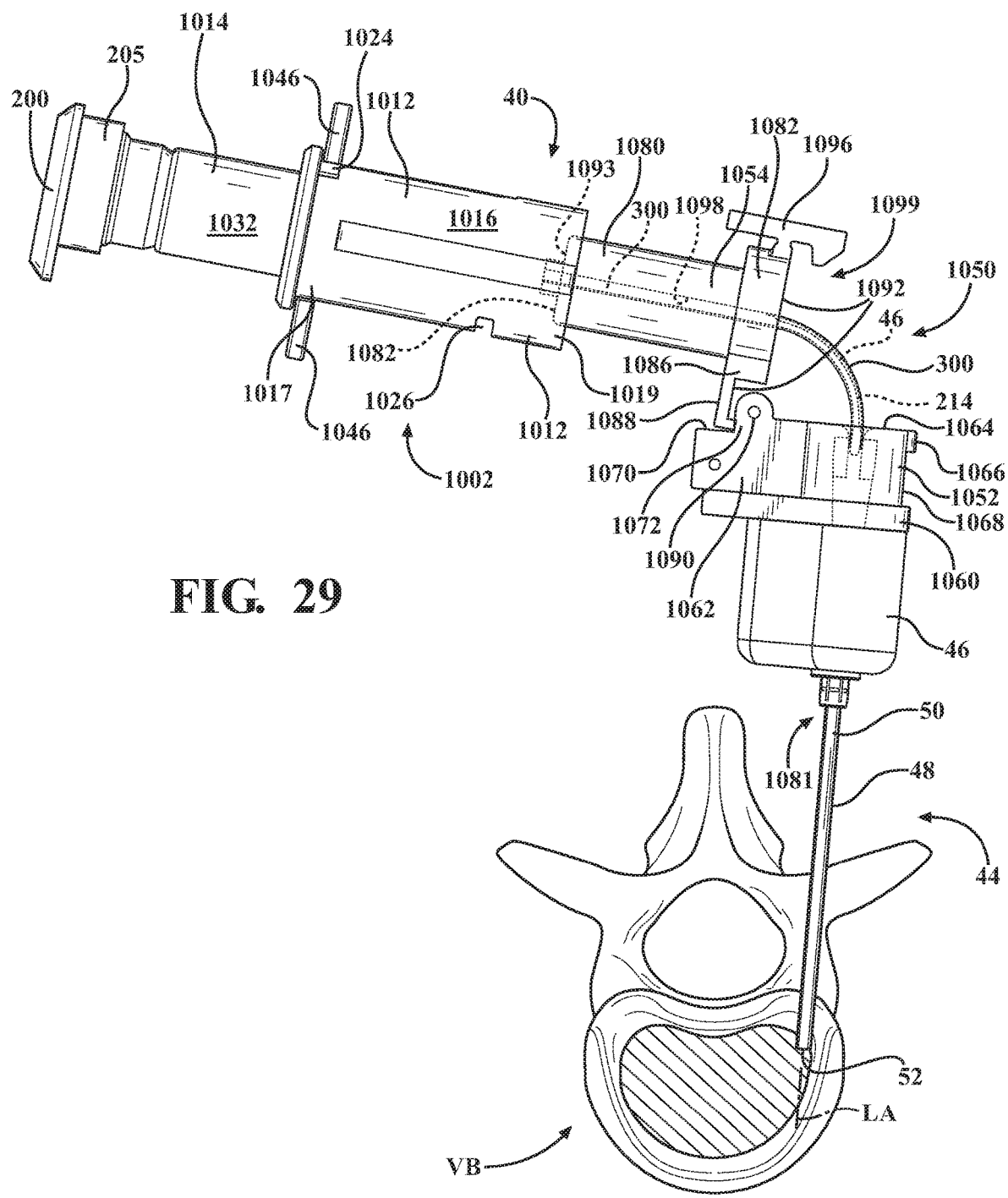
FIG. 29 shows a system for augmenting a vertebral body including a stylet, a pivoting introducer device different from the telescoping introducer device of FIGS. 1-14 and FIGS. 15-27, and an access cannula, with the stylet coupled to and contained within the introducer device which is coupled to the access cannula and with a pivoting portion of the introducer device in the prone position, with the hub assembly in the initial position, and with the distal end of the access cannula inserted within the vertebral body.

The pivoting member 1050 portion includes a base portion 1052 configured for coupling to the cannula hub portion 46 and a pivoting portion 1054 configured for coupling to the hub assembly 1002, with the pivoting portion 1054 being pivotable relative to the base portion 1052 between an upright position (see FIG. 30) and a prone position (see FIG. 29). The base portion 1052 includes a hollow interior portion 1060, or base coupling portion, that is sized and shaped for being reversibly secured around the cannula hub portion 46. The base portion 1052 also includes a top portion 1062 coupled to the hollow interior portion 1060, with the top portion 1062 configured for coupling to the pivoting portion 1004. The top portion 1062 includes top surface 1064 and includes an outwardly extending lip region 1066 extending from the top portion 1062 and a recessed region 1068 extending between the lip region 1066 and the interior portion 1060. The top portion 1062 also includes a pair of spaced apart pivot members 1088 and an inward recessed ledge 1070 positioned opposite the lip region 1066. The pivot members 1088 include axially aligned openings. The base portion 1052 further includes a ball-nose spring 1074 positioned within the hollow interior portion 1060 that is biasingly engaged to ridged projection portion 1076 of the cannula hub portion 46 when the base portion 1052 is coupled to the access cannula 44. A hexagonal positioning nut 1078 is positioned within the ridged projection portion 1076 which defines an internal bore 1081 that defines an end portion of the lumen 75 of the cannula 44 within the hub portion 46.

The pivoting portion 1054 includes a longitudinally extending outer surface 1080 extending between a proximal end 1082 and a distal end 1084. The distal end 1084 includes an outwardly projecting ledge region 1086 positioned adjacent to the distal end 1019 of the outer hub 1012 when the hub assembly 1002 is in the supplemental position. The inward region of the outwardly projecting ledge region 1086 of the pivoting portion 1054 includes a pair of spaced apart pivot members 1088 extending from a bottom surface 1092 having a respective pair of axially aligned openings with pins 1090 inserted within the axially aligned openings to pivotally attach the base portion 1052 to the pivot portion 1054. This pivotal attachment allows the pivotal movement of the base portion 1052 relative to the pivot portion 1054 between an upright position (see FIG. 30) and a prone position (see FIG. 29). The angular distance between the bottom surface 1092 of the pivoting portion 1054 and the top surface 1064 of the base portion 1052 may be defined as angle α therebetween. In particular, when the pivoting portion 1054 is in the prone position as shown in FIGS. 29 and 31, the angle α may vary in range between 0 and 75 degrees. The outward region of the outwardly projecting ledge region 1086 of the pivoting portion 1054 includes a snap 1096 which is configured to be reversibly secured around the recessed region 1068 adjacent to the lip region 1066 when the pivoting portion 1054 is in the upright position as shown in FIGS. 30 and 32-37. The pivoting portion 1054 includes a longitudinally extending inner surface 1098 that defines an internal bore 1099 to receive the stylet shaft 210 and the sheath 300. The internal bore 1099 is axially aligned with the bore 1030 and the bore 1081 when the pivoting portion 1054 is in the upright position as shown in FIGS. 30 and 32-37.

A workflow of performing a vertebral augmentation with the system 40 (i.e., a method for stabilizing a vertebral body) will now be described with particular reference to FIG. 29-. The vertebra with the offending vertebral body may be confirmed on fluoroscopic imaging. An incision may be made in the overlying paraspinal musculature lateral of midline generally in alignment with one of the pedicles of the vertebra.

The method begins positioning a distal end 52 of the access cannula 44 within the vertebral body such that a lumen 75 of the access cannula 44 provides access to an interior of the vertebral body along a longitudinal axis LA.

The method further includes coupling the introducer device 1000 to the access cannula 44 with the shaft 210 of the stylet 200 contained within an internal bore of the introducer device 1000 and with the flexible distal portion 216 extending between the pivoting portion 1054 and the base portion 1052 in the unconstrained state with the pivoting portion 1004 in the prone position, as shown in FIG. 29. In particular, the step includes coupling the hollow interior portion 1060 around a hub portion 46 of the access cannula 44 with the shaft 210 of the stylet 200 contained within an internal bore of the introducer device 1000 and with the flexible distal portion 216 extending between the pivoting portion 1054 and the base portion 1052 in the unconstrained state with the pivoting member 1050 in the prone position. In addition, the step of coupling also includes where the hollow interior portion 1060 is coupled around a hub portion 46 of the access cannula 44 such that the ball-nose spring 1074 is biasingly engaged to the hub portion 46, and in particular biasingly engaged to the ridged projection portion 1076, and with the shaft 210 of the stylet 200 contained within an internal bore of the introducer device 1000 and with the flexible distal portion 216 extending between the pivoting portion 1054 and the base portion 1052 in the unconstrained state with the pivoting member 1050 in the prone position.

Figure 30:
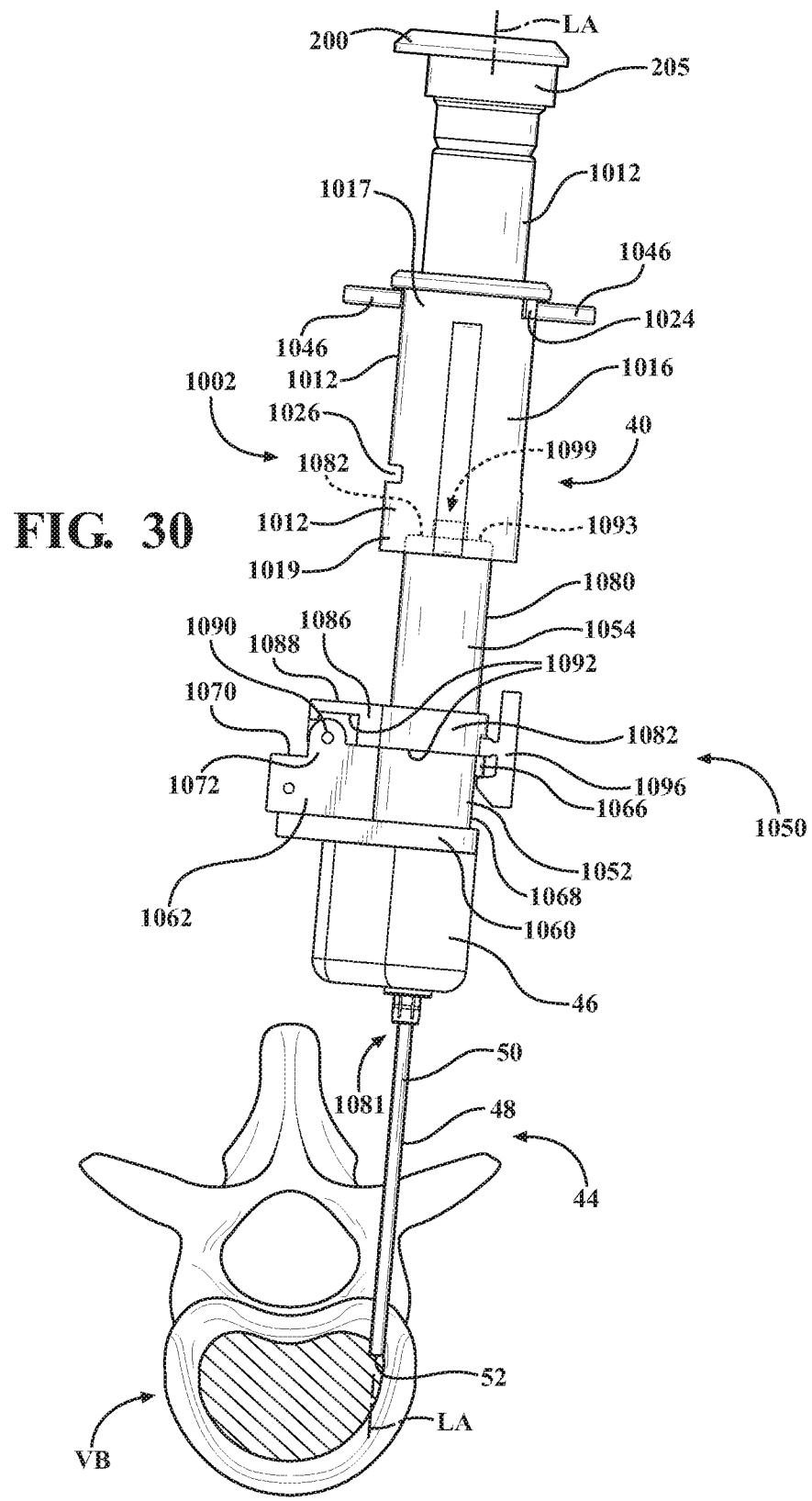
FIG. 30 illustrates the system of FIG. 29 with the pivoting portion of the introducer device moved from the prone position to the upright position while the hub assembly remains in the initial position.
Figure 31:
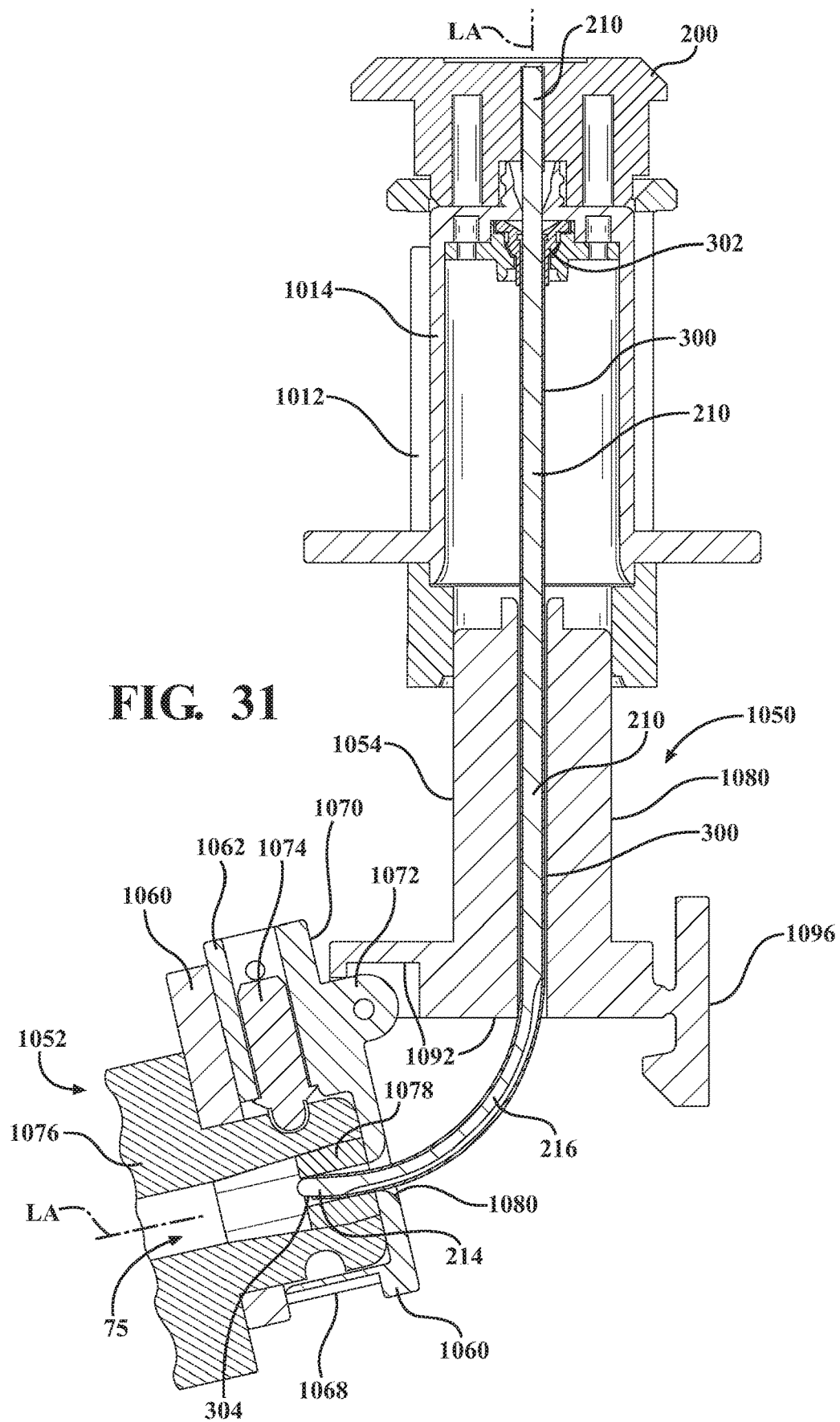
FIG. 31 is a section view of a portion of FIG. 29.
Figure 32:
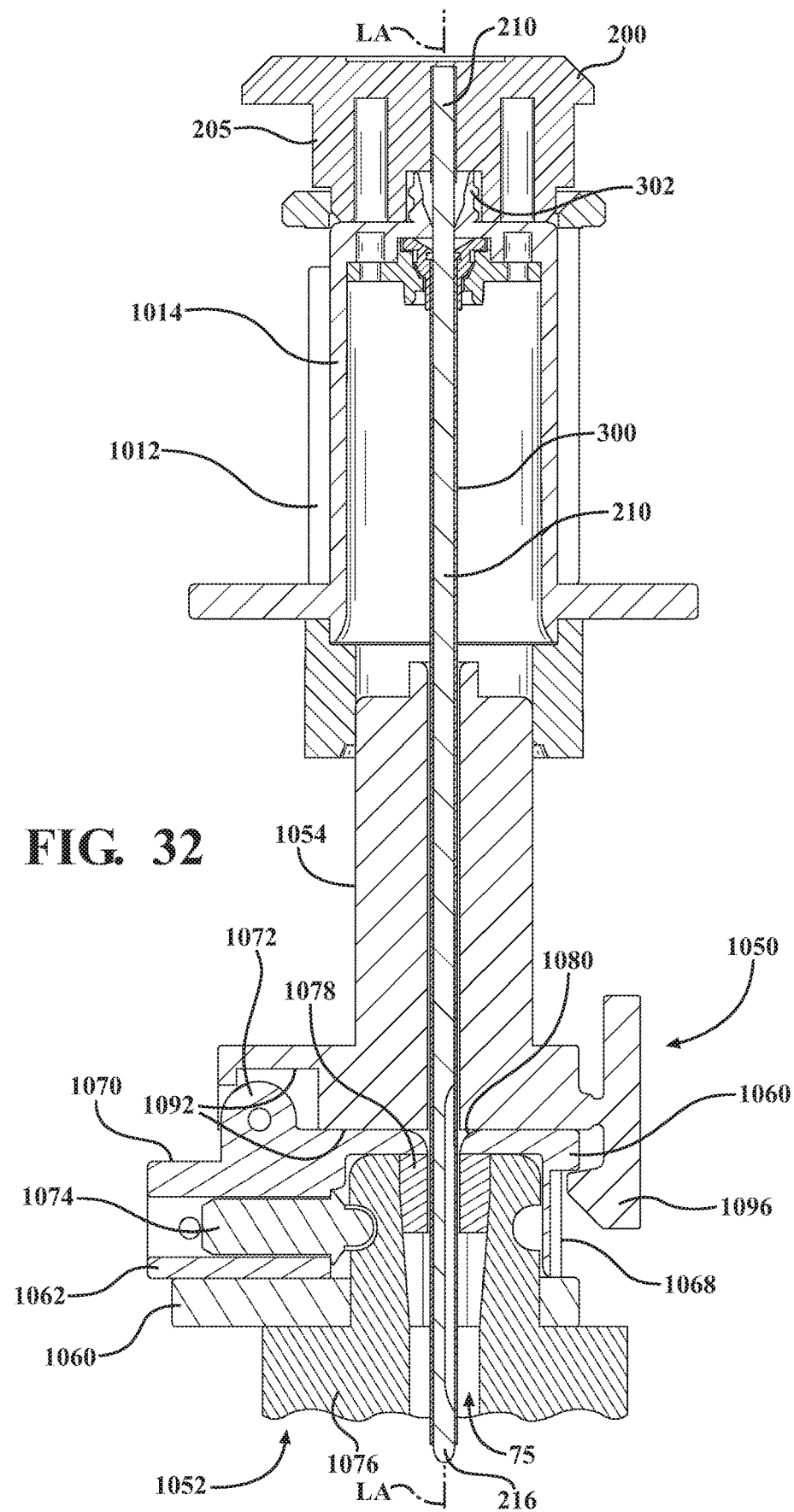
FIG. 32 is a section view of a portion of FIG. 30.

Next, as shown in FIGS. 30 and 32, the method continues by moving the pivoting portion 1054 from the prone position to the upright position, while maintaining the hub assembly 1002 in the initial position. In the upright position with the inner hub 1014 and hub assembly 1002 in the initial position, the distal end 214 of the shaft 210 of the stylet 200 is positioned within the lumen 75 between the distal end 52 and proximal end 50 of the cannula shaft 48 of the access cannula 44. In addition, the distal end 304 of the sheath 300 is also moved within the lumen 75. The flexible distal portion 216 is maintained in the constrained state within the cannula shaft 48. The step may also include the step of reversibly securing the pivoting portion 1054 to the base portion 1052 in the upright position. In particular, this step may include reversibly securing the pivoting portion 1054 to the base portion 1052 in the upright position by introducing the snap 1096 within the lip region 1066 of the base portion 1052 adjacent to the lip region 1066.

Figure 33:
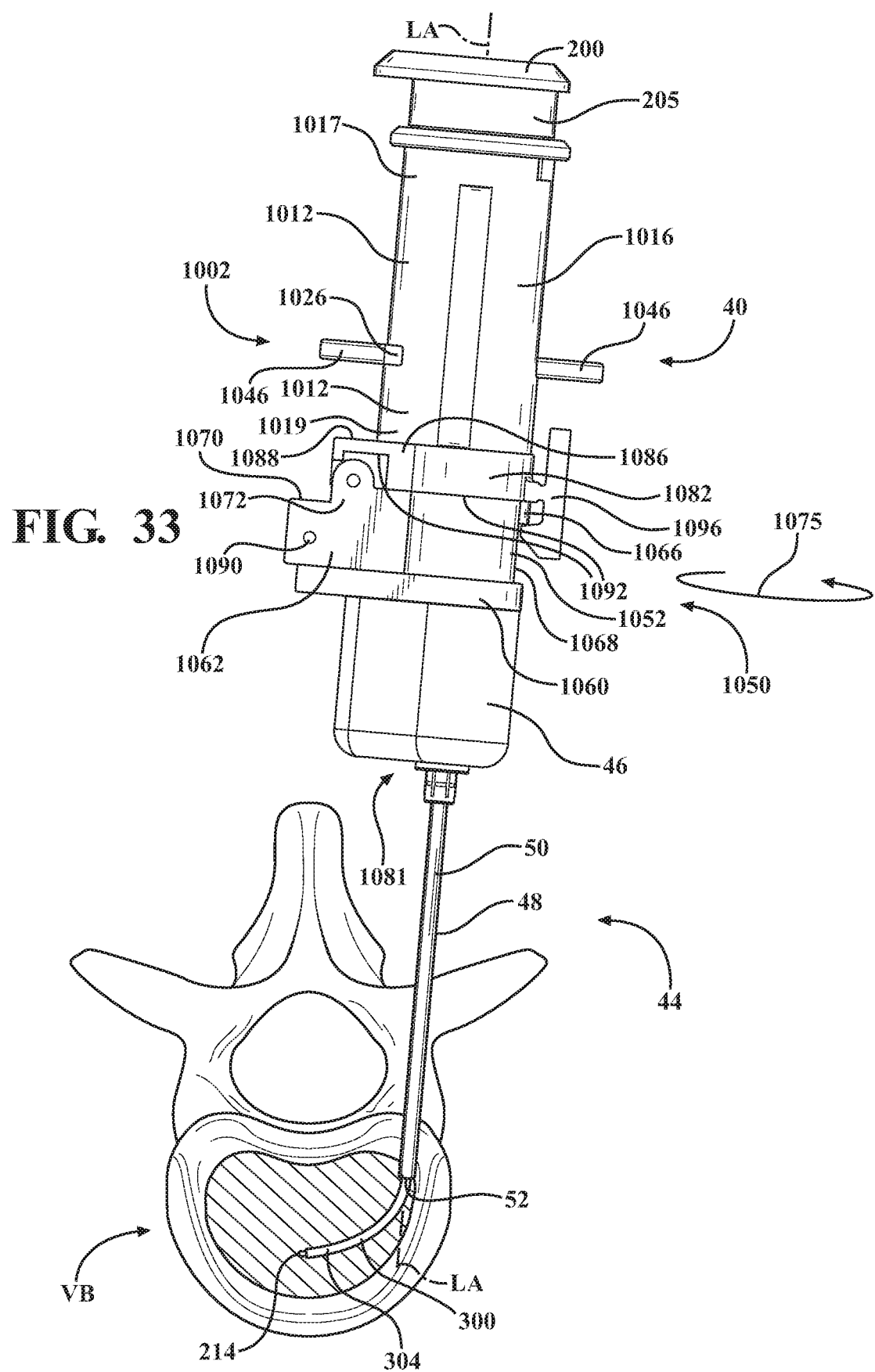
FIG. 33 is a perspective view of FIG. 30 with the hub assembly moved from the initial position to a supplemental and unlocked position.

Next, as shown in FIG. 33, the method continues by moving the hub assembly 1002 from an initial position to a supplemental position to move the distal end 214, 304 of each of the shaft 210 of the stylet 200 and the flexible sheath 300 beyond the distal end 52 of the access cannula 44 to within a target site in the vertebral body offset from the longitudinal axis LA. In this step, the flexible distal portion 216 of the shaft 210 of the stylet 200 is moved from the constrained state to the unconstrained state to displace cancellous bone within the target site of the vertebral body. In particular, the hub assembly 1002 with the coupled stylet 200 is first moved distally towards the pivoting portion 1054 such that the distal end 1019 of the outer hub 1012 is positioned adjacent to the outwardly projecting ledge region 1086. The practitioner then engages the alignment member 1046 to move the alignment member 1046 along the middle slot region 1028 from a position corresponding to the initial slot locking region 1024 (i.e., the initial position) to a position corresponding to the supplemental slot locking region 1026 (i.e., the supplemental position). The movement of the inner hub 1014 also results in the movement of the coupled stylet 200 (and hence the coupled stylet shaft 210) and the coupled sheath 300 distally as well relative to the outer hub 1012 and access cannula 44. This results in the distal end 214, 304 of the stylet shaft 210 and flexible sheath 300, respectively, moving beyond the distal end 52 of the access cannula 44 to within the target site in the vertebral body offset from the longitudinal axis LA, as also shown in FIG. 33, and with the flexible distal portion 216 moving from the constrained state to the unconstrained state to displace cancellous bone within the target site of the vertebral body target.

As a part of this step, the inner hub 1014 may be locked with the outer hub 1012 in the supplemental position by rotating the inner hub 1014 relative to the outer hub 1012 about the longitudinal axis LA in a first rotational direction (shown by arrow 1100 in FIG. 33). In particular, the practitioner can engage the alignment member 1046 to move the alignment member 1046 along the supplemental slot locking region 1026 in a direction away from the middle slot region 1028 (corresponding to the rotation illustrated by arrow 1100). In this position (i.e., the supplemental and locked position), the inner hub 1014 is prevented from moving in the longitudinal direction A by virtue of the alignment member 1046 contacting supplemental slot locking region 1026.

Next, the method continues by removing the stylet 200 from the introducer device 1000 while the inner hub 1014 is optionally locked with the outer hub 1012 in the supplemental position and locked position (or where the inner hub 1014 is not locked with the outer hub 1012 with the alignment member 1046 positioned at the intersection of the middle slot region 1028 and the supplemental slot locking region 1026 corresponding to the supplemental and unlocked position), with the distal end 304 of the flexible sheath 300 remaining positioned at the target site offset from the longitudinal axis LA.

Next, the balloon assembly 400 is coupled onto the introducer device 1000 while the hub assembly 1002 remains in the supplemental and locked position, as shown in FIG. 35. In particular, the balloon hub 402 is engaged with the outer hub 1012 to secure the balloon assembly 400 to the hub assembly 1002 with the hub assembly 1002 in the supplemental position. The balloon tube 404 may extend through the introducer device 1000, the pivoting member 1050, and the bore of the cannula hub portion 46 and the lumen 75 of the cannula shaft 48. With the hub assembly 1002 in the supplemental position, a distal end 410 of the balloon 406 is near or in registration with the distal end 304 of the sheath 300, as also shown in FIG. 35. The balloon 406 is in the deflated state and sheathed within the distal end 304 of the sheath 300 in the curved configuration.

Figure 36:
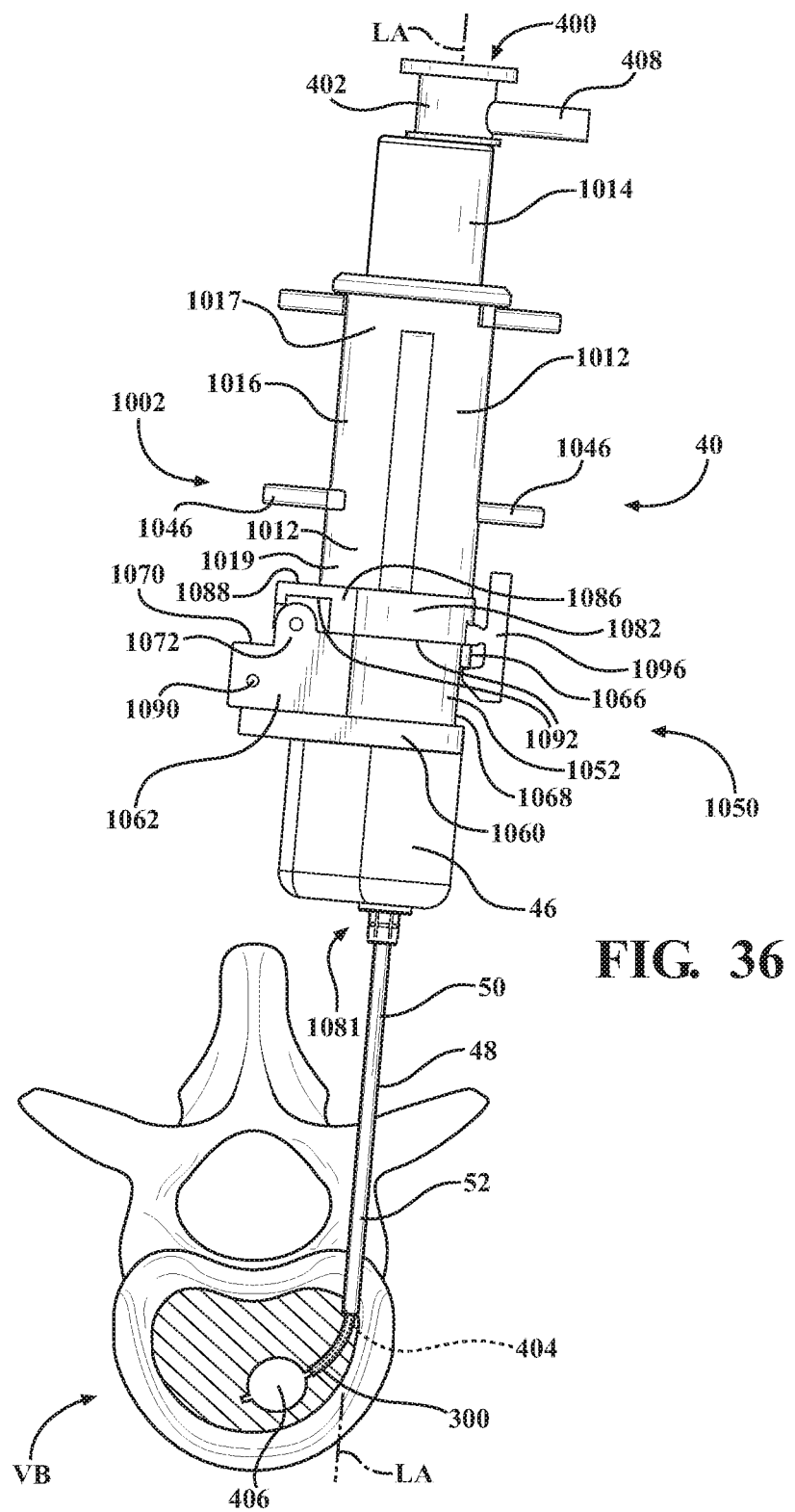
FIG. 36 is a perspective and partial section view of FIG. 34 with a balloon assembly coupled to the introducer device, with the introducer device in the upright and the hub assembly in the initial position, and with the balloon in an inflated state.

After the balloon 406 is positioned near or in registration with the distal end 304 of the sheath 300 in the deflated state, the balloon 406 may be unsheathed by moving the hub assembly 1002 from the supplemental position towards the initial position such that the balloon 406 extends beyond the distal end 304 of the sheath 300 and within the target area of the vertebral body. In particular, as shown in FIG. 36, the practitioner may move the hub assembly 1002 from the supplemental and locked position to the supplemental and unlocked position by moving the alignment member 1046 along the supplemental slot locking region 1026 in a direction towards from the middle slot region 1028, causing the inner hub 1014 to rotate around the longitudinal axis LA in the opposite direction to arrow 1100 in FIG. 33. Next, the practitioner moves the alignment member 1046 proximally away from the access cannula 44 within the middle slot region 1028, which causes the coupled sheath 300 to move proximally as well. The balloon 406 is unsheathed and exposed within the interior region of the vertebral body in the deflated state, after which the balloon 406 may be moved to the inflated state to displace the cancellous bone, as also shown in FIG. 36. In particular, after the deflated balloon 406 is unsheathed by moving the hub assembly 1002 to or towards the initial position, the balloon 406 may then be inflated by introducing fluid from the source of fluid through the balloon hub 402 and the balloon tube 404. The inflated balloon 406 displaces cancellous bone within the vertebral cavity. With the balloon 406 in the inflated state, the balloon 406 is returned to the deflated state to form the cavity 420 within the cancellous bone for delivery of the curable material from the cement delivery system 500. The balloon 406 is then removed by moving the balloon 406 into and through the sheath 300. The balloon assembly 400 is simultaneously or otherwise uncoupled from the hub assembly 680.

Figure 37:
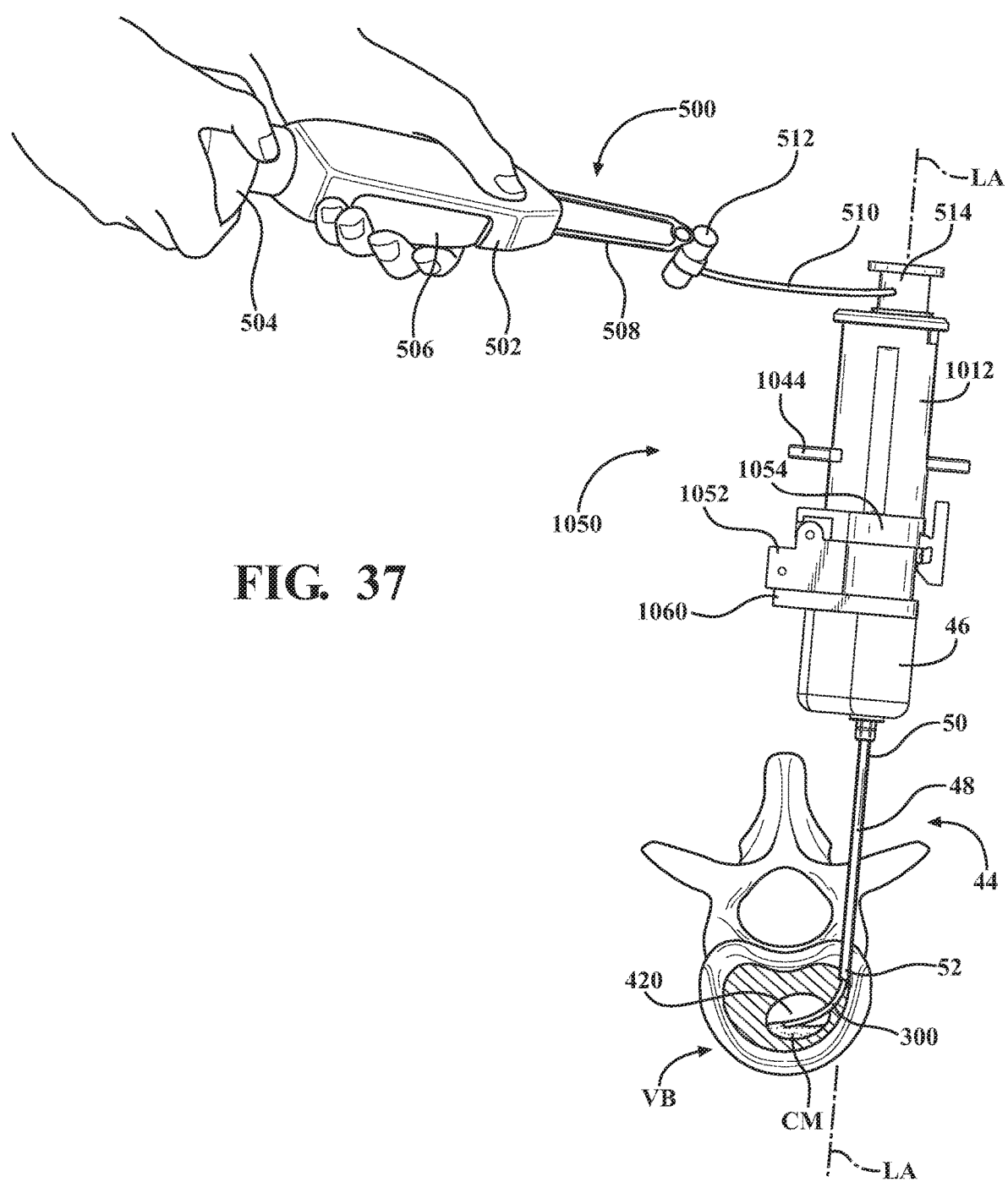
FIG. 37 is a perspective and partial section view of FIG. 34 with a bone cement delivery device coupled to the introducer device, with the introducer device in the upright position and the hub assembly in the supplemental and unlocked position, and with the bone delivery device delivering a curable material to the vertebral body.

Next, the cement delivery system 500, or cement delivery system 500, is coupled to the introducer device 642, as shown in FIG. 37. In particular, the cement delivery system 500 is coupled to the introducer device 1000, and in particular the cement delivery system 500 is engaged with the outer hub 1012 to secure the cement delivery system 500 to the hub assembly 1002 with the hub assembly 1002 in the supplemental position, or in the supplemental and locked position. A curable material CM, here bone cement, is then introduced from the cement delivery system 500 through the lumen 306 of the sheath 300 and into the internal cavity of the vertebral body to fill the internal cavity in the same manner generally described above with respect to FIG. 14. The cement delivery system 500 is then uncoupled from the introducer device 1000. The introducer device 1000 is then uncoupled from the access cannula 44 and removed. The trocar may be reintroduced through the access cannula 44, and the access cannula 44 and trocar removed from the vertebral body. The overlying tissue may be sutured, completing the stabilization of the vertebral body.

As an alternative in addition to placing cement or a balloon with the described delivery system, the system may further include a probe for RF ablation, such as a bipolar probe having two electrodes configured to generate a current to heat tissue disposed between the two electrodes. The method may include placing the probe for RF ablation with the techniques described herein. For example, the vertebra augmentation procedure may include directing an electrode assembly through the sheath with the sheath remaining curved. One exemplary electrode assembly that is sufficiently flexible for navigating the curved distal portion is described in United States Patent Publication No. 2013/0006232, published Jan. 3, 2013, the entire contents of which are hereby incorporated by reference. The electrode assembly may be bipolar or monopolar. It is contemplated that the electrode assembly may be irrigated such that a fluid is infused into the adjacent tissue prior to and/or during ablation. It is further contemplated that the electrode assembly may be cooled, for example, by circulating a fluid within pathways internal to the electrode assembly. With the electrode assembly being deployed contralaterally, procedures such as intraosseous tumor ablation, basivertebral denervation, and the like, are achievable through a unipedicular approach.

The systems and methods may further include placing other height-restoration devices other than balloons, such as those described in U.S. Pat. No. 9,579,130, which is hereby incorporated by reference. The systems and methods may be used to placed components in other bones, beyond vertebral bodies, and may be useful for soft-tissue applications as well, including intradiscal treatment.

Certain implementations may be described with reference to the following exemplary clauses:

Clause 1—A method of stabilizing a vertebral body with a system including an access cannula, an introducer device including a hub assembly, a telescoping introducer shaft coupled to the hub assembly and to the access cannula and having a plurality of shaft sections moveable between an extended position and a non-extended position with the plurality of shaft sections having a longer length in a longitudinal direction in the extended position and a shorter length in the non-extended position, a stylet including a shaft extending a length between a proximal end and a distal end and having a flexible distal portion near the distal end opposite a proximal end with the flexible distal portion movable between a constrained state in which the flexible distal portion is substantially straight and an unconstrained state in which the flexible distal portion includes a pre-set curve, and a flexible sheath at least partially overlying the flexible distal portion of the shaft, wherein the length of the shaft of the stylet between the proximal end and the distal end is shorter than the longer length of the plurality of shaft sections in the extended position and is longer than the shorter length of the plurality of shaft sections in the non-extended position, the method including: positioning a distal end of the access cannula within the vertebral body such that a lumen of the access cannula provides access to an interior of the vertebral body along a longitudinal axis; providing the introducer device with the shaft of the stylet contained within an internal bore of the telescoping introducer shaft and with the flexible distal portion in the constrained state; coupling the introducer device to the access cannula with the telescoping introducer shaft in the extended position in which the length of the stylet shaft and the flexible sheath are contained within the internal bore, with the flexible distal portion of the stylet remaining in the constrained state; moving the plurality of shaft portions of the telescoping introducer shaft from the extended position to a non-extended position to move the flexible distal portion of the stylet shaft and the flexible sheath from within the internal bore to within the lumen of the access cannula, with the flexible distal portion of the stylet remaining in the constrained state; moving the hub assembly from an initial position to a supplemental position to move the distal end of each of the stylet shaft and the flexible sheath from the access cannula to within a target site in the vertebral body offset from the longitudinal axis and to move the flexible distal portion of the stylet from the constrained state to the unconstrained state to displace cancellous bone within the target site of the vertebral body.

Clause 2—The method of clause 1, wherein the hub assembly includes an inner hub coupled to an outer hub, and wherein the method further includes: locking the inner hub with the outer hub in the supplemental position; removing the stylet from the introducer device while the inner hub is locked with the outer hub in the supplemental position and with the telescoping introducer shaft in the non-extended position, with the distal end of the flexible sheath remaining positioned at the target site offset from the longitudinal axis.

Clause 3—The method of clause 1, further including: providing a balloon assembly including: a balloon hub assembly including an inflation port, a balloon having a proximal end portion coupled to the inflation port and a distal end portion opposite the proximal end portion, and an inflation device coupled to the inflation port; coupling the balloon assembly to the introducer device while the hub assembly is in the supplemental position such that the balloon extends through the flexible sheath and such that the distal end portion of the balloon is contained within the target area of the vertebral body; moving the hub assembly from the supplemental position towards the initial position such that the distal end portion of the balloon extends from the distal end portion of the flexible sheath within the target area of the vertebral body; and inflating the distal end portion of the balloon within the target area with the inflation device after the step of moving the hub assembly from the supplemental position towards the initial position.

Clause 4—The method of clause 2, further including: providing a balloon assembly including: a balloon hub assembly including an inflation port, a balloon having a proximal end portion coupled to the inflation port and a distal end opposite the proximal end portion, and an inflation device coupled to the inflation port; coupling the balloon assembly to the introducer device when the inner hub is locked in the supplemental position such that the balloon extends through the flexible sheath and such that the distal end portion is contained within the target area of the vertebral body; unlocking the inner hub from the outer hub in the supplemental position; moving the inner hub from the supplemental position towards the initial position such that the distal end portion of the balloon extends from the distal end portion of the flexible sheath within the target area of the vertebral body; and inflating the distal end portion of the balloon within the target area with the inflation device after the step of moving the inner hub from the supplemental position towards the initial position.

Clause 5—The method of clause 3, further including: deflating the distal end portion of the balloon within the target area with the inflation device; removing the balloon assembly with the deflated distal end portion of the balloon from the introducer device; coupling a bone cement introduction device to the introducer device; introducing a bone cement from the bone cement introduction device through the flexible sheath and into the internal cavity; and uncoupling the bone cement introduction device from the introducer device after the step of introducing the bone cement.

Clause 6—The method of clause 4, further including: deflating the distal end portion of the balloon within the target area with the inflation device; removing the balloon assembly with the deflated distal end portion of the balloon from the introducer device; coupling a bone cement introduction device to the introducer device; introducing a bone cement from the bone cement introduction device through the flexible sheath and into the internal cavity; and uncoupling the bone cement introduction device from the introducer device after the step of introducing the bone cement.

Clause 7—A method of stabilizing a vertebral body with a system including an access cannula, an introducer device including a hub assembly and a pivoting member having a base portion removably coupled to the access cannula with the base member defining a first bore coaxial with the longitudinal axis when the base portion is removably coupled to the access cannula, and a pivoting portion coupled to the base portion and defining a second bore and moveable between a prone position and an upright position, wherein the pivoting portion is configured to move between a prone position in which the first and second bores are not coaxially aligned, and an upright position in which the first and second bores are coaxially aligned, a stylet including a shaft extending a length between a proximal end and a distal end and having a flexible distal portion near the distal end opposite a proximal end with the flexible distal portion movable between a constrained state and an unconstrained state in which the flexible distal portion is substantially straight and an unconstrained state and in which the flexible distal portion includes a pre-set curve, and a flexible sheath at least partially overlying the flexible distal portion of the shaft, the method including: positioning a distal end the access cannula within the vertebral body such that a lumen of the access cannula provides access to an interior of the vertebral body along a longitudinal axis; coupling the introducer device to the access cannula with the shaft of the stylet contained within an internal bore of the introducer device and with the flexible distal portion extending between the pivoting portion and the base portion in the unconstrained state and with the pivoting member in the prone position; moving the pivoting portion from the prone position to the upright position; moving the hub assembly from an initial position to a supplemental position to move the distal end of each of the stylet shaft and the flexible sheath from the access cannula to within a target site in the vertebral body offset from the longitudinal axis and to move the flexible distal portion of the stylet from the constrained state to the unconstrained state to displace cancellous bone within the target site of the vertebral body.

Clause 8—The method of clause 7, further including reversibly securing the pivoting portion to the base portion in the upright position.

Clause 9—The method of clause 8, wherein the pivoting portion includes a snap and wherein the outer surface of the base portion includes a recessed region, and wherein the step of reversibly securing the pivoting portion to the base portion in the upright position includes reversibly securing the pivoting portion to the base portion in the upright position by introducing the snap within the recessed region of the base portion when the pivoting portion is in the upright position.

Clause 10—The method of clause 7, wherein the provided base portion includes a hollow interior portion and wherein the step of coupling the introducer device to the access cannula includes: coupling the hollow interior portion around a hub portion of the access cannula with the shaft of the stylet contained within an internal bore of the introducer device and with the flexible distal portion extending between the pivoting portion and the base portion in the unconstrained state with the pivoting member in the prone position.

Clause 11—The method of clause 10, wherein the provided base portion further includes a ball-nose spring positioned within the hollow interior portion, and wherein the step of coupling the introducer device to the access cannula includes: coupling the hollow interior portion around a hub portion of the access cannula such that the ball-nose spring is biasingly engaged to the hub portion and with the shaft of the stylet contained within an internal bore of the introducer device and with the flexible distal portion extending between the pivoting portion and the base portion in the unconstrained state with the pivoting member in the prone position.

Clause 12—The method of clause 7, wherein the distal end of the stylet is positioned within the lumen between the distal end and proximal end of the access cannula when the pivoting portion is moved to the upright position and when the inner hub is moved in the initial position.

Clause 13—The method of clause 7, wherein the hub assembly includes an inner hub coupled to an outer hub, and wherein the method further includes: locking the inner hub with the outer hub in the supplemental position; and removing the stylet from the introducer device while the inner hub is locked with the outer hub in the supplemental position, with the distal end of the flexible sheath remaining positioned at the target site offset from the longitudinal axis.

Clause 14—The method of clause 7, further including: removing the stylet from the introducer device; providing a balloon assembly including: a balloon hub assembly including an inflation port, a balloon having a proximal end portion coupled to the inflation port and a distal end opposite the proximal end portion, and an inflation device coupled to the inflation port; coupling the balloon assembly to the introducer device such that the balloon extends through the flexible sheath and such that the distal end portion is contained within the target area of the vertebral body; moving the hub assembly from the supplemental position towards the initial position such that the distal end portion of the balloon extends from the distal end portion of the flexible sheath within the target area of the vertebral body; and inflating the distal end portion of the balloon within the target area with the inflation device after the step of moving the inner hub towards the initial position.

Clause 15—The method of clause 13, further including: providing a balloon assembly including: a balloon hub assembly including an inflation port, a balloon having a proximal end portion coupled to the inflation port and a distal end opposite the proximal end portion, and an inflation device coupled to the inflation port; coupling the balloon assembly to the introducer device such that the balloon extends through the flexible sheath and such that the distal end portion is contained within the target area of the vertebral body; unlocking the inner hub from the outer hub in the supplemental position; moving the inner hub from the supplemental position to the initial position such that the distal end portion of the flexible sheath is contained within the lumen; locking the inner hub to the outer hub in the initial position; an inflating the distal end portion of the balloon within the target area with the inflation device to create an internal cavity within the vertebral body after the step of locking the inner hub to the outer hub in the initial position.

Clause 16—The method of clause 15, further including: deflating the distal end portion of the balloon within the target area with the inflation device; removing the balloon assembly with the deflated distal end portion of the balloon from the introducer device; coupling a bone cement introduction device to the introducer device; introducing a bone cement from the bone cement introduction device through the flexible sheath and into the internal cavity; and uncoupling the bone cement introduction device from the introducer device after the step of introducing the bone cement.

The foregoing disclosure is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A system for stabilizing a vertebral body, said system comprising:
    an access cannula comprising a hub portion and a cannula shaft, said cannula shaft including a proximal end and an opposing distal end positionable within the vertebral body, said cannula shaft defining a lumen along a longitudinal axis;
    an introducer device comprising:
        a telescoping introducer shaft coupled to a hub assembly and configured to be removably coupled to said hub portion of said access cannula, said telescoping introducer shaft having a plurality of shaft sections moveable between an extended position and a non-extended position with said plurality of shaft sections having a longer length in a longitudinal direction in said extended position and a shorter length in said non-extended position, said telescoping introducer shaft defining an internal bore extending along said longitudinal axis with said internal bore aligned with and in open communication with said lumen along said longitudinal axis when said telescoping introducer shaft is coupled to said hub portion of said access cannula; and
    a stylet within said internal bore of said telescoping introducer shaft of said introducer device, said stylet including a stylet shaft extending a length between a proximal end and a distal end and having a flexible distal portion near said distal end, said flexible distal portion comprising a pre-set curve in an unconstrained state and movable between said unconstrained state and a constrained state in which said flexible distal portion is substantially straight, wherein said flexible distal portion is in said constrained state when said flexible distal portion is contained within said internal bore when said telescoping introducer shaft is in said extended position, and wherein collapsing said telescoping introducer shaft from said extended position to said non-extended position moves said flexible distal portion of said stylet shaft from within said internal bore to within said lumen of said access cannula in said constrained state.

2. The system of claim 1, wherein said hub assembly further comprises an outer hub, and an inner hub coupled to said stylet and moveable along said longitudinal axis relative to said outer hub between an initial position and a supplemental position in which said inner hub is moved distally relative to said outer hub, wherein said length of said stylet shaft is sufficient for said flexible distal portion of said stylet shaft to extend through and be operable beyond said distal end of said access cannula when said telescoping introducer shaft is in said non-extended position and when said inner hub is in said supplemental position such that said pre-set curve is no longer constrained by said access cannula and moves from constrained state to said unconstrained state to a target area within the vertebral body that is offset from said longitudinal axis.

3. The system of claim 2, further comprising a flexible sheath at least partially overlying said stylet shaft when said stylet is inserted within said internal bore, with said flexible sheath comprising a proximal end coupled to said inner hub and an opposing distal end positionable near said distal end of said stylet shaft.

4. The system of claim 2, wherein said distal end of said stylet shaft is in registration with said distal end of said access cannula when said telescoping introducer shaft is in the non-extended position and when said inner hub is in said initial position.

5. The system of claim 2, wherein said inner hub includes an initial locking feature and wherein said outer hub include a complementary locking feature, with said initial locking feature configured for locking with said complementary locking feature when said inner hub is in said initial position, and wherein said inner hub includes a supplemental locking feature and wherein said outer hub include a complementary supplemental locking feature, with said supplemental locking feature configured for locking with said complementary supplemental locking feature when said inner hub is in said supplemental position.

6. A system for stabilizing a vertebral body, said system comprising:
   an access cannula comprising a hub portion and a cannula shaft, said cannula shaft including a proximal end and an opposing distal end positionable within the vertebral body, said cannula shaft defining a lumen along a longitudinal axis;
   an introducer device comprising:
      a hub assembly moveable along said longitudinal axis between an initial position and a supplemental position; and
      a pivoting member including a base portion coupled to a pivoting portion,
         said base portion configured for coupling to said hub portion of said access cannula and defining a first bore coaxial with said longitudinal axis when said base portion is coupled to said hub portion;
         said pivoting portion coupled to said hub assembly and defining a second bore, said pivoting member pivotable relative to said base portion between an upright position in which said first and second bores are coaxially aligned and a prone position in which said first and second bores are not coaxially aligned; and
   a stylet for insertion within said introducer device, said stylet including a stylet shaft extending a length between a proximal end and a distal end and having a flexible distal portion near said distal end, said flexible distal portion comprising a pre-set curve in an unconstrained state and movable between said unconstrained state and a constrained state in which said flexible distal portion is substantially straight, said stylet moveable between a non-deployed position and a deployed position when said pivoting portion is coupled to said base portion in said upright position,
      wherein a portion of said distal end of said stylet shaft is configured to extend through said access cannula when said pivoting member is in said upright position and said hub assembly is in said supplemental position and wherein said stylet is movable to said deployed position such that said pre-set curve moves from said constrained state to said unconstrained state in a target area within the vertebral body that is offset from said longitudinal axis.

7. The system of claim 6, further comprising a flexible sheath at least partially overlying said stylet shaft when said stylet is inserted within said first and second bores, with said flexible sheath comprising a proximal end coupled to said hub assembly and an opposing distal end positionable near said distal end of said stylet shaft.

8. The system of claim 7, wherein said hub assembly comprises:
   an outer hub; and
   an inner hub coupled to said outer hub and moveable along said longitudinal axis relative to and within said outer hub between said initial position and said supplemental position.

9. The system of claim 8, wherein said distal end of said stylet shaft is in registration with said distal end of said access cannula when said inner hub is in said initial position and said stylet is in said deployed position and said pivoting portion is in said upright position.

10. The system of claim 8, wherein said inner hub includes a locking feature and wherein said outer hub include a complementary locking feature, with said locking feature configured for locking with said complementary locking feature when said inner hub is in said deployed position.

11. The system of claim 8, further comprising a balloon assembly coupled to said introducer device after removal of said stylet from said introducer device, said balloon assembly comprising:
   a balloon hub assembly coupled to said introducer device, said balloon hub assembly including an inflation port;
   a balloon having a proximal end portion coupled to said inflation port, said balloon for extending through said flexible sheath such that a distal end portion opposite said proximal end portion is contained within the target area of the vertebral body; and
   an inflation device coupled to said inflation port, said inflation device configured for inflating and deflating said distal end portion of said balloon within the target area of the vertebral body.

12. The system of claim 11, wherein said distal end of said flexible sheath is positioned around a portion of said distal end portion of said balloon within the vertebral body when said inner hub is in said supplemental position.

13. The system of claim 11, wherein said distal end of said flexible sheath is configured to be retracted when said inner hub is moving in a direction from said supplemental position towards said initial position.

14. The system of claim 8, wherein said pivoting portion includes a snap that is configured to be releasably coupled to said base portion when said pivoting portion is in said upright position.

15. The system of claim 8, wherein said base portion includes a hollow interior portion that is positioned around said hub portion of said access cannula when said base portion is coupled to said hub portion of said access cannula.

16. The system of claim 15, wherein said base portion further includes a ball-nose spring positioned within said hollow interior portion, and wherein said ball-nose spring is biasingly engaged to said hub portion of said access cannula when said base portion is coupled to said hub portion of said access cannula.

17. The system of claim 8, wherein a bottom surface of said pivoting portion and a top surface of said base portion define an angle therebetween when said pivoting portion is in said prone position, said angle being between 0 and 75 degrees.

18. The system of claim 6, wherein said distal end of said stylet shaft is in registration with said distal end of said access cannula when said hub assembly is in said initial position and said stylet is in said deployed position and said pivoting member is in said upright position.

19. A system for stabilizing a vertebral body, said system comprising:
an access cannula comprising a cannula hub and a cannula shaft, said cannula shaft including a proximal end and an opposing distal end positionable within the vertebral body, said cannula shaft defining a lumen along a longitudinal axis;
an introducer device comprising:
a stylet comprising a length defined between a proximal end and a distal end, and a flexible distal portion near said distal end and comprising a pre-set curve in an unconstrained state; and
a pivoting member comprising a base portion removably coupled to said cannula hub and defining a first bore coaxial with said longitudinal axis when said base portion is removably coupled to said cannula hub, and a pivoting portion pivotably coupled to said base portion and defining a second bore, wherein said pivoting portion is configured to move between a prone position in which said first and second bores are not coaxially aligned, and an upright position in which said first and second bores are coaxially aligned,
wherein said flexible distal portion extends between said pivoting portion and said base portion in said unconstrained state with said pivoting member in the prone position, and wherein said flexible distal portion is movable from said unconstrained state to a constrained state in which said flexible distal portion is substantially straight when said pivoting member is moved to said upright position.

20. The system of claim 19, further comprising a hub assembly coupled at or near said proximal end of said stylet with said pivoting member spaced apart from said hub assembly by a portion of said length of said stylet, wherein said hub assembly is configured to be distally advanced towards said pivoting member with said pivoting member in said upright position such that said stylet is advanced into said cannula shaft in said constrained state.

* * * * *